United States Patent
Yee et al.

(10) Patent No.: US 11,740,231 B2
(45) Date of Patent: Aug. 29, 2023

(54) ARTICLES OF MANUFACTURE AND METHODS RELATED TO TOXICITY ASSOCIATED WITH CELL THERAPY

(71) Applicant: Juno Therapeutics, Inc., Seattle, WA (US)

(72) Inventors: Nathan Yee, Seattle, WA (US); Christopher Glen Ramsborg, Seattle, WA (US); Tina Albertson, Seattle, WA (US); Ryan Larson, Seattle, WA (US); He Li, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 804 days.

(21) Appl. No.: 16/617,477

(22) PCT Filed: Jun. 1, 2018

(86) PCT No.: PCT/US2018/035752
§ 371 (c)(1),
(2) Date: Nov. 26, 2019

(87) PCT Pub. No.: WO2018/223098
PCT Pub. Date: Dec. 6, 2018

(65) Prior Publication Data
US 2020/0110077 A1   Apr. 9, 2020

Related U.S. Application Data

(60) Provisional application No. 62/515,526, filed on Jun. 5, 2017, provisional application No. 62/514,762, filed on Jun. 2, 2017.

(51) Int. Cl.
| | | |
|---|---|---|
| *G01N 33/50* | (2006.01) |
| *A61P 35/00* | (2006.01) |
| *A61K 35/17* | (2015.01) |
| *C07K 14/725* | (2006.01) |
| *C07K 14/705* | (2006.01) |
| *C07K 16/28* | (2006.01) |
| *C12N 5/0783* | (2010.01) |
| *G01N 33/574* | (2006.01) |

(52) U.S. Cl.
CPC ......... *G01N 33/5091* (2013.01); *A61K 35/17* (2013.01); *A61P 35/00* (2018.01); *C07K 14/7051* (2013.01); *C07K 14/70521* (2013.01); *C07K 14/70578* (2013.01); *C07K 16/2803* (2013.01); *C12N 5/0636* (2013.01); *G01N 33/5047* (2013.01); *G01N 33/57407* (2013.01); *C07K 2319/02* (2013.01)

(58) Field of Classification Search
CPC ........... G01N 33/5091; G01N 33/5047; G01N 33/57407; A61K 35/17; A61K 2039/5156; A61K 2039/5158; A61K 39/0011; A61P 35/00; C07K 14/7051; C07K 14/70521; C07K 14/70578; C07K 16/2803; C07K 2319/02; C07K 2319/03; C12N 5/0636
See application file for complete search history.

(56) References Cited

U.S. PATENT DOCUMENTS

| | | |
|---|---|---|
| 3,799,934 A | 3/1974 | Water |
| 4,452,773 A | 6/1984 | Molday |
| 4,690,915 A | 9/1987 | Rosenberg |
| 4,795,698 A | 1/1989 | Owen |
| 5,087,616 A | 2/1992 | Myers |
| 5,200,084 A | 4/1993 | Liberti |
| 5,219,740 A | 6/1993 | Miller |
| 5,527,814 A | 6/1996 | Louvel |
| 5,591,827 A | 1/1997 | Brakenhoff |
| 6,040,177 A | 3/2000 | Riddell |
| 6,060,273 A | 5/2000 | Dirks |
| 6,207,453 B1 | 3/2001 | Maass |
| 6,410,319 B1 | 6/2002 | Raubitschek |
| 6,451,995 B1 | 9/2002 | Cheung |
| 7,070,995 B2 | 7/2006 | Jensen |
| 7,265,209 B2 | 9/2007 | Jensen |

(Continued)

FOREIGN PATENT DOCUMENTS

| | | |
|---|---|---|
| EP | 0452342 | 11/1994 |
| EP | 2537416 | 11/2014 |

(Continued)

OTHER PUBLICATIONS

Cros et al. (Immunity, 33: 375-386, 2010).*

(Continued)

*Primary Examiner* — Nelson B Moseley, II
(74) *Attorney, Agent, or Firm* — Morrison & Foerster LLP

(57) ABSTRACT

Provided are methods and articles of manufacture for use with cell therapy for the treatment of diseases or conditions, e.g., cancer, including for predicting and treating a toxicity. In some embodiments, the toxicity is a neurotoxicity or cytokine release syndrome (CRS), such as a severe neurotoxicity or a severe CRS. The methods generally involve detecting a marker by assaying a biological sample from a subject that is a candidate for treatment, optionally with a cell therapy, to determine if the subject is at risk for developing the toxicity, such as neurotoxicity or CRS or severe neurotoxicity or severe CRS. In some embodiments, the methods and articles of manufacture further includes a regent for assaying the biological sample and instructions for determining the percentage or number of cells positive for the marker in the biological sample.

33 Claims, 13 Drawing Sheets
Specification includes a Sequence Listing.

(56) References Cited

U.S. PATENT DOCUMENTS

| | | | |
|---|---|---|---|
| 7,354,762 | B2 | 4/2008 | Jensen |
| 7,446,179 | B2 | 11/2008 | Jensen |
| 7,446,190 | B2 | 11/2008 | Sadelain |
| 7,446,191 | B2 | 11/2008 | Jensen |
| 7,514,444 | B2 | 4/2009 | Honigberg |
| 7,645,755 | B2 | 1/2010 | Illig |
| 7,893,075 | B2 | 2/2011 | Zhang |
| 8,008,309 | B2 | 8/2011 | Honigberg |
| 8,247,425 | B2 | 8/2012 | Bazhina |
| 8,324,353 | B2 | 12/2012 | Jensen |
| 8,339,645 | B2 | 12/2012 | Nakawaki |
| 8,389,282 | B2 | 3/2013 | Sadelain |
| 8,399,514 | B2 | 3/2013 | Lukashev |
| 8,476,284 | B2 | 7/2013 | Honigberg |
| 8,479,118 | B2 | 7/2013 | Lyndersay |
| 8,497,277 | B2 | 7/2013 | Honigberg |
| 8,562,991 | B2 | 10/2013 | Igawa |
| 8,697,711 | B2 | 4/2014 | Honigberg |
| 8,703,780 | B2 | 4/2014 | Honigberg |
| 8,735,403 | B2 | 5/2014 | Honigberg |
| 8,754,090 | B2 | 6/2014 | Buggy |
| 8,754,091 | B2 | 6/2014 | Honigberg |
| 8,802,374 | B2 | 8/2014 | Jensen |
| 8,911,993 | B2 | 12/2014 | June |
| 8,957,079 | B2 | 2/2015 | Honigberg |
| 8,999,999 | B2 | 4/2015 | Buggy |
| 9,125,889 | B2 | 9/2015 | Buggy |
| 9,181,257 | B2 | 11/2015 | Honigberg |
| 9,296,753 | B2 | 3/2016 | Smyth |
| 2002/0131960 | A1 | 9/2002 | Sadelain |
| 2002/0150914 | A1 | 10/2002 | Andersen |
| 2003/0223994 | A1 | 12/2003 | Hoogenboom |
| 2004/0191260 | A1 | 9/2004 | Reiter |
| 2006/0034850 | A1 | 2/2006 | Weidanz |
| 2007/0092530 | A1 | 4/2007 | Weidanz |
| 2007/0116690 | A1 | 5/2007 | Yang |
| 2009/0215053 | A1 | 8/2009 | Galon et al. |
| 2009/0226474 | A1 | 9/2009 | Hawkins |
| 2009/0304679 | A1 | 12/2009 | Weidanz |
| 2010/0190755 | A1 | 7/2010 | Abato |
| 2011/0003380 | A1 | 1/2011 | Miltenyi |
| 2011/0044998 | A1 | 2/2011 | Bedian |
| 2013/0149337 | A1 | 6/2013 | Cooper |
| 2013/0287748 | A1 | 10/2013 | June |
| 2014/0065141 | A1 | 3/2014 | Daniel |
| 2014/0227219 | A1* | 8/2014 | Singla ............... A61K 45/06 514/1.9 |
| 2014/0294841 | A1 | 10/2014 | Scheinberg |
| 2015/0119267 | A1 | 4/2015 | Joyce |
| 2016/0206656 | A1 | 7/2016 | Gilbert |
| 2017/0306416 | A1 | 10/2017 | Bedoya et al. |

FOREIGN PATENT DOCUMENTS

| | | |
|---|---|---|
| EP | 2277543 B1 | 12/2015 |
| WO | WO-1992/008796 | 5/1992 |
| WO | WO-1994/028143 | 12/1994 |
| WO | WO-1996/013593 | 5/1996 |
| WO | WO-1996/018105 | 6/1996 |
| WO | WO-1999/018129 | 4/1999 |
| WO | WO-1999/060120 | 11/1999 |
| WO | WO0014257 A1 | 3/2000 |
| WO | WO2003068201 A2 | 8/2003 |
| WO | WO2004033685 A1 | 4/2004 |
| WO | WO2006000830 A2 | 1/2006 |
| WO | WO2006009755 A2 | 1/2006 |
| WO | WO2008063888 A2 | 5/2008 |
| WO | WO2009072003 A2 | 6/2009 |
| WO | WO2009099553 A2 | 8/2009 |
| WO | WO2010033140 A2 | 3/2010 |
| WO | WO-2011/011453 | 1/2011 |
| WO | WO2011056983 A1 | 5/2011 |
| WO | WO2011044186 A9 | 6/2011 |
| WO | WO2012129514 A1 | 9/2012 |
| WO | WO-2003/020763 | 3/2013 |
| WO | WO2013071154 A1 | 5/2013 |
| WO | WO2013123061 A1 | 8/2013 |
| WO | WO2013126726 A1 | 8/2013 |
| WO | WO2013166321 A1 | 11/2013 |
| WO | WO2014001802 A1 | 1/2014 |
| WO | WO2014031687 A1 | 2/2014 |
| WO | WO2014055668 A1 | 4/2014 |
| WO | WO-2015/136001 | 9/2015 |
| WO | WO-2015/142314 | 9/2015 |
| WO | WO2016057705 A1 | 4/2016 |
| WO | WO-2017/040930 | 3/2017 |

OTHER PUBLICATIONS

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Barret et al., "Interleukin 6 is not Made by Chimeric Antigen Receptor T Cells and Does not Impact Their Function," (2016) Blood 128:654. Abstract 654. Presented at ASH 58th Annual Meeting San Diego, CA (Dec. 3-6, 2016).

Barrett et al., "Chimeric antigen receptor therapy for cancer," Annu Rev Med. (2014);65:333-47.

Basu et al., Use of a novel hemoadsorption device for cytokine removal as adjuvant therapy in a patient with septic shock with multi-organ dysfunction: A case study, Indian J Crit Care Med (2014) 18(12):822-824.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177):177ra38.

Burns et al., "Vesicular stomatitis virus G glycoprotein pseudotyped retroviral vectors: concentration to very high titer and efficient gene transfer into mammalian and nonmammalian cells," PNAS. USA (1993) 90:8033-8037.

Butovsky et al., "Targeting miR-155 restores abnormal microglia and attenuates disease in SOD1 mice," Ann Neurol (2015) 77(1):75-99.

Carlens et al., "Ex vivo T lymphocyte expansion for retroviral transduction: influence of serum-free media on variations in cell expansion rates and lymphocyte subset distribution," Exp Hematol (2000) 28(10): 1137-46.

Carrillo et al., The Multiple Sequence Alignment Problem in Biology, SIAM J Applied Math (1988) 48: 1073.

Cavaletti et al., "Chemotherapy-induced peripheral neurotoxicity," Nature Reviews Neurology (2010) 6, 657-666.

Cavalieri et al., "Human T lymphocytes transduced by lentiviral vectors in the absence of TCR activation maintain an intact immune competence," Blood (2003) 102(2): 497-505.

Cheadle, E.J. et al. (2012). "Chimeric Antigen Receptors for T-Cell Based Therapy," Methods Mol. Biol. 907:645-666.

Chervin et al., "Engineering higher affinity T cell receptors using a T cell display system," J Immunol Methods, (2008) 339(2):175-84.

Chicaybam et al., "An efficient low cost method for gene transfer to T lymphocytes," PLoS ONE (2013) 8(3): e60298.

Cho et al., "Human mammalian cell sorting using a highly integrated micro-fabricated fluorescence-activated cell sorter (microFACS)," Lab Chip (2010) 10: 1567-1573.

Chothia et al., "The outline structure of the T-cell alpha beta receptor," EMBO J. (1988) 7(12):3745-3755.

Clackson, T. et al. (Aug. 15, 1991). "Making Antibody Fragments Using Phage Display Libraries," Nature 352:624-628.

Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.

(56) References Cited

OTHER PUBLICATIONS

Cohen et al., "Recombinant antibodies with MHC-restricted, peptide-specific, T-cell receptor-like specificity: new tools to study antigen presentation and TCR-peptide-MHC interactions," J Mol Recognit. (2003) 16(5):324-332.
Conway et al., "Inhibition of colony-stimulating-factor-1 signaling in vivo with the orally bioavailable cFMS kinase inhibitor GW2580," Proc Natl Acad Sci U.S.A (2005) 102(44):16078-16083.
Cooper et al., "T-cell clones can be rendered specific for CD19: toward the selective augmentation of the graft-versus-B-lineage leukemia effect," Blood (2003) 101:1637-1644.
Crump et al., "Outcomes in Refractory Diffuse Large B-cell Lymphoma: Results From the International SCHOLAR-1 Study," Blood (2017) 130 (16): 1800-1808.
Dagher et al., "Colony-stimulating factor 1 receptor inhibition prevents microglial plaque association and improves cognition in 3xTg-AD mice," J Neuroinflammation (2015) 12:139.
Davila et al., "CD19 CAR-targeted T cells induce long-term remission and B Cell Aplasia in an immunocompetent mouse model of B cell acute lymphoblastic leukemia," PLoS ONE (2013) 8(4):e61338.
Davila et al., "Efficacy and toxicity management of 19-28z CAR T cell therapy in B cell acute lymphoblastic leukemia," Sci Transl Med (2014) 6:224ra25.
De Felipe, "Skipping the co-expression problem: the new 2A "Chysel" technology," Genet Vaccines Ther (2004) Sep. 2013;2:13.
De Felipe, "Targeting of proteins derived from self-processing polyproteins containing multiple signal sequences," Traffic (2004) 5(8):616-626.
Dobber et al., "The in vivo effects of neutralizing antibodies against IFN-gamma, IL-4, or IL-10 on the humoral mmune response in young and aged mice," Cell Immunol (1995)160(2):185-192.
Fedorov et al., "PD-1- and CTLA-4-Based Inhibitory Chimeric Antigen Receptors (iCARs) Divert Off-Target Immunotherapy Responses," Science Translational Medicine (2013) 5(215):215ra172.
Fingerle et al., "The novel subset of CD14+/CD16+ blood monocytes is expanded in sepsis patients," Blood (1993) 82(10):3170-3176.
Fleischmann et al., "Safety of extended treatment with anakinra in patients with rheumatoid arthritis," Ann Rheum Dis (2006) 65(8):1006-1012.
Godin et al., "Microfluidics and photonics for Bio-System-on-a-Chip: a review of advancements in technology towards a microfluidic flow cytometry chip," J Biophoton. (2008) 1(5):355-376.
Gong et al., "An Antagonist of Monocyte Chemoattractant Protein 1 (MCP-1) Inhibits Arthritis in the MRL-Ipr Mouse Model," J Exp Med (1997) 186(1):131-137.
Grupp et al., "Chimeric antigen receptor-modified T cells for acute lymphoid leukemia," N. Engl. J. Med. (2013) 368:1509-1518.
Gust et al., "Endothelial Activation and Blood-Brain Barrier Disruption in Neurotoxicity after Adoptive Immunotherapy with CD19 CAR-T Cells," Cancer Discovery (2017) 7(12): 1404-1419.
Haegel et al., "TG3003, an immunomodulatory anti-CD115 mAb targeting m2-macrophage polarization in the tumor microenvironment," Cancer Res AACR Abstract 288 (2015).
Hannum et al., "Interleukin-1 receptor antagonist activity of a human interleukin-1 inhibitor," Nature (1990) 343:336-340.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Hoing et al., "Discovery of inhibitors of microglial neurotoxicity acting through multiple mechanisms using a stem-cell-based phenotypic assay," Cell Stem Cell (2012) 11 (5):620-632.
Holler et al., "In vitro evolution of a T cell receptor with high affinity for peptide/MHC," Proc Natl Acad Sci USA, (2000) 97(10):5387-92.
Holler et al., "TCRs with high affinity for foreign pMHC show self-reactivity," Nat Immunol (2003) 4(1):55-62.
Hozumi et al.,"Comparative Analysis of Hepatic CD14 Expression between Two Different Endotoxin Shock Model Mice: Relation between Hepatic Injury and CD14 Expression," PLoS One. (2013) 8(1):e53692.
Huang et al., "DNA transposons for modification of human primary T lymphocytes," Methods Mol Biol (2009) 506:115-126.
Hudecek et al., "Receptor affinity and extracellular domain modifications affect tumor recognition by ROR1-specific chimeric antigen receptor T cells," Clin Cancer Res. (Jun. 15, 2013);19(12):3153-3164.
Hunter et al., "Neutralizing anti-IL-10 antibody blocks the protective effect of tapeworm infection in a murine model of chemically induced colitis," J Immunol (2005) 174(11):7368-7375.
Janeway et al., Immunobiology: The Immune System in Health and Disease, 3rd ED., Current Biology Publications (1997), p. 4:33.
Johnston, "Biolistic transformation: microbes to mice," Nature (1990) 346:776-777.
Jores et al., "Resolution of hypervariable regions in T-cell receptor beta chains by a modified Wu-Kabat index of amino acid diversity," Proc Natl Acad Sci U S A. (1990) 87(23):9138-9142.
Kindt, T.J. et al. (2007). "Antigens And Antibodies," Chapter 4 In Kuby Immunology 6th Ed., W.H. Freeman and Co., p. 91.
Kivisakk et al., "Natalizumab treatment is associated with peripheral sequestration of proinflammatory T cells," Neurology (2009) 72(22):1922-1930.
Klebanoff et al., "Sorting through subsets: which T-cell populations mediate highly effective adoptive immunotherapy?," J Immunother. (2012) 35(9): 651-660.
Kochenderfer et al., "B cell depletion and remissions of malignancy a long with cytokine associated toxicity in a clinical trial of anti-CD 19 chimeric-antigen receptor-transduced T cells," Blood (2012) 119(12):2709-2720.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nat Rev Clin Oncol (2013) 10(5):267-276.
Koste et al., "T-cell receptor transfer into human T cells with ecotropic retroviral vectors," Gene Therapy (2014) 21:533-538.
Kotb et al., "Bacterial pyrogenic exotoxins as superantigens," Clinical Microbiology Reviews (1995) 8:411-426.
Kurucz et al., "A bacterially expressed single-chain Fv construct from the 2B4 T-cell receptor," PNAS (1993) 90(9):3830-3834.
Lee et al., "Current concepts in the diagnosis and management of cytokine release syndrome," Blood. (2014) 124(2):188-95.
Lefranc et al., "IMGT unique numbering for immunoglobulin and T cell receptor variable domains and Ig superfamily V-like domains," Dev Comp Immunol (2003) 27(1):55-77.
Li et al., "Directed evolution of human T-cell receptors with picomolar affinities by phage display", Nat Biotechnol. (2005) 23(3):349-354.
Ling et al., "B-cell and plasma cell antigens: new and previously defined clusters," Leucocyte typing III. (1987) 302-355.
Liu et al., "Inclusion of Strep-tag II in design of antigen receptors for T-cell immunotherapy," Nat Biotechnol (2016) 34(4):430-434.
Lupton et al., "Dominant positive and negative selection using a hygromycin phosphotransferase-thymidine kinase fusion gene," Mol and Cell Biol (1991) 11(6):3374-3378.
Manthey et al., "JNJ-28312141, a novel orally active colony-stimulating factor-1 receptor/FMS-related receptor tyrosine kinase-3 receptor tyrosine kinase inhibitor with potential utility in solid tumors, bone metastases, and acute myeloid leukemia," Mol Cancer Ther (2009) 8(11):3151-3161.
Manuri et al., "piggyBac transposon/transposase system to generate CD19-specific T cells for the treatment of B-lineage malignancies," Hum Gene Ther (2010) 21(4): 427-437.
Mesa et al., "Ruxolitinib," Nature Reviews Drug Disovery (2012) 11(2):103-104.
Miller et al., "Improved retroviral vectors for gene transfer and expression," Biotechniques (1989) 7(9):980-982.
Miller et al., "Retrovirus packaging cells," Human Gene Therapy (1990) 1:5-14.

(56) References Cited

OTHER PUBLICATIONS

Mullen et al., "Transfer of the bacterial gene for cytosine deaminase to mammalian cells confers lethal sensitivity to 5-fluorocytosine: A negative selection system," Proc Natl Acad Sci U.S.A (1992) 89:33-37.
Muller et al., "Amino-substituted thalidomide analogs: Potent inhibitors of TNF-a production," Bioorganic & Medicinal Chemistry Letters (1999) 9(11):1625-1630.
Ohno et al., "A c-fms tyrosine kinase inhibitor, Ki20227, suppresses osteoclast differentiation and osteolytic bone destruction in a bone metastasis model," Mol Cancer Ther (2006) 5(11):2634-2643.
Ozmen et al., "Mouse soluble IFN gamma receptor as IFN gamma inhibitor. Distribution, antigenicity, and activity after injection in mice," J Immunol (1993) 150(7):2698-2705.
Park et al., "Treating cancer with genetically engineered T cells," Trends Biotechnol. (2011) 29(11): 550-557.
Ponomarev et al., "MicroRNA-124 promotes microglia quiescence and suppresses EAE by deactivating macrophages via the C/EBP-α-PU.1 pathway," Nat Med (2011) 17(1):64-70.
Portolano et al., "Lack of promiscuity in autoantigen-specific H and L chain combinations as revealed by human H and L chain "roulette"," J Immunol. (1993) 150:880-887.
Pryer et al., "MCS110: a monoclonal antibody with potent neutralizing activity against macrophage colony-stimulating factor for the treatment of tumor-induced osteolysis," AACR Annual Meeting (2009) Abstract #DDT02-2.
Pyonteck et al., "CSF-1R inhibition alters macrophage polarization and blocks glioma progression," Nat Med (2013) 19(10):1264-1272.
Ramirez et al., "Prevention of Alzheimer's disease pathology by cannabinoids: neuroprotection mediated by blockade of microglial activation," J Neurosci (2005) 25(8):1904-1913.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Ries et al., "Targeting tumor-associated macrophages with anti-CSF-1 R antibody reveals a strategy for cancer therapy," Cancer Cell (2014) 25(6):846-859.
Rosenberg, et al., "Cell transfer immunotherapy for metastatic solid cancer-what clinicians need to know," Nat Rev Clin Oncol. (2011) 8(10):577-585.
Rovida et al., "Colony-Stimulating Factor-1 Receptor in the Polarization of Macrophages: A Target for Turning Bad to Good Ones?" J Clin Cell Immunol (2015) 6:379.
Ruella et al., "Kinase Inhibitor Ibrutinib Prevents Cytokine-Release Syndrome after Anti-CD19 Chimeric Antigen Receptor T Cells (CART) for B Cell Neoplasms," Blood 2016. 128:2159. Presented at ASH 58th Annual Meeting San Diego, CA (Dec. 3-6, 2016).
Sadelain et al., "The basic principles of chimeric antigen receptor design," Cancer Discov. (2013) 3(4): 388-398.
Santomasso et al., "Clinical and Biological Correlates of Neurotoxicity Associated with CAR T-cell Therapy in Patients with B-cell Acute Lymphoblastic Leukemia,"Cancer Discovery (2018) 8(8):958-971.
Sanz et al., "Nimodipine inhibits IL-10 release stimulated by amyloid β from microglia," Br J Pharmacol (2012) 167(8):1702-1711.
Scarpa et al., "Characterization of recombinant helper retroviruses from Moloneybased vectors in ecotropic and amphotropic packaging cell lines," Virology (1991) 180:849-852.
Schlueter et al., "Specificity and binding properties of a single-chain T cell receptor," J Mol Biol. (1996) 256(5):859-69.
Schuler et al., SYFPEITHI, Database for Searching and T-Cell Epitope Prediction. in Immunoinformatics Methods in Molecular Biology, (2007) 409(1): 75-93.
Shahrara et al., "Inhibition of Monocyte Chemoattractant Protein-1 Ameliorates Rat Adjuvant-Induced Arthritis," J Imunol (2008) 180:3447-3456.

Sharma et al., "Efficient sleeping beauty DNA transposition from DNA minicircles," Molec Ther Nucl Acids (2013) 2:e74.
Singh et al., "ProPred: prediction of HLA-DR binding sites," Bioinformatics. (2001) 17(12): 1236-1237.
Smith et al., "Abstract 4889: The highly specific CSF1R inhibitor DCC-3014 exhibits immunomodulatory and anti-invasive activities in cancer models," Cancer Research (2016) 76(14 Supplement):4889.
Soo Hoo et al., "Characterization of a single-chain T-cell receptor expressed in Escherichia coli," Proc Natl Acad Sci U S A. (1992) 89(10): 4759-4763.
Teachey et al., "Biomarkers Accurately Predict Cytokine Release Syndrome (CRS) after Chimeric Antigen Receptor (CAR) T Cell Therapy for Acute Lymphoblastic Leukemia (ALL)," Blood (2015) 126(23):1334.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Tsukahara et al., "CD19 target-engineered T-cells accumulate at tumor lesions in human B-cell lymphoma xenograft mouse models," Biochem Biophys Res Commun (2013) 438(1): 84-89.
Turtle et al. "Biomarkers of Cytokine Release Syndrome and Neurotoxicity after CD19 Car-T Cells and Mitigation of Toxicity By Cell Dose." Abstract #1852. Poster. Presented at ASH, San Diego, CA (Dec. 3, 2016).
Turtle et al., "Biomarkers of Cytokine Release Syndrome and Mitigation of Toxicity by Cell Dose." Blood (2016) 128(22): 1852.
Turtle et al., "Engineered T cells for anti-cancer therapy," Curr. Opin. Immunol. (2012) 24(5): 633-639.
Vagace et al., "Central nervous system chemotoxicity during treatment of pediatric acute lymphoblastic leukemia/lymphoma," Crit Rev Oncol Hematol (2012) 84(2):274-286.
Valera et al., "Lenalidomide reduces microglial activation and behavioral deficits in a transgenic model of Parkinson's disease," J Neuroinflammation (2015) 12:93.
Van Den Neste et al., "Outcome of Patients With Relapsed Diffuse Large B-cell Lymphoma Who Fail Second-Line Salvage Regimens in the International CORAL Study," Bone Marrow Transplant (2016) 51(1): 51-57.
Van Tendeloo et al., "High-level transgene expression in primary human T lymphocytes and adult bone marrow CD34+ cells via electroporation-mediated gene delivery," Gene Therapy (2000) 7(16): 1431-1437.
Verhoeyen et al., "Lentiviral vector gene transfer into human T cells," Methods Mol Biol. (2009) 506: 97-114.
Von Tresckow et al., "An Open-Label, Multicenter, Phase I/II Study of JNJ-40346527, a CSF-1R Inhibitor, in Patients with Relapsed or Refractory Hodgkin Lymphoma," Clin Cancer Res (2015) 21(8):1843-1850.
Wadhwa et al., "Receptor mediated glycotargeting," J. Drug Targeting (1995) 3(2):111-127.
Wang et al., "Phenotypic and functional attributes of lentivirus-modified CD19-specific human CD8+ central memory T cells manufactured at clinical scale," J Immunother (2012) 35(9):689-701.
Wigler et al., "Transfer of purified herpes virus thymidine kinase gene to cultured mouse cells," Cell (1977) 11:223-232.
Winter et al., "Dose-dependent inhibition of demyelination and microglia activation by IVIG," Ann Clin Transl Neurol (2016) 3(11):828-843.
Wu et al., "Adoptive T-cell therapy using autologous tumor-infiltrating lymphocytes for metastatic melanoma: current status and future outlook," Cancer (2012) 18(2): 160-175.
Wulfing et al., "Correctly folded T-cell receptor fragments in the periplasm of Escherichia coli. Influence of folding catalysts," J Mol Biol. (1994) 242(5): 655-69.
Xu et al., "Cytokine release syndrome in cancer immunotherapy with chimeric antigen receptor engineered T cells," Cancer Letters (2014) 343:172-78.

(56) References Cited

OTHER PUBLICATIONS

Younger et al., "Fibromyalgia symptoms are reduced by low-dose naltrexone: a pilot study," Pain Med (2009) 10(4):663-672.
Yrjanheikki et al., "Tetracyclines inhibit microglial activation and are neuroprotective in global brain ischemia," PNAS (1998) 95(26):15769-15774.
Ansell et al., "CD4+ T-cell immune response to large B-cell non-Hodgkin's lymphoma predicts patient outcome," J Clin Oncol (2001) 19(3):720-726.
Feng et al., "Utilizing quantitative immunohitochemistry for relationship analysis of tumor microenvironment of head and neck cancer patients," Journal for Immunotherapy of Cancer (2014) 2 Suppl 3:P258.
MacKall et al., "Latest in Clinical Application of CAR Cell Therapy for B-cell Malignancy and Transplantation," Blood (2015) 126(23):1-2.
Nedergaard et al., "Low density of CD3+, CD4+ and CD8+ cells is associated with increased risk of relapse in squamous cell cervical cancer," Br J Cancer (2007) 97(8):1135-1138.
Stroncek et al., "Myeloid cells in peripheral blood mononuclear cell concentrates inhibit the expansion of chimeric antigen receptor T cells," Cytotherapy (2016) 18(7):893-901.
Turtle et al., "CD19 Car-T cells of defined CD4+:CD8+ composition in adult B cell ALL patients," J Clinical Investigation (2016) 126(6):2123-2138.

* cited by examiner

SEQUENCE LISTING

<160> NUMBER OF SEQ ID NOS: 61

<210> SEQ ID NO 1
<211> LENGTH: 12
<212> TYPE: PRT
<213> ORGANISM: Homo sapiens
<220> FEATURE:
<223> OTHER INFORMATION: Spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: Spacer (IgG4hinge)

<400> SEQUENCE: 2
gaatctaagt acggaccgcc ctgcccccct tgccct                            36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

-continued

```
<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4
```

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

```
<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5
```

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

```
Asp Leu Trp Leu Arg Asp Lys Ala Thr Phe Thr Cys Phe Val Val Gly
                 85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280
```

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

```
Leu Glu Gly Gly Gly Glu Gly Arg Gly Ser Leu Leu Thr Cys Gly Asp
1               5                   10                  15

Val Glu Glu Asn Pro Gly Pro Arg
            20
```

<210> SEQ ID NO 7
<211> LENGTH: 335
<212> TYPE: PRT
<213> ORGANISM: Artificial Sequence
<220> FEATURE:
<223> OTHER INFORMATION: tEGFR

<400> SEQUENCE: 7

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80
```

```
Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 8
<211> LENGTH: 27
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 8

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01
```

```
<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 10
<211> LENGTH: 41
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 11
<211> LENGTH: 41
<212> TYPE: PRT
<213> ORGANISM: Homo sapiens
<220> FEATURE:
<223> OTHER INFORMATION: CD28

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 12
<211> LENGTH: 42
<212> TYPE: PRT
<213> ORGANISM: Homo sapiens
<220> FEATURE:
<223> OTHER INFORMATION: 4-1BB
<300> PUBLICATION INFORMATION:
<308> DATABASE ACCESSION NUMBER: UniProt Q07011.1
<309> DATABASE ENTRY DATE: 1995-02-01

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

-continued

Asp Val Leu Asp Lys Arg Arg Gly Arg Asp Pro Glu Met Gly Gly Lys
                35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16
<211> LENGTH: 9
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 16

Pro Gly Gly Gly Ser Gly Gly Gly Gly
1               5

<210> SEQ ID NO 17
<211> LENGTH: 17
<212> TYPE: PRT
<213> ORGANISM: Artificial Sequence
<220> FEATURE:
<223> OTHER INFORMATION: Linker

<400> SEQUENCE: 17

Gly Ser Ala Asp Asp Ala Lys Lys Asp Ala Ala Lys Lys Asp Gly Lys
1               5                   10                  15

Ser

<210> SEQ ID NO 18
<211> LENGTH: 18
<212> TYPE: PRT
<213> ORGANISM: Artificial Sequence
<220> FEATURE:
<223> OTHER INFORMATION: T2A

<400> SEQUENCE: 18

Glu Gly Arg Gly Ser Leu Leu Thr Cys Gly Asp Val Glu Glu Asn Pro
1               5                   10                  15

Gly Pro

<210> SEQ ID NO 19
<211> LENGTH: 6
<212> TYPE: PRT
<213> ORGANISM: Artificial Sequence
<220> FEATURE:
<223> OTHER INFORMATION: MMP linker

<400> SEQUENCE: 19

Pro Leu Gly Leu Trp Ala
1               5

<210> SEQ ID NO 20
<211> LENGTH: 22
<212> TYPE: PRT

```
<213> ORGANISM: Artificial Sequence
<220> FEATURE:
<223> OTHER INFORMATION: P2A

<400> SEQUENCE: 20

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 21
<211> LENGTH: 19
<212> TYPE: PRT
<213> ORGANISM: Artificial Sequence
<220> FEATURE:
<223> OTHER INFORMATION: P2A

<400> SEQUENCE: 21

Ala Thr Asn Phe Ser Leu Leu Lys Gln Ala Gly Asp Val Glu Glu Asn
1               5                   10                  15

Pro Gly Pro

<210> SEQ ID NO 22
<211> LENGTH: 20
<212> TYPE: PRT
<213> ORGANISM: Artificial Sequence
<220> FEATURE:
<223> OTHER INFORMATION: E2A

<400> SEQUENCE: 22

Gln Cys Thr Asn Tyr Ala Leu Leu Lys Leu Ala Gly Asp Val Glu Ser
1               5                   10                  15

Asn Pro Gly Pro
            20

<210> SEQ ID NO 23
<211> LENGTH: 22
<212> TYPE: PRT
<213> ORGANISM: Artificial Sequence
<220> FEATURE:
<223> OTHER INFORMATION: F2A

<400> SEQUENCE: 23

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 24
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 24
atgcttctcc tggtgacaag ccttctgctc tgtgagttac cacacccagc attcctcctg      60
atccca                                                                66

<210> SEQ ID NO 25
<211> LENGTH: 22
<212> TYPE: PRT
<213> ORGANISM: Artificial Sequence
<220> FEATURE:
```

<223> OTHER INFORMATION: GMCSFR alpha chain signal sequence

<400> SEQUENCE: 25

Met Leu Leu Leu Val Thr Ser Leu Leu Cys Glu Leu Pro His Pro
1               5                   10                  15

Ala Phe Leu Leu Ile Pro
            20

<210> SEQ ID NO 26
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 26

Met Ala Leu Pro Val Thr Ala Leu Leu Leu Pro Leu Ala Leu Leu Leu
1               5                   10                  15

His Ala

<210> SEQ ID NO 27
<211> LENGTH: 375
<212> TYPE: PRT
<213> ORGANISM: Homo sapiens
<220> FEATURE:
<223> OTHER INFORMATION: Human CD14

<400> SEQUENCE: 27

Met Glu Arg Ala Ser Cys Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala
            35                  40                  45

Phe Gln Cys Val Ser Ala Val Glu Val Glu Ile His Ala Gly Gly Leu
        50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
            100                 105                 110

Leu Ala Tyr Ser Arg Leu Lys Glu Leu Thr Leu Glu Asp Leu Lys Ile
        115                 120                 125

Thr Gly Thr Met Pro Pro Leu Pro Leu Glu Ala Thr Gly Leu Ala Leu
130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Cys Glu Gln Val Arg Ala
            180                 185                 190

Phe Pro Ala Leu Thr Ser Leu Asp Leu Ser Asp Asn Pro Gly Leu Gly
        195                 200                 205

Glu Arg Gly Leu Met Ala Ala Leu Cys Pro His Lys Phe Pro Ala Ile
    210                 215                 220

Gln Asn Leu Ala Leu Arg Asn Thr Gly Met Glu Thr Pro Thr Gly Val
225                 230                 235                 240

```
Cys Ala Ala Leu Ala Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Asp Leu
    290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
                340                 345                 350

Ala Arg Ser Thr Leu Ser Val Gly Val Ser Gly Thr Leu Val Leu Leu
                355                 360                 365

Gln Gly Ala Arg Gly Phe Ala
    370                 375

<210> SEQ ID NO 28
<211> LENGTH: 326
<212> TYPE: PRT
<213> ORGANISM: Homo sapiens
<220> FEATURE:
<223> OTHER INFORMATION: Mature human CD14

<400> SEQUENCE: 28

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
            20                  25                  30

Val Ser Ala Val Glu Val Glu Ile His Ala Gly Gly Leu Asn Leu Glu
        35                  40                  45

Pro Phe Leu Lys Arg Val Asp Ala Asp Ala Asp Pro Arg Gln Tyr Ala
    50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
            100                 105                 110

Met Pro Pro Leu Pro Leu Glu Ala Thr Gly Leu Ala Leu Ser Ser Leu
        115                 120                 125

Arg Leu Arg Asn Val Ser Trp Ala Thr Gly Arg Ser Trp Leu Ala Glu
    130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
            180                 185                 190

Leu Met Ala Ala Leu Cys Pro His Lys Phe Pro Ala Ile Gln Asn Leu
        195                 200                 205

Ala Leu Arg Asn Thr Gly Met Glu Thr Pro Thr Gly Val Cys Ala Ala
    210                 215                 220
```

```
Leu Ala Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
                245                 250                 255

Ser Ala Leu Asn Ser Leu Asn Leu Ser Phe Ala Gly Leu Glu Gln Val
            260                 265                 270

Pro Lys Gly Leu Pro Ala Lys Leu Arg Val Leu Asp Leu Ser Cys Asn
        275                 280                 285

Arg Leu Asn Arg Ala Pro Gln Pro Asp Glu Leu Pro Glu Val Asp Asn
    290                 295                 300

Leu Thr Leu Asp Gly Asn Pro Phe Leu Val Pro Gly Thr Ala Leu Pro
305                 310                 315                 320

His Glu Gly Ser Met Asn
                325

<210> SEQ ID NO 29
<211> LENGTH: 18
<212> TYPE: PRT
<213> ORGANISM: Artificial Sequence
<220> FEATURE:
<223> OTHER INFORMATION: Linker

<400> SEQUENCE: 29

Gly Ser Thr Ser Gly Ser Gly Lys Pro Gly Ser Gly Glu Gly Ser Thr
1               5                   10                  15

Lys Gly

<210> SEQ ID NO 30
<211> LENGTH: 735
<212> TYPE: DNA
<213> ORGANISM: Artificial Sequence
<220> FEATURE:
<223> OTHER INFORMATION: scFv

<400> SEQUENCE: 30
gacatccaga tgacccagac cacctccagc ctgagcgcca gcctgggcga ccgggtgacc      60
atcagctgcc gggccagcca ggacatcagc aagtacctga actggtatca gcagaagccc     120
gacggcaccg tcaagctgct gatctaccac accagccggc tgcacagcgg cgtgcccagc     180
cggtttagcg gcgccggctc cggcaccgac tacagcctga ccatctccaa cctggaacag     240
gaagatatcg ccacctactt ttgccagcag ggcaacacac tgccctacac ctttggcggc     300
ggaacaaagc tggaaatcac cggcagcacc tccggcagcg gcaagcctgg cagcggcgag     360
ggcagcacca agggcgaggt gaagctgcag gaaagcggcc ctggcctggt ggcccccagc     420
cagagcctga gcgtgacctg caccgtgagc ggcgtgagcc tgcccgacta cggcgtgagc     480
tggatccggc agcccccag gaagggcctg aatggctgg gcgtgatctg gggcagcgag      540
accacctact acaacagcgc cctgaagagc cggctgacca tcatcaagga caacagcaag     600
agccaggtgt tcctgaagat gaacagcctg cagaccgacg acaccgccat ctactactgc     660
gccaagcact actactacgg cggcagctac gccatggact actggggcca gggcaccagc     720
gtgaccgtga gcagc                                                     735

<210> SEQ ID NO 31
<211> LENGTH: 5
<212> TYPE: PRT
<213> ORGANISM: Artificial Sequence
<220> FEATURE:
```

```
<223> OTHER INFORMATION: Hinge
<220> FEATURE:
<221> NAME/KEY: VARIANT
<222> LOCATION: (1)...(1)
<223> OTHER INFORMATION: Xaa1 = glycine, cysteine or arginine
<220> FEATURE:
<221> NAME/KEY: VARIANT
<222> LOCATION: (4)...(4)
<223> OTHER INFORMATION: Xaa4 = cysteine or threonine

<400> SEQUENCE: 31

Xaa Pro Pro Xaa Pro
1               5

<210> SEQ ID NO 32
<211> LENGTH: 15
<212> TYPE: PRT
<213> ORGANISM: Artificial Sequence
<220> FEATURE:
<223> OTHER INFORMATION: Hinge

<400> SEQUENCE: 32

Glu Pro Lys Ser Cys Asp Lys Thr His Thr Cys Pro Pro Cys Pro
1               5                   10                  15

<210> SEQ ID NO 33
<211> LENGTH: 12
<212> TYPE: PRT
<213> ORGANISM: Artificial Sequence
<220> FEATURE:
<223> OTHER INFORMATION: Hinge

<400> SEQUENCE: 33

Glu Arg Lys Cys Cys Val Glu Cys Pro Pro Cys Pro
1               5                   10

<210> SEQ ID NO 34
<211> LENGTH: 61
<212> TYPE: PRT
<213> ORGANISM: Artificial Sequence
<220> FEATURE:
<223> OTHER INFORMATION: Hinge

<400> SEQUENCE: 34

Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
                20                  25                  30

Pro Lys Ser Cys Asp Thr Pro Pro Pro Cys Pro Arg Cys Pro Glu Pro
        35                  40                  45

Lys Ser Cys Asp Thr Pro Pro Pro Cys Pro Arg Cys Pro
    50                  55                  60

<210> SEQ ID NO 35
<211> LENGTH: 12
<212> TYPE: PRT
<213> ORGANISM: Artificial Sequence
<220> FEATURE:
<223> OTHER INFORMATION: Hinge

<400> SEQUENCE: 35

Glu Ser Lys Tyr Gly Pro Pro Cys Pro Ser Cys Pro
1               5                   10

<210> SEQ ID NO 36
<211> LENGTH: 12
```

```
<212> TYPE: PRT
<213> ORGANISM: Artificial Sequence
<220> FEATURE:
<223> OTHER INFORMATION: Hinge

<400> SEQUENCE: 36

Glu Ser Lys Tyr Gly Pro Pro Cys Pro Pro Cys Pro
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Hinge

<400> SEQUENCE: 37

Tyr Gly Pro Pro Cys Pro Pro Cys Pro
1               5

<210> SEQ ID NO 38
<211> LENGTH: 10
<212> TYPE: PRT
<213> ORGANISM: Artificial Sequence
<220> FEATURE:
<223> OTHER INFORMATION: Hinge

<400> SEQUENCE: 38

Lys Tyr Gly Pro Pro Cys Pro Pro Cys Pro
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Hinge

<400> SEQUENCE: 39

Glu Val Val Val Lys Tyr Gly Pro Pro Cys Pro Pro Cys Pro
1               5                   10

<210> SEQ ID NO 40
<211> LENGTH: 11
<212> TYPE: PRT
<213> ORGANISM: Artificial Sequence
<220> FEATURE:
<223> OTHER INFORMATION: FMC63 CDR L1

<400> SEQUENCE: 40

Arg Ala Ser Gln Asp Ile Ser Lys Tyr Leu Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 41

Ser Arg Leu His Ser Gly Val
1               5

<210> SEQ ID NO 42
<211> LENGTH: 9
<212> TYPE: PRT
```

```
<213> ORGANISM: Artificial Sequence
<220> FEATURE:
<223> OTHER INFORMATION: FMC63 CDR L3

<400> SEQUENCE: 42

Gly Asn Thr Leu Pro Tyr Thr Phe Gly
1               5

<210> SEQ ID NO 43
<211> LENGTH: 5
<212> TYPE: PRT
<213> ORGANISM: Artificial Sequence
<220> FEATURE:
<223> OTHER INFORMATION: FMC63 CDR H1

<400> SEQUENCE: 43

Asp Tyr Gly Val Ser
1               5

<210> SEQ ID NO 44
<211> LENGTH: 16
<212> TYPE: PRT
<213> ORGANISM: Artificial Sequence
<220> FEATURE:
<223> OTHER INFORMATION: FMC63 CDR H2

<400> SEQUENCE: 44

Val Ile Trp Gly Ser Glu Thr Thr Tyr Tyr Asn Ser Ala Leu Lys Ser
1               5                   10                  15

<210> SEQ ID NO 45
<211> LENGTH: 7
<212> TYPE: PRT
<213> ORGANISM: Artificial Sequence
<220> FEATURE:
<223> OTHER INFORMATION: FMC63 CDR H3

<400> SEQUENCE: 45

Tyr Ala Met Asp Tyr Trp Gly
1               5

<210> SEQ ID NO 46
<211> LENGTH: 120
<212> TYPE: PRT
<213> ORGANISM: Artificial Sequence
<220> FEATURE:
<223> OTHER INFORMATION: FMC63 VH

<400> SEQUENCE: 46

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
                100                 105                 110
```

```
Gly Thr Ser Val Thr Val Ser Ser
            115                 120

<210> SEQ ID NO 47
<211> LENGTH: 107
<212> TYPE: PRT
<213> ORGANISM: Artificial Sequence
<220> FEATURE:
<223> OTHER INFORMATION: FMC63 VL

<400> SEQUENCE: 47

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 48
<211> LENGTH: 245
<212> TYPE: PRT
<213> ORGANISM: Artificial Sequence
<220> FEATURE:
<223> OTHER INFORMATION: FMC63 scFv

<400> SEQUENCE: 48

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190
```

```
Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245
```

<210> SEQ ID NO 49
<211> LENGTH: 11
<212> TYPE: PRT
<213> ORGANISM: Artificial Sequence
<220> FEATURE:
<223> OTHER INFORMATION: SJ25C1 CDR L1

<400> SEQUENCE: 49

```
Lys Ala Ser Gln Asn Val Gly Thr Asn Val Ala
1               5                   10
```

<210> SEQ ID NO 50
<211> LENGTH: 7
<212> TYPE: PRT
<213> ORGANISM: Artificial Sequence
<220> FEATURE:
<223> OTHER INFORMATION: SJ25C1 CDR L2

<400> SEQUENCE: 50

```
Ser Ala Thr Tyr Arg Asn Ser
1               5
```

<210> SEQ ID NO 51
<211> LENGTH: 9
<212> TYPE: PRT
<213> ORGANISM: Artificial Sequence
<220> FEATURE:
<223> OTHER INFORMATION: SJ25C1 CDR L3

<400> SEQUENCE: 51

```
Gln Gln Tyr Asn Arg Tyr Pro Tyr Thr
1               5
```

<210> SEQ ID NO 52
<211> LENGTH: 5
<212> TYPE: PRT
<213> ORGANISM: Artificial Sequence
<220> FEATURE:
<223> OTHER INFORMATION: SJ25C1 CDR H1

<400> SEQUENCE: 52

```
Ser Tyr Trp Met Asn
1               5
```

<210> SEQ ID NO 53
<211> LENGTH: 17
<212> TYPE: PRT
<213> ORGANISM: Artificial Sequence
<220> FEATURE:
<223> OTHER INFORMATION: SJ25C1 CDR H2

<400> SEQUENCE: 53

```
Gln Ile Tyr Pro Gly Asp Gly Asp Thr Asn Tyr Asn Gly Lys Phe Lys
1               5                   10                  15

Gly
```

<210> SEQ ID NO 54
<211> LENGTH: 13
<212> TYPE: PRT
<213> ORGANISM: Artificial Sequence
<220> FEATURE:
<223> OTHER INFORMATION: SJ25C1 CDR H3

<400> SEQUENCE: 54

Lys Thr Ile Ser Ser Val Val Asp Phe Tyr Phe Asp Tyr
1               5                   10

<210> SEQ ID NO 55
<211> LENGTH: 122
<212> TYPE: PRT
<213> ORGANISM: Artificial Sequence
<220> FEATURE:
<223> OTHER INFORMATION: SJ25C1 VH

<400> SEQUENCE: 55

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120

<210> SEQ ID NO 56
<211> LENGTH: 108
<212> TYPE: PRT
<213> ORGANISM: Artificial Sequence
<220> FEATURE:
<223> OTHER INFORMATION: SJ25C1 VL

<400> SEQUENCE: 56

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105

<210> SEQ ID NO 57
<211> LENGTH: 15
<212> TYPE: PRT
<213> ORGANISM: Artificial Sequence
<220> FEATURE:
<223> OTHER INFORMATION: Linker

<400> SEQUENCE: 57

Gly Gly Gly Gly Ser Gly Gly Gly Ser Gly Gly Gly Gly Ser
1               5                   10                  15

<210> SEQ ID NO 58
<211> LENGTH: 245
<212> TYPE: PRT
<213> ORGANISM: Artificial Sequence
<220> FEATURE:
<223> OTHER INFORMATION: SJ25C1 scFv

<400> SEQUENCE: 58

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Ser Gly Gly Gly Gly Ser Asp Ile Glu Leu Thr Gln Ser
    130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225                 230                 235                 240

Leu Glu Ile Lys Arg
                245

<210> SEQ ID NO 59
<211> LENGTH: 12
<212> TYPE: PRT
<213> ORGANISM: Artificial Sequence
<220> FEATURE:
<223> OTHER INFORMATION: FMC63 CDR H3

-continued

```
<400> SEQUENCE: 59

His Tyr Tyr Tyr Gly Gly Ser Tyr Ala Met Asp Tyr
1               5                   10

<210> SEQ ID NO 60
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 60

His Thr Ser Arg Leu His Ser
1               5

<210> SEQ ID NO 61
<211> LENGTH: 9
<212> TYPE: PRT
<213> ORGANISM: Artificial Sequence
<220> FEATURE:
<223> OTHER INFORMATION: FMC63 CDR L3

<400> SEQUENCE: 61

Gln Gln Gly Asn Thr Leu Pro Tyr Thr
1               5
```

ARTICLES OF MANUFACTURE AND METHODS RELATED TO TOXICITY ASSOCIATED WITH CELL THERAPY

CROSS-REFERENCE TO RELATED APPLICATIONS

This application is a National Stage application under 35 U.S.C. § 371 of International Application No. PCT/US2018/035752 filed on Jun. 1, 2018, which claims priority from U.S. provisional application No. 62/514,762, filed Jun. 2, 2017, entitled "ARTICLES OF MANUFACTURE AND METHODS RELATED TO TOXICITY ASSOCIATED WITH CELL THERAPY" and U.S. provisional application No. 62/515,526, filed Jun. 5, 2017, entitled "ARTICLES OF MANUFACTURE AND METHODS RELATED TO TOXICITY ASSOCIATED WITH CELL THERAPY," the contents of which are hereby incorporated by reference in their entirety.

INCORPORATION BY REFERENCE OF SEQUENCE LISTING

The present application is being filed along with a Sequence Listing in electronic format. The Sequence Listing is provided as a file entitled 735042012000SeqList.TXT, created Nov. 26, 2019 which is 38,626 bytes in size. The information in the electronic format of the Sequence Listing is incorporated by reference in its entirety.

FIELD

The present disclosure provides methods and articles of manufacture for use with cell therapy for the treatment of diseases or conditions, e.g., cancer, including for predicting and treating a toxicity. In some embodiments, the toxicity is a neurotoxicity or cytokine release syndrome (CRS), such as a severe neurotoxicity or a severe CRS. The methods generally involve detecting a marker by assaying a biological sample from a subject that is a candidate for treatment, optionally with a cell therapy, to determine if the subject is at risk for developing the toxicity, such as neurotoxicity or CRS or severe neurotoxicity or severe CRS. In some embodiments, the methods and articles of manufacture further includes a regent for assaying the biological sample and instructions for determining the percentage or number of cells positive for the marker in the biological sample.

BACKGROUND

Various methods are available for adoptive cell therapy using engineered cells expressing recombinant receptors, such as chimeric antigen receptor (CARs). Improved methods are needed, for example, to increase safety and/or reduce the risk of toxicity in a subject to the administered cells. Provided are methods, compositions, and articles of manufacture that meet such needs.

SUMMARY

Provided herein is an article of manufacture containing a reagent capable of detecting or that is specific for a population of myeloid cells or a marker expressed on a population of myeloid cells, and instructions for using the reagent to assay a biological sample from a subject that is a candidate for treatment, optionally with a cell therapy, said cell therapy optionally containing a dose or composition of genetically engineered cells expressing a recombinant receptor. In some embodiments, the biological sample is an apheresis sample. In some embodiments, the population of cells is or contains monocytes. In some embodiments, the marker is a myeloid cell marker and/or wherein the marker is CD14 and/or wherein the population of cells is or contains CD14+ myeloid cells. In some of any such embodiments, the marker is human, optionally human CD14.

In some embodiments, the marker is a myeloid cell marker, such as a human myeloid cell marker, such as a monocyte marker, e.g., a human monocyte marker. In some aspects, the monocyte marker is a marker present on, e.g., on the surface of, all or most monocytes or most monocyte populations, optionally in a human or in a healthy individual. In some aspects, the monocyte marker is not present on or is not ordinarily expressed on populations of cells other than myeloid cells or other than monocytes, such as is not present on lymphocytes and/or is not expressed on neutrophils. In some aspects, the monocyte marker is a marker that is co-expressed or substantially co-expressed with, or that has a coextensive or essentially coextensive expression pattern, CD14 in human cells and/or has a similar or essentially the same expression pattern as CD14 in humans.

In some of any such embodiments, the reagent is a binding molecule that specifically binds to the marker or cells of the myeloid cell population. In some of any such embodiments, the reagent is an antibody or an antigen-binding fragment thereof.

In some of any such embodiments, the biological sample is or is obtained from a blood, plasma or serum sample. In some examples, the biological sample is or is obtained from an apheresis or leukapheresis sample.

In some of any such embodiments, the article of manufacture further contains the cell therapy and/or further contains instructions for use with, prior to and/or in connection with treatment with the cell therapy. In some of any such embodiments, the article of manufacture further contains one or more agents or treatments for treating, preventing, delaying, reducing or attenuating the development or risk of development of a toxicity and/or instructions for the administration of one or more agents or treatments for treating, preventing, delaying, reducing or attenuating the development or risk of development of a toxicity in the subject. In some embodiments, the toxicity is a neurotoxicity. In some particular embodiments, the neurotoxicity is severe neurotoxicity (e.g., grade 3 or higher neurotoxicity).

In some of any such embodiments, the instructions further specify, if the percentage or number of cells in the sample positive for the marker, and/or percentage or number of cells of the population in the sample, is at or above a threshold level, administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of the cell therapy to the subject; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

In some of any such embodiments, the instructions further specify, if the number or percentage of cells in the sample positive for the marker, and/or percentage or number of cells of the population in the sample, is below a threshold level, administering to the subject the cell therapy, optionally at a non-reduced dose, optionally on an outpatient basis or without admission to the hospital for one or more days. In some of any such embodiments, the instructions further specify administering the cell therapy to the subject and wherein the instructions further specify, if the number or percentage of cells in the sample positive for the marker, and/or percentage or number of cells of the population in the sample, is below a threshold level: the administration of the cell therapy does not include administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

In some of any such embodiments, the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition. In some of any such embodiments, the threshold level is a percent of cells surface positive for the marker in the biological sample or blood or apheresis sample that is or is about 20%, 25%, 30%, 35%, 40%, 45%, 50%, 55% or 60%.

Provided is an article of manufacture containing a cell therapy, said cell therapy optionally containing a dose or composition of genetically engineered cells expressing a recombinant receptor, and instructions for administering the T cell therapy, wherein: (A) the instructions or literature further provide that the administration is carried out following or based on the results of an assessment, in a biological sample, of the presence or percentage or number of cells of a myeloid cell population or of a level of expression of a marker expressed by cells of said population or of a myeloid marker, optionally said biological sample obtained from the subject prior to administering the cell therapy and/or said biological sample not comprising the recombinant receptor and/or said engineered cells; and/or (B) the instructions or literature further specify one or more specific aspects of the treatment or carrying out one or more interventions to be carried out in association with the administration, optionally based on a parameter assessed in a biological sample from the subject and/or an assessed level of risk of developing a toxicity or toxic outcome following administration of the cell therapy, wherein (i) the parameter is or comprises the presence or percentage or number of cells of a myeloid cell population or of a level of expression of a marker expressed by cells of said population or of a myeloid marker or (ii) the assessed level of risk is based on the presence or percentage or number of cells of a myeloid cell population or of a level of expression of a marker expressed by cells of said population or of a myeloid marker, in a cell, sample, or tissue of the subject.

In some embodiments of the article of manufacture described, the further specifying in (B) includes specifying administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of administration of the therapeutic cell composition or the genetically engineered cells; and/or specifying administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or specifying administering to the subject the cell therapy in an in-patient setting and/or with admission to the hospital for one or more days, optionally wherein the cell therapy is otherwise to be administered to subjects on an outpatient basis or without admission to the hospital for one or more days. In some embodiments, the instructions further specify the level of the parameter or assessed risk.

In some aspects, the assessment in (A) includes detection which optionally includes contacting a reagent capable of directly or indirectly detecting myeloid cells or a marker expressed on a population of myeloid cells with the biological sample and determining the percentage or number of cells positive for, optionally surface positive for, the marker and/or level in the biological sample.

In some embodiments, the population of cells is or contains monocytes. In some examples, the marker is a myeloid cell marker and/or wherein the marker is CD14 and/or wherein the population of cells is or contains CD14+ myeloid cells. In some aspects, the marker is human, optionally human CD14.

In some of any such embodiments, the reagent is a binding molecule that specifically binds to the marker or cells of the myeloid cell population. In some embodiments, the reagent is an antibody or an antigen-binding fragment thereof.

In some of any such embodiments, the biological sample is or is obtained from a blood, plasma or serum sample. In some examples, the biological sample is or is obtained from an apheresis or leukapheresis sample.

In some of any such embodiments, the article of manufacture further contains the reagent for detecting myeloid cells or a marker expressed on a population of myeloid cells and/or further containing instructions for use with, prior to and/or in connection with the reagent for detecting myeloid cells or a marker expressed on a population of myeloid cells. In some of any such embodiments, the article of manufacture further contains one or more agents or treatments for treating, preventing, delaying, reducing or attenuating the development or a risk of development of a toxicity and/or instructions for the administration of one or more agents or treatments for treating, preventing, delaying, reducing or attenuating the development or risk of development of a toxicity in the subject.

In some of any such embodiments, the instructions for administering the cell therapy specify, if the percentage or number of cells in the sample positive for the marker and/or percentage or number of cells of the population in the sample, is at or above a threshold level: administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of administration of the therapeutic cell composition or the genetically engineered cells; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

In some of any such embodiments, the instructions for administering the cell therapy specify, if the number or percentage of cells in the sample positive for the marker, and/or percentage or number of cells of the population in the sample, is below a threshold level, administering to the subject the cell therapy, optionally at a non-reduced dose, optionally on an outpatient basis or without admission to the hospital for one or more days. In some embodiments, the instructions further specify administering the cell therapy to the subject and wherein the instructions further specify, if the number or percentage of cells in the sample positive for the marker, and/or percentage or number of cells of the population in the sample, is below a threshold level: not administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

In some of any such embodiments, the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition. In some embodiments, the threshold level is a percent of cells surface positive for the marker in the biological sample or blood or apheresis sample that is or is about 20%, 25%, 30%, 35%, 40%, 45%, 50%, 55% or 60%.

Provided is an article of manufacture containing an agent capable of treating, preventing, delaying, reducing or attenuating the development or risk of development of a toxicity, and instructions for administering the agent following or based on the results of an assessment in a biological sample of the presence or percentage or number of cells of a myeloid cell population or of a level of expression of a marker expressed by cells of said population or of a myeloid marker. In some embodiments, the assessment includes detection which optionally includes contacting a reagent capable of directly or indirectly detecting myeloid cells or a marker expressed on a population of myeloid cells s with the biological sample and determining the percentage or number of cells positive for, optionally surface positive for, the myeloid marker and/or level in the biological sample.

In some of any such embodiments, the instructions specify that the agent is to be administered (i) prior to, (ii) within one, two, or three days of, (iii) concurrently with and/or (iv) at first fever following, the initiation of administration of the cell therapy to the subject and/or further contains instructions for use with, prior to and/or in connection with treatment with the cell therapy.

In some of any such embodiments, the biological sample is obtained from the subject prior to administering the agent or cell therapy. In some embodiments, the population of cells is or contains monocytes. In some embodiments, the marker is a myeloid cell marker and/or wherein the marker is CD14 and/or wherein the population of cells is or contains CD14+ myeloid cells. In some embodiments, the marker is human, optionally human CD14.

In some of any such embodiments, the reagent is a binding molecule that specifically binds to the marker or cells of the myeloid cell population. In some embodiments, the reagent is an antibody or an antigen-binding fragment thereof.

In some of any such embodiments, the biological sample is or is obtained from a blood, plasma or serum sample. In some examples, the biological sample is or is obtained from an apheresis or leukapheresis sample.

In some of any such embodiments, the articles of manufacture further contains the reagent for detecting myeloid cells or a marker expressed on a population of myeloid cells and/or further contains instructions for use with, prior to and/or in connection with the reagent for detecting myeloid cells or a marker expressed on a population of myeloid cells. In some embodiments, the articles of manufacture further contains the cell therapy and/or further contains instructions for use with, prior to and/or in connection with treatment with the cell therapy.

In some embodiments, the instructions for administering the agent specify, if the percentage or number of cells in the sample positive for the marker and/or percentage or number of cells of the population in the sample, is at or above a threshold level administering to the subject the agent. In some cases, the instruction further specify administering a cell therapy to the subject, wherein administration of the agent is to be carried out (i) prior to, (ii) within one, two, or three days of, (iii) concurrently with and/or (iv) at first fever following, the initiation of administration of the cell therapy to the subject.

In some of any such embodiments, the instructions for administering the agent specify, if the percentage of cells positive in the sample for the marker is below the threshold level administering to the subject the cell therapy, optionally wherein the instructions specify the cell therapy is to be or may be administered to the subject on an outpatient setting and/or without admission of the subject to the hospital overnight or for one or more consecutive days and/or is without admission of the subject to the hospital for one or more days.

In some of any such embodiments, the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition. In some embodiments, the threshold level is a percent of cells surface positive for the myeloid marker in the biological sample or blood or apheresis that is or is about 20%, 25%, 30%, 35%, 40%, 45%, 50%, 55% or 60%. In some of any such embodiments, the assaying or assessing cells myeloid cells or a marker expressed on a population of myeloid cells includes flow cytometry.

In some of any such embodiments, the toxicity includes neurotoxicity or cytokine release syndrome (CRS), optionally grade 1 or higher neurotoxicity or CRS. In some cases, the toxicity includes severe neurotoxicity and/or includes a grade 2 or higher neurotoxicity, a grade 3 or higher neurotoxicity, at least prolonged grade 3 neurotoxicity or is at or above grade 4 or grade 5 neurotoxicity; and/or the toxicity includes severe CRS and/or includes grade 2 or higher or grade 3 or higher CRS. In some examples, the toxicity is associated with cerebral edema.

In some of any such embodiments, the agent or other treatment is or includes one or more of a steroid; an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function. In some cases, the antagonist or inhibitor is or contains an agent selected from among an antibody or antigen-binding fragment, a small molecule, a protein or peptide and a nucleic acid. In some embodiments, the agent or other treatment is an anti-IL-6 antibody or an anti-IL6 receptor antibody.

In some of any such embodiments, the agent or other treatment is or contains an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101. In some embodiments, the agent or other treatment is or contains tocilizumab. In some embodiments, the agent or other treatment is or contains siltuximab. In some examples, the steroid is or includes dexamethasone.

In some of any such embodiments, the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155) or upregulates microRNA-124 (miR-124). In some aspects, the agent capable of preventing, blocking or reducing microglial cell activation or function is a small molecule, peptide, protein, antibody or antigen-binding fragment thereof, an antibody mimetic, an aptamer, or a nucleic acid molecule. In some examples, the agent is selected from minocycline, naloxone, nimodipine, Riluzole, MOR103, lenalidomide, a cannabinoid (optionally WIN55 or 212-2), intravenous immunoglobulin (IVIg), ibudilast, anti-miR-155 locked nucleic acid (LNA), MCS110, PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945, emactuzumab, IMC-CS4, FPA008, LY-3022855, AMG-820 and TG-3003.

In some embodiments, the agent is an inhibitor of colony stimulating factor 1 receptor (CSF1R). In some aspects, the inhibitor is selected from: PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof; emactuzumab, IMC-CS4, FPA008, LY-3022855, AMG-820 and TG-3003 or is an antigen-binding fragment thereof; or a combination of any of the foregoing. In some specific examples, the inhibitor is PLX-3397.

In some of any such embodiments, the recombinant receptor specifically binds to an antigen associated with the disease or condition or expressed in cells of the environment of a lesion associated with the disease or condition. In some embodiments, the disease or condition is a cancer. In some embodiments, the disease or condition is a myeloma, leukemia or lymphoma. In some examples, the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

In some of any such embodiments, the antigen is or includes B cell maturation antigen (BCMA), carbonic anhydrase 9 (CA9, also known as G250 or CAIX), Her2/neu (receptor tyrosine kinase erb-B2), CD19, CD20, CD22, and hepatitis B surface antigen, anti-folate receptor, CD23, CD24, CD30, CD33, CD38, CD44, chondroitin sulfate proteoglycan 4 (CSPG4), epidermal growth factor protein (EGFR), epithelial glycoprotein 2 (EPG-2), epithelial glycoprotein 40 (EPG-40), ephrinB2, ephrin receptor A2 (EPHa2), Her3 (erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, glypican-3 (GPC3), G Protein Coupled Receptor 5D (GPCR5D), Human high molecular weight-melanoma-associated antigen (HMW-MAA), IL-22 receptor alpha(IL-22Rα or IL-22R-alpha), IL-13 receptor alpha 2 (IL-13Rα2 or IL-13R-alpha2), kinase insert domain receptor (kdr), kappa light chain, Leucine Rich Repeat Containing 8 Family Member A (LRRC8A), Lewis Y, L1-cell adhesion molecule (L1-CAM), Melanoma-associated antigen (MAGE)-A1, MAGE-A3, MAGE-A6, MAGE-A10, Preferentially expressed antigen of melanoma (PRAME), survivin, TAG72, B7-H3, B7-H6, IL-13 receptor alpha 2 (IL-13Rα2), CD171, Human leukocyte antigen A1 (HLA-A1), Human leukocyte antigen A2 (HLA-A2), folate receptor-alpha, CD44v6, CD44v7/8, αvβ6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, dual antigen, a cancer-testes antigen, mesothelin (MSLN), murine cytomegalovirus (CMV), mucin 1 (MUC1), MUC16, prostate specific antigen, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), oncofetal antigen, Receptor Tyrosine Kinase Like Orphan Receptor 1 (ROR1), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific or pathogen-expressed antigen.

In some of any such embodiments, the recombinant receptor is a T cell receptor or a functional non-T cell receptor. In some embodiments, the recombinant receptor is a chimeric antigen receptor (CAR). In some cases, the CAR contains an extracellular antigen-recognition domain that specifically binds to the antigen and an intracellular signaling domain containing an ITAM, wherein optionally, the intracellular signaling domain contains an intracellular domain of a CD3-zeta (CD3ξ) chain; and/or wherein the CAR further contains a costimulatory signaling region, which optionally contains a signaling domain of CD28 or 4-1BB.

In some of any such embodiments, the engineered cells include T cells, optionally CD4+ and/or CD8+. In some cases, the T cells are primary T cells obtained from a subject.

In some of any such embodiments, the dose that is not associated with risk of developing toxicity or severe toxicity is or contains less than or less than about $5 \times 10^7$ total recombinant receptor-expressing cells, optionally CAR+ cells, total T cells, or total peripheral blood mononuclear cells (PBMCs), such as less than or less than about $2.5 \times 10^7$, less than or less than about $1.0 \times 10^7$, less than or less than about $5.0 \times 10^6$, less than or less than about $1.0 \times 10^6$, less than or less than about $5.0 \times 10^5$, or less than or less than about $1 \times 10^5$ total recombinant receptor-expressing cells, optionally CAR+ cells, total T cells, or total peripheral blood mononuclear cells (PBMCs). In some embodiments, the dose that is not associated with risk of developing toxicity or severe toxicity is or contains from or from about $1 \times 10^5$ to $5 \times 10^7$ total recombinant receptor-expressing cells, optionally CAR+ cells, total T cells, or total peripheral blood mononuclear cells (PBMCs), such as $1 \times 10^5$ to $2.5 \times 10^7$, $1 \times 10^5$ to $1.0 \times 10^7$, $1 \times 10^5$ to $5.0 \times 10^6$, $1 \times 10^5$ to $1.0 \times 10^6$, $1.0 \times 10^5$ to $5.0 \times 10^5$, $5.0 \times 10^5$ to $5 \times 10^7$, $5 \times 10^5$ to $2.5 \times 10^7$, $5 \times 10^5$ to $1.0 \times 10^7$, $5 \times 10^5$ to $5.0 \times 10^6$, $5 \times 10^5$ to $1.0 \times 10^6$, $1.0 \times 10^6$ to $5 \times 10^7$, $1 \times 10^6$ to $2.5 \times 10^7$, $1 \times 10^6$ to $1.0 \times 10^7$, $1 \times 10^6$ to $5.0 \times 10^6$, $5.0 \times 10^6$ to $5 \times 10^7$, $5 \times 10^6$ to $2.5 \times 10^7$, $5 \times 10^6$ to $1.0 \times 10^7$, $1.0 \times 10^7$ to $5 \times 10^7$, $1 \times 10^7$ to $2.5 \times 10^7$ or $2.5 \times 10^7$ to $5 \times 10^7$ total recombinant receptor-expressing cells, optionally CAR+ cells, total T cells, or total peripheral blood mononuclear cells (PBMCs).

In some of any such embodiments, the reagent is detectably labeled, optionally fluorescently labeled.

Also provided is a method of selecting a subject for treatment, the method including (a) contacting a biological sample with a reagent capable of detecting or that is specific for a population of myeloid cells or a marker expressed on a population of myeloid cells or cells positive for expression of a myeloid marker, wherein the biological sample is from a subject that is a candidate for treatment with a cell therapy, said cell therapy optionally containing composition comprising a dose of genetically engineered cells expressing a recombinant receptor; and the biological sample is obtained from the subject prior to administering the cell therapy and/or said biological sample does not include the recombinant receptor and/or said engineered cells; and (b) selecting for treatment a subject in which either (i) the percentage or number of cells in the sample positive for the marker, and/or percentage or number of cells of the population in the sample, is at or above a threshold level, thereby identifying a subject that is at risk for developing a toxicity to the cell therapy; or (ii) the percentage or number of cells in the sample positive for the marker, and/or percentage or number of cells of the population in the sample, is below a threshold level. In some embodiments, the biological sample is an apheresis sample. In some embodiments, the toxicity is neurotoxicity.

In some aspects, a subject in which the percentage or number of cells in the sample positive for the marker, and/or percentage or number of cells of the population in the sample, is at or above a threshold level, is selected for administering to the subject (1) an agent or other treatment capable of treating, preventing, delaying, reducing or attenuating the development or risk of development of a toxicity and (2) the cell therapy, wherein administration of the agent is to be administered prior to, within one, two, or three days of, concurrently with and/or at first fever following, the initiation of administration of the cell therapy to the subject; and/or a subject in which the percentage or number of cells in the sample positive for the marker, and/or percentage or number of cells of the population in the sample, is at or above a threshold level, is selected for administering to the subject a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or a subject in which the percentage or number of cells in the sample positive for the marker, and/or percentage or number of cells of the population in the sample, is at or above a threshold level, is selected for administering to the subject a cell therapy in an in-patient setting and/or with admission to the hospital for one or more days, optionally wherein the cell therapy is otherwise to be administered to subjects on an outpatient basis or without admission to the hospital for one or more days.

In some embodiments, subject in which the percentage or number of cells in the sample positive for the marker, and/or percentage or number of cells of the population in the sample, is at or above a threshold level, is selected, and the method further includes administering to the subject (1) an agent or other treatment capable of treating, preventing, delaying, reducing or attenuating the development or risk of development of a toxicity and (2) the cell therapy, wherein administration of the agent is carried out prior to, within one, two, or three days of, concurrently with and/or at first fever following, the initiation of administration of the cell therapy to the subject; and/or administering to the subject a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject a cell therapy or a dose of genetically engineered cells of a cell therapy that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject a cell therapy in an in-patient setting and/or with admission to the hospital for one or more days, optionally wherein the cell therapy is otherwise to be administered to subjects on an outpatient basis or without admission to the hospital for one or more days.

In some embodiments, a subject in which the percentage or number of cells in the sample positive for the marker, and/or percentage or number of cells of the population in the sample, is below a threshold level is selected for: administering to the subject a cell therapy, optionally at a non-reduced dose, optionally on an outpatient basis or without admission to the hospital for one or more days; administering to the subject a cell therapy, wherein the cell therapy does not include administering, prior to or concurrently with administering the cell therapy and/or prior to the development of a sign or symptom of a toxicity other than fever, an agent or treatment capable of treating, preventing, delaying, or attenuating the development of the toxicity; and/or administering a cell therapy on an outpatient setting and/or without admission of the subject to the hospital overnight or for one or more consecutive days and/or is without admission of the subject to the hospital for one or more days.

In some embodiments, a subject in which the percentage or number of cells in the sample positive for the marker, and/or percentage or number of cells of the population in the sample, is below a threshold level is selected, and the method further includes administering to the subject the cell therapy, optionally at a non-reduced dose, optionally on an outpatient basis or without admission to the hospital for one or more days. In some examples, a subject in which the percentage or number of cells in the sample positive for the marker, and/or percentage or number of cells is selected, and the method further includes administering to the subject the cell therapy, wherein the administration of the cell therapy does not include administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

Provided is a method of treatment including assaying a biological sample for the presence or percentage or number of cells of a myeloid cell population or of a level of expression of a marker expressed by cells of said population or of a myeloid marker, wherein the biological sample is from a subject that is a candidate for treatment, optionally with a cell therapy, said cell therapy optionally containing a dose or composition of genetically engineered cells expressing a recombinant receptor for treating a disease or condition; and following or based on the results of the assay, administering to the subject the cell therapy, and, optionally, an agent or other treatment capable of treating, preventing, delaying, reducing or attenuating the development or risk of development of a toxicity.

Also provided is a method of treatment, including following or based on the results of an assay, of a biological sample from a subject, for the presence or percentage or number of cells of a myeloid cell population or of a level of expression of cells positive for a marker expressed by cells of said population or positive for expression of a myeloid marker, administering to the subject (i) a cell therapy, optionally including a dose or composition of genetically engineered cells expressing a recombinant receptor for treating a disease or condition in the subject, and, optionally, (ii) an agent or other treatment capable of treating, preventing, delaying, reducing or attenuating the development or risk of development of a toxicity, wherein the biological sample is obtained from the subject prior to administering the cell therapy. In some embodiments, the assaying includes detection which optionally includes contacting the sample with a reagent capable of directly or indirectly detecting myeloid cells or a marker expressed on a population of myeloid cells with the biological sample and determining the percentage or number of cells positive for, optionally surface positive for, the myeloid marker and/or level in the biological sample and/or percentage or number of cells of the population of myeloid cells.

In some embodiments, if the percentage or number of cells in the sample positive for the marker, and/or percentage or number of cells of the population in the sample, is at or above a threshold level: administering to the subject the agent or other treatment capable of treating, preventing, delaying, reducing or attenuating the development or risk of development of a toxicity prior to, within one, two, or three days of, concurrently with and/or at first fever following, the initiation of administration of the cell therapy to the subject; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

In some embodiments, if the percentage or number or percentage of cells in the sample positive for the marker, and/or percentage or number of cells of the population in the sample, is at or above a threshold level: the administration of the cell therapy does not include administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

Provided herein is a method of assessing a risk of neurotoxicity including assaying an apheresis sample from a subject for the presence or percentage or number of cells of a myeloid cell population or of cells positive for a marker expressed by cells of said population or positive for expression of a myeloid marker; and following or based on the results of the assay, determining if the subject is at risk of developing neurotoxicity or severe neurotoxicity following administration of a cell therapy, said cell therapy comprising a composition comprising a dose of genetically engineered cells expressing a recombinant receptor for treating a disease or condition in the subject, wherein the subject is a candidate for treatment with the cell therapy and the apheresis sample is obtained from the subject prior to administering the cell therapy and/or said apheresis sample does not comprise the recombinant receptor and/or said engineered cells. In some embodiments, the subject is assessed as at risk of developing neurotoxicity or severe neurotoxicity if the percentage or number of cells in the sample positive for the myeloid marker, and/or percentage or number of cells of the population of myeloid cells in the sample, is at or above a threshold level. In some aspects, if the subject is assessed as at risk of developing neurotoxicity or severe neurotoxicity, the method further includes monitoring the subject after administration of the cell therapy for development of a sign or symptom of a neurotoxicity other than fever; administering to the subject the agent or other treatment capable of treating, preventing, delaying, reducing or attenuating the development or risk of development of a neurotoxicity (i) prior to, (ii) within one, two, or three days of, (iii) concurrently with and/or (iv) at first fever following, the initiation of administration of the cell therapy to the subject; administering to the subject the cell therapy at a reduced dose or at a dose that is not associated with risk of developing neurotoxicity or severe neurotoxicity, or is not associated with a risk of developing a neurotoxicity or severe neurotoxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

In some embodiments, the subject is assessed as not suspected to be at risk or as not likely to be at risk of developing neurotoxicity or severe neurotoxicity if the percentage or number of cells in the sample positive for the marker, and/or percentage or number of cells of the population of myeloid cells in the sample, is below a threshold level. In some embodiments, if the subject is assessed as not suspected, or not likely, to be at risk of developing neurotoxicity or severe neurotoxicity, the subject is not further administered, prior to or concurrently with administering the cell therapy and/or prior to the development of a sign or symptom of a neurotoxicity other than fever, an agent or treatment capable of treating, preventing, delaying, or attenuating the development of the neurotoxicity; or the method further includes administering the cell therapy to the subject on an outpatient setting and/or without admission of the subject to the hospital overnight or for one or more consecutive days and/or is without admission of the subject to the hospital for one or more days.

Provided herein is a method of monitoring a subject following administration of a cell therapy, the method includes observing a subject administered a cell therapy for the development of a sign or symptom of a neurotoxicity or severe neurotoxicity other than fever, wherein the subject is one that has been determined to be at risk of, or likely to be at risk of, developing neurotoxicity or severe neurotoxicity as determined based on assaying the presence or percentage or number of cells of a myeloid cell population or of cells positive for a marker expressed by cells of said population or positive for expression of a myeloid marker at or above a threshold level in an apheresis sample, said apheresis sample having been obtained from the subject prior to the administration of the cell therapy and/or said apheresis sample not comprising the recombinant receptor and/or said engineered cells, wherein the cell therapy contains a composition comprising a dose of genetically engineered cells expressing a recombinant receptor for treating a disease or condition in the subject. In some embodiments, the subject has been administered the cell therapy in an in-patient setting and/or with admission to the hospital for one or more days or is admitted to the hospital during the period or a portion of the period of the observation, optionally wherein the cell therapy is otherwise to be administered to subjects on an outpatient basis or without admission to the hospital for one or more days in the absence of the subject being determined to be at risk.

Provided is a method of prophylactic treatment, including administering, to a subject, an agent or other treatment capable of treating, preventing, delaying, reducing or attenuating the development or risk of development of a toxicity, wherein the subject is a candidate for treatment optionally with a cell therapy, said cell therapy optionally containing a dose or composition of genetically engineered cells expressing a recombinant receptor for treating a disease or condition; and the subject has been identified as at risk for developing a toxicity following or based on the results of an assay, of a biological sample from a subject, for the presence or percentage or number of cells of a myeloid cell population or of a level of expression of a marker expressed by cells of said population or of a myeloid marker, said biological sample obtained from the subject prior to administering the cell therapy and/or said biological sample not containing the recombinant receptor and/or said engineered cells. In some embodiments, the biological sample is an apheresis sample. In some embodiments, the toxicity is a neurotoxicity.

In some instances, the assay includes detection which optionally includes contacting a reagent capable of directly or indirectly detecting myeloid cells or a marker expressed on a population of myeloid cells with the biological sample and determining the percentage or number of cells positive, optionally surface positive, for the marker and/or level in the biological sample. In some embodiments, the agent is administered to the subject if the percentage or number of cells in the sample positive for the marker, and/or percentage or number of cells of the population in the sample, is at or above a threshold level.

In some embodiments, the agent is administered prior to, within one, two, or three days of, concurrently with and/or at first fever following, the initiation of administration of the cell therapy to the subject.

In some embodiments, the threshold level is within 25%, within 20%, within 15%, within 10% or within 5% of the average or mean percent or number, and/or is within a standard deviation of the average or mean percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition. In some embodiments, the threshold level is a percent of cells surface positive for the marker in the biological sample or blood or apheresis sample that is or is about 20%, 25%, 30%, 35%, 40%, 45%, 46%, 47%, 48%, 49%, 50%, 51%, 52%, 53%, 54%, 55%, 56%, 57%, 58%, 59% or 60%.

In some embodiments, the percentage is a percentage of the myeloid cell population or of cells positive for the myeloid marker among total leukocytes or total CD45+ cells, or viable cells thereof, in the sample or is a percentage of the myeloid cell population or cells positive for the myeloid marker among total leukocytes or CD45+ cells, or viable cells thereof, in the sample. In some cases, the biological sample is an apheresis sample. In some further embodiments, the apheresis sample is a leukapheresis sample. In some such embodiments, the percentage is a percentage of cells surface positive for CD14 or surface positive for another monocyte marker among total leukocytes or total CD45+ cells, or viable cells thereof, in the sample. In some embodiments, the monocyte marker is a marker present on all or most monocytes of a monocyte population, e.g. in a human, or that is not ordinarily expressed on populations of cells other than myeloid cells or other than monocytes, such as is not present on lymphocytes and/or is not expressed on neutrophils. In some aspects, the monocyte marker is a marker that is co-expressed or substantially co-expressed with, or that has a coextensive or essentially coextensive expression pattern, CD14 in human cells and/or has a similar or essentially the same expression pattern as CD14 in humans.

In some of any such embodiments, the population of cells (e.g. myeloid cells) is or contains monocytes. In some embodiments, the marker is a myeloid cell marker and/or wherein the marker is CD14 and/or wherein the population of cells is or contains CD14+ myeloid cells. In some aspects, the marker is human, optionally human CD14. In some embodiments, the myeloid marker is CD14 or the myeloid cell population is CD14+ and the percentage is a percentage of CD14+ cells among total viable leukocytes or total viable CD45+ cells in the sample. In some examples, the threshold level is a percentage of CD14+ cells among total viable leukocytes or total viable CD45+ cells in the apheresis sample, wherein the percentage is or is about 45%, 46%, 47%, 48%, 49%, 50%, 51%, 52%, 53%, 54%, 55%, 56%, 57%, 58%, 59% or 60%.

In some embodiments, the reagent is a binding molecule that specifically binds to the marker or cells of the myeloid cell population. In some embodiments, the reagent is an antibody or an antigen-binding fragment thereof. In some embodiments, the biological sample is or is obtained from a blood, plasma or serum sample. In some examples, the biological sample is or is obtained from an apheresis or leukapheresis sample. In some embodiments, the assaying or assessing cells myeloid cells or a marker expressed on a population of myeloid cells includes flow cytometry.

Provided herein is a method of monitoring a subject including monitoring a subject after administration of the cell therapy for development of a sign or symptom of a neurotoxicity other than fever, wherein the subject has been assessed for a risk of neurotoxicity and the results of the assessment of an apheresis sample from the subject indicates that the percentage of live leukocytes positive for CD14 is at or above a threshold level, wherein the subject is a candidate for treatment optionally with a cell therapy, said cell therapy optionally comprising a dose or composition of genetically engineered cells expressing a recombinant receptor for treating a disease or condition. In some embodiments, the method further includes administering to the subject an agent or other treatment capable of treating, preventing, delaying, reducing or attenuating the development or risk of development of a neurotoxicity (i) prior to, (ii) within one, two, or three days of, (iii) concurrently with and/or (iv) at first fever following, the initiation of administration of the cell therapy to the subject; administering to the subject the cell therapy at a reduced dose or at a dose that is not associated with risk of developing neurotoxicity or severe neurotoxicity, or is not associated with a risk of developing a neurotoxicity or severe neurotoxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days. In some cases, the CD14 is human CD14.

In some embodiments, the assay includes detection which optionally includes contacting a reagent capable of directly or indirectly detecting CD14 and determining the percentage or number of cells positive, optionally surface positive, for CD14 in the apheresis sample. In some instances, the reagent is a binding molecule that specifically binds to CD14. In some embodiments, the reagent is an antibody or an antigen-binding fragment thereof.

In some of any such embodiments, the toxicity includes neurotoxicity or cytokine release syndrome (CRS), optionally grade 1 or higher neurotoxicity or CRS. In some aspects, the toxicity includes severe neurotoxicity and/or includes a grade 2 or higher neurotoxicity, a grade 3 or higher neurotoxicity, at least prolonged grade 3 neurotoxicity or is at or above grade 4 or grade 5 neurotoxicity; and/or the toxicity includes severe CRS and/or includes grade 2 or higher or grade 3 or higher CRS. In some embodiments, the neurotoxicity is severe neurotoxicity or is a grade 3 or higher neurotoxicity. In some cases, the toxicity is associated with cerebral edema.

In some of any such embodiments, the agent or other treatment is or includes one or more of a steroid; an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function. In some cases, the antagonist or inhibitor is or contains an agent selected from among an antibody or antigen-binding fragment, a small molecule, a protein or peptide and a nucleic acid.

In some embodiments, the agent or other treatment is an anti-IL-6 antibody or an anti-IL6 receptor antibody. In some examples, the agent or other treatment is or contains an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101. In some embodiments, the agent or other treatment is or contains tocilizumab. In some aspects, the agent or other treatment is or contains siltuximab. In some instances, the steroid is or contains dexamethasone.

In some embodiments, the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155) or upregulates microRNA-124 (miR-124). In some cases, the agent capable of preventing, blocking or reducing microglial cell activation or function is a small molecule, peptide, protein, antibody or antigen-binding fragment thereof, an antibody mimetic, an aptamer, or a nucleic acid molecule. In some embodiments, the agent is selected from minocycline, naloxone, nimodipine, Riluzole, MOR103, lenalidomide, a cannabinoid (optionally WIN55 or 212-2), intravenous immunoglobulin (IVIg), ibudilast, anti-miR-155 locked nucleic acid (LNA), MCS110, PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945, emactuzumab, IMC-CS4, FPA008, LY-3022855, AMG-820 and TG-3003.

In some embodiments, the agent is an inhibitor of colony stimulating factor 1 receptor (CSF1R). In some embodiments, the inhibitor is selected from: PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof; emactuzumab, IMC-CS4, FPA008, LY-3022855, AMG-820 and TG-3003 or is an antigen-binding fragment thereof; or a combination of any of the foregoing. In some specific examples, the inhibitor is PLX-3397.

In some of any such embodiments, the recombinant receptor specifically binds to an antigen associated with the disease or condition or expressed in cells of the environment of a lesion associated with the disease or condition. In some aspects, the disease or condition is a cancer. In some cases, the disease or condition is a myeloma, leukemia or lymphoma. In some examples, the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the recombinant receptor specifically binds an antigen associated with, or expressed or present on cells of, the disease or condition.

In some of any such embodiments, the antigen is or includes B cell maturation antigen (BCMA), carbonic anhydrase 9 (CA9, also known as G250 or CAIX), Her2/neu (receptor tyrosine kinase erb-B2), CD19, CD20, CD22, and hepatitis B surface antigen, anti-folate receptor, CD23, CD24, CD30, CD33, CD38, CD44, chondroitin sulfate proteoglycan 4 (CSPG4), epidermal growth factor protein (EGFR), epithelial glycoprotein 2 (EPG-2), epithelial glycoprotein 40 (EPG-40), ephrinB2, ephrin receptor A2 (EPHa2), Her3 (erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, glypican-3 (GPC3), G Protein Coupled Receptor 5D (GPCR5D), Human high molecular weight-melanoma-associated antigen (HMW-MAA), IL-22 receptor alpha(IL-22Rα or IL-22R-alpha), IL-13 receptor alpha 2 (IL-13Rα2 or IL-13R-alpha2), kinase insert domain receptor (kdr), kappa light chain, Leucine Rich Repeat Containing 8 Family Member A (LRRC8A), Lewis Y, L1-cell adhesion molecule (L1-CAM), Melanoma-associated antigen (MAGE)-A1, MAGE-A3, MAGE-A6, MAGE-A10, Preferentially expressed antigen of melanoma (PRAME), survivin, TAG72, B7-H3, B7-H6, IL-13 receptor alpha 2 (IL-13Rα2), CD171, Human leukocyte antigen A1 (HLA-A1), Human leukocyte antigen A2 (HLA-A2), folate receptor-alpha, CD44v6, CD44v7/8, αvβ6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, dual antigen, a cancer-testes antigen, mesothelin (MSLN), murine cytomegalovirus (CMV), mucin 1 (MUC1), MUC16, prostate specific antigen, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), oncofetal antigen, Receptor Tyrosine Kinase Like Orphan Receptor 1 (ROR1), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the recombinant receptor specifically binds to a tag comprised by a therapeutic agent that specifically targets the disease or condition or cells of the disease or condition, said tag having been or is to be administered to the subject.

In some embodiments, the recombinant receptor is a T cell receptor or a functional non-T cell receptor. In some embodiments, the recombinant receptor is a chimeric antigen receptor (CAR). In some cases, the CAR contains an extracellular antigen-recognition domain that specifically binds to the antigen and an intracellular signaling domain containing an ITAM, wherein optionally, the intracellular signaling domain contains an intracellular domain of a CD3-zeta (CD3ξ) chain; and/or wherein the CAR further contains a costimulatory signaling region, which optionally contains a signaling domain of CD28 or 4-1BB.

In some of any such embodiments, the engineered cells include T cells, optionally CD4+ and/or CD8+ T cells. In some instances, the T cells are primary T cells obtained from a subject.

In some embodiments, the cell therapy includes the administration of from or from about $1 \times 10^5$ to $1 \times 10^8$ total recombinant receptor-expressing cells, total T cells, or total peripheral blood mononuclear cells (PBMCs), from or from about $5 \times 10^5$ to $1 \times 10^7$ total recombinant receptor-expressing cells, total T cells, or total peripheral blood mononuclear cells (PBMCs) or from or from about $1 \times 10^6$ to $1 \times 10^7$ total recombinant receptor-expressing cells, total T cells, or total peripheral blood mononuclear cells (PBMCs), each inclusive. In some embodiments, the cell therapy includes the administration of no more than $1 \times 10^8$ total recombinant receptor-expressing cells, total T cells, or total peripheral blood mononuclear cells (PBMCs), no more than $1 \times 10^7$ total recombinant receptor-expressing cells, total T cells, or total peripheral blood mononuclear cells (PBMCs), no more than $0.5 \times 10^7$ total recombinant receptor-expressing cells, total T cells, or total peripheral blood mononuclear cells (PBMCs), no more than $1 \times 10^6$ total recombinant receptor-expressing cells, total T cells, or total peripheral blood mononuclear cells (PBMCs), no more than $0.5 \times 10^6$ total recombinant receptor-expressing cells, total T cells, or total peripheral blood mononuclear cells (PBMCs).

In some of any such embodiments, the dose that is not associated with risk of developing toxicity or severe toxicity is or contains less than or less than about $5 \times 10^7$ total recombinant receptor-expressing cells, optionally CAR+ cells, total T cells, or total peripheral blood mononuclear cells (PBMCs), such as less than or less than about $2.5\times10^7$, less than or less than about $1.0\times10^7$, less than or less than about $5.0\times10^6$, less than or less than about $1.0\times10^6$, less than or less than about $5.0\times10^5$, or less than or less than about $1\times10^5$ total recombinant receptor-expressing cells, optionally CAR+ cells, total T cells, or total peripheral blood mononuclear cells (PBMCs). In some embodiments, the dose that is not associated with risk of developing toxicity or severe toxicity is or contains from or from about $1\times10^5$ to $5\times10^7$ total recombinant receptor-expressing cells, optionally CAR+ cells, total T cells, or total peripheral blood mononuclear cells (PBMCs), such as $1\times10^5$ to $2.5\times10^7$, $1\times10^5$ to $1.0\times10^7$, $1\times10^5$ to $5.0\times10^6$, $1\times10^5$ to $1.0\times10^6$, $1.0\times10^5$ to $5.0\times10^5$, $5.0\times10^5$ to $5\times10^7$, $5\times10^5$ to $2.5\times10^7$, $5\times10^5$ to $1.0\times10^7$, $5\times10^5$ to $5.0\times10^6$, $5\times10^5$ to $1.0\times10^6$, $1.0\times10^6$ to $5\times10^7$, $1\times10^6$ to $2.5\times10^7$, $1\times10^6$ to $1.0\times10^7$, $1\times10^6$ to $5.0\times10^6$, $5.0\times10^6$ to $5\times10^7$, $5\times10^6$ to $2.5\times10^7$, $5\times10^6$ to $1.0\times10^7$, $1.0\times10^7$ to $5\times10^7$, $1\times10^7$ to $2.5\times10^7$ or $2.5\times10^7$ to $5\times10^7$ total recombinant receptor-expressing cells, optionally CAR+ cells, total T cells, or total peripheral blood mononuclear cells (PBMCs).

In some of any such embodiments, the engineered cells are autologous to the subject. In some embodiments, the engineered cells are allogeneic to the subject. In some cases, the reagent is detectably labeled, optionally fluorescently labeled.

Provided herein are any of the provided articles of manufacture wherein the instructions specify carrying out any of the methods provided herein.

DETAILED DESCRIPTION

Figure 1B:
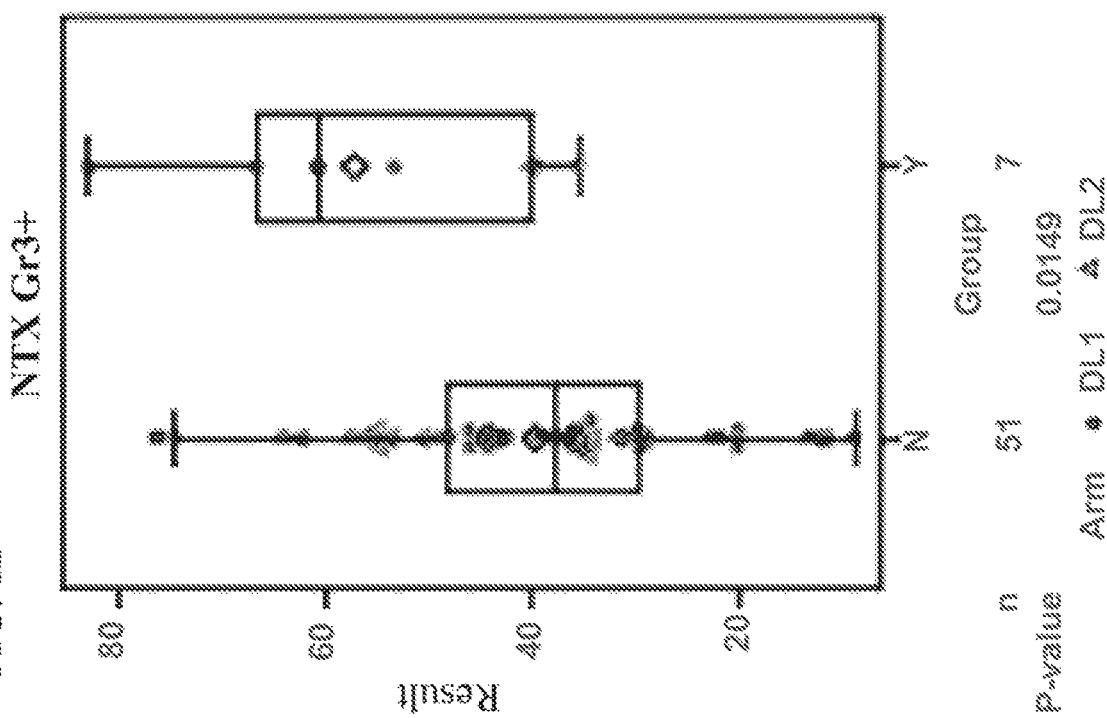
FIG. 1B shows a graph displaying the percentages of CD14+ monocytes in leukapheresis samples in subjects. Data is shown for subjects who did not develop neurotoxicity (left) versus subjects who developed Grade 3 or higher neurotoxicity (right).

Provided herein are articles of manufacture, kits and methods involving reagents that are capable of detecting or that are specific for a population of myeloid cells or a marker expressed on a population of myeloid cells for use in conjunction with a cell therapy (e.g. CAR+ T cells) and/or agents for treating a toxicity, including for use as a companion diagnostic and/or in prophylactic treatment methods in connection with adoptive cell therapy. In some embodiments, the provided articles of manufacture and methods are associated with reducing the risk of developing a toxicity, such as a severe toxicity, e.g. severe neurotoxicity, in subjects administered a cell therapy, such as a CAR+ T cell therapy.

In some embodiments, the cell therapy is or comprises a tumor infiltrating lymphocytic (TIL) therapy, a transgenic TCR therapy or a recombinant-receptor expressing cell therapy (optionally T cell therapy), which optionally is a chimeric antigen receptor (CAR)-expressing cell therapy. Thus, in some embodiments, the immunotherapy involves the administration of a composition containing a plurality of tumor-infiltrating lymphocytes (TILs), a plurality of cells, such as T cells, e.g., engineered T cells, expressing a recombinant receptor, such as a TCR or a chimeric antigen receptor In some embodiments, the recombinant receptor is a TCR. In some cases, the recombinant receptor is a chimeric antigen receptor (CAR).

Adoptive cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. In certain contexts, available approaches to adoptive cell therapy may not always be entirely satisfactory. In some contexts, optimal efficacy can depend on the ability of the administered cells to recognize and bind to a target, e.g., target antigen, to traffic, localize to and successfully enter appropriate sites within the subject, tumors, and environments thereof, to become activated, expand, to exert various effector functions, including cytotoxic killing and secretion of various factors such as cytokines, to persist, including long-term, to differentiate, transition or engage in reprogramming into certain phenotypic states (such as effector, long-lived memory, less-differentiated, and effector states), to provide effective and robust recall responses following clearance and re-exposure to target ligand or antigen, and avoid or reduce exhaustion, anergy, terminal differentiation, and/or differentiation into a suppressive state.

Certain available methods for treating or ameliorating toxicity may not always be entirely satisfactory. Many such approaches focus, for example, on targeting downstream effects of toxicity, such as by cytokine blockade, and/or delivering agents such as high-dose steroids which can also eliminate or impair the function of administered cells. Additionally, such approaches often involve administration of such interventions only upon detection of physical signs or symptoms of toxicity, which, in some cases, may develop upon development of severe toxicity in the subject. It may also not be possible to predict, before the cell therapy, whether a subject is at risk for toxicity. Many of these other approaches also do not prevent other forms of toxicity such as neurotoxicity, which can be associated with adoptive cell therapy. In some cases, such therapies are administered only after a subject presents with a physical sign or symptom of a toxicity. In some cases, this is at a time where such symptoms are severe, and that therefore may require even harsher or more extreme treatments (e.g. higher dosages or an increased frequency of administration) to ameliorate or treat the toxicity.

The use of certain alternative approaches does not provide satisfactory solutions to such issues. For example, an approach that included treatment of all or a large subset of subjects administered a treatment such as a cell therapy (e.g., larger than the subset of subjects that will ultimately develop toxicity or are at or above a certain level of risk therefor), regardless of risk or with a threshold of risk that is too low, may not be satisfactory. For example, a subject administered with a cell therapy with an agent or therapy for ameliorating or preventing a toxicity (e.g. steroid). For example, such approaches in which the treatment was administered concurrently with the administration of the cells, or within a window of time after administration of cells, but before the development of a physical sign or symptom or severe sign or symptom, at least without the appropriate level of risk assessment, may not be satisfactory. For example, not all subjects administered with a cell therapy will or do develop a toxic outcome, or develop such a toxic outcome that requires intervention. Thus, such alternatives in some contexts would involve needlessly treating certain subjects in which such treatment may be unwarranted. Further, in some cases, such agents and therapies (e.g. steroids) are themselves associated with toxic side effects. Such side effects may be even greater at the higher dose or frequency in which is it necessary to administer or treat with the agent or therapy in order to treat or ameliorate the severity of the toxicity that can result from cell therapy. In addition, in some cases, an agent or therapy for treating a toxicity may limit the efficacy of the cell therapy, such as the efficacy of the chimeric receptor (e.g. CAR) expressed on cells provided as part of the cell therapy (Sentman (2013) Immunotherapy, 5:10).

The provided articles of manufacture and methods offer advantages over available approaches and alternative solutions for addressing, predicting, and treating or preventing, the risk of toxic outcomes. The provided reagents can be used as companion diagnostics with a cell therapy, such as a therapeutic cell composition, comprising genetically engineered cells expressing a recombinant receptor for treating a disease or condition.

In some embodiments, the provided methods and articles of manufacture are based on observations that a percentage of cells expressing a myeloid cell marker (e.g. CD14) in a biological sample (e.g. apheresis or leukapheresis) in subjects that are subsequently administered a cell therapy, such as a cell therapy containing a dose or composition of genetically engineered cells expressing a recombinant receptor) correlate to a risk of developing a toxicity. The provided articles of manufacture and methods relate to a reagent capable of detecting or that is specific for a population of myeloid cells or a marker expressed on a population of myeloid cells. In some embodiments, instructions are provided for using the reagent to assay a biological sample from a subject that is a candidate for treatment, optionally with a cell therapy, said cell therapy optionally including a dose or composition of genetically engineered cells expressing a recombinant receptor.

In some embodiments, the method or articles of manufacture is used to assess markers (e.g. expressed on a population of myeloid cells) correlated with potential toxicities that may be associated with certain therapies when administered to a subject. In some embodiments, the methods and articles of manufacture are useful for determining the administration and dosage of a cell based therapy and/or agent that reduces or ameliorates toxicity. In some embodiments, the cell therapy is a tumor infiltrating lymphocytic (TIL) therapy, a transgenic TCR therapy or a recombinant-receptor expressing cell therapy (optionally T cell therapy), which optionally is a chimeric antigen receptor (CAR)-expressing cell therapy. In some embodiments, the recombinant receptor is a TCR. In some cases, the recombinant receptor is a chimeric antigen receptor (CAR). In some embodiments, the method further involves administering a lymphodepleting therapy.

In particular, the provided articles of manufacture or methods in some embodiments are associated with generally identifying only those subjects predicted to be at risk or above a particular threshold risk level for developing toxicity, such as one related to a cell therapy. Thus, the provided methods in some embodiments permit intervention of a risk of developing toxic outcomes in only a subset of subjects that are more likely to develop toxicity. In many cases, this avoids treating the toxicity in all subjects being administered the cell therapy, which as described above may be unwarranted if many of the subjects would never have developed the toxicity and/or can result in significant side effects itself.

Further, the provided methods in some embodiments also provide advantages associated with the feature that the risk of developing toxicity, such as neurotoxicity (e.g. severe neurotoxicity), can be predicted by detecting a marker in a blood sample from the subject, before administration a treatment such as a cell therapy. Thus, in some cases, those subjects that are predicted to be at risk of and/or are more likely to be at risk for developing toxicity (e.g. CRS or neurotoxicity, such as severe CRS or severe neurotoxicity) can receive an intervention early or can receive a prophylactic treatment. In some cases, the methods or articles of manufacture allow a subject to receive agents or treatments for treating, preventing, delaying, or attenuating the development of a toxicity generally before a physical sign or symptom of the toxicity, e.g. severe toxicity, has developed that would otherwise lead to an intervening treatment. In some cases, the ability to intervene early in the treatment of a toxic outcome or the potential of a toxic outcome can mean that a reduced dosage of an agent for treating or ameliorating the toxicity can be given and/or a decreased frequency of administration of such agent or therapy can be given.

In some embodiments, the presence of a percentage of cells positive for marker expressed on a population of myeloid cells (e.g. CD14) above a threshold level indicates the subject may be in need of a prophylactic treatment for ameliorating toxicity and/or should be dosed or administered the recombinant receptor-expressing cells in a manner to minimize or reduce the risk of the toxicity. Thus, such markers as described herein can be used in predictive methods to identify subjects that are likely or more likely to develop a toxicity to the cell therapy in order to be able to intervene earlier in the treatment of the subject to reduce later severe toxicity. Such methods can inform rational strategies for intervening and thereby facilitate the safe and effective clinical application of adoptive cell therapy, such as CAR-T cell therapy.

In some embodiments, the article of manufacture or methods include a reagent capable of detecting or that is specific for a population of myeloid cells or a marker expressed on a population of myeloid cells (e.g. CD14). In some embodiments, instructions are provided for using the reagent to assay a biological sample from a subject that is a candidate for treatment, optionally with a cell therapy, said cell therapy optionally including a dose or composition of genetically engineered cells expressing a recombinant receptor. The article may alternatively or further include, in some embodiments, one or more agents or treatments for treating, preventing, delaying, reducing or attenuating the development or a risk of development of a toxicity and/or instructions for the administration of one or more agents or treatments for treating, preventing, delaying, reducing or attenuating the development or risk of development of a toxicity in the subject.

In some embodiments, the article of manufacture contains the reagent capable of detecting or that is specific for a population of myeloid cells or a marker (e.g. CD14) expressed on a population of myeloid cells and provides instructions to assay a biological sample from a subject that is a candidate for treatment, optionally with a cell therapy.

Also provided is an article of manufacture containing a cell therapy containing a dose or composition of genetically engineered cells expressing a recombinant receptor, and instructions for administering the cell therapy following or based on the results of an assessment, in a biological sample (e.g. apheresis or leukapheresis sample) of the presence or percentage or number of cells of a myeloid cell population or of a level of expression of a marker (e.g. CD14) expressed by cells of said population or of a myeloid marker. In some embodiments, the biological sample obtained from the subject prior to administering the cell therapy and/or said biological sample not comprising the recombinant receptor and/or said engineered cells.

Also provided is an article of manufacture containing an agent capable of treating, preventing, delaying, reducing or attenuating the development or risk of development of a toxicity, and instructions for administering the agent following or based on the results of an assessment in a biological sample of the presence or percentage or number of cells of a myeloid cell population or of a level of expression of a marker expressed by cells of said population or of a myeloid marker.

In some embodiments, the assessment includes detection which optionally includes contacting a reagent capable of directly or indirectly detecting myeloid cells or a marker expressed on a population of myeloid cells with the biological sample and determining the percentage or number of cells positive for, optionally surface positive for, the myeloid marker and/or level in the biological sample. In some cases, the population of cells is or contains monocytes.

In some embodiments of the article of manufacture, instructions are also provided. The instructions specify, for example, that if the percentage or number of cells in the sample positive for the marker, and/or percentage or number of cells of the population in the sample, is at or above a threshold level, an agent or other treatment capable of treating, preventing, delaying, reducing or attenuating the development or risk of development of a toxicity is administered to the subject (i) prior to, (ii) within one, two, or three days of, (iii) concurrently with and/or (iv) at first fever following, the initiation of administration of the cell therapy to the subject.

In some cases, the instructions specify administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy if the percentage or number of cells in the sample positive for the marker, and/or percentage or number of cells of the population in the sample, is at or above a threshold level. Further, in some embodiments, the instructions specify administering to the subject the cell therapy in an in-patient setting and/or with admission to the hospital for one or more days, optionally wherein the cell therapy is otherwise to be administered to subjects on an outpatient basis or without admission to the hospital for one or more days if the percentage or number of cells in the sample positive for the marker, and/or percentage or number of cells of the population in the sample, is at or above a threshold level.

In some embodiments, the instructions further specify that if the number or percentage of cells in the sample positive for the marker, and/or percentage or number of cells of the population in the sample, is below a threshold level, a cell therapy, optionally at a non-reduced dose, optionally on an outpatient basis or without admission to the hospital for one or more days is administered to the subject.

Also provided are methods for selecting a subject for treatment including contacting a biological sample (e.g. apheresis or leukapheresis sample) with a reagent capable of detecting or that is specific for a population of myeloid cells or a marker expressed on a population of myeloid cells (e.g. CD14). In some embodiments of the method, the biological sample is from a subject that is a candidate for treatment with a cell therapy containing a dose or composition of genetically engineered cells expressing a recombinant receptor and the biological sample is obtained from the subject prior to administering the cell therapy and/or said biological sample does not comprise the recombinant receptor and/or said engineered cells. In some embodiments, the method also includes selecting a subject in which either the percentage or number of cells in the sample positive for the marker, and/or percentage or number of cells of the population in the sample, is at or above a threshold level, thereby identifying a subject that is at risk for developing a toxicity to the cell therapy or the percentage or number of cells in the sample positive for the marker, and/or percentage or number of cells of the population in the sample, is below a threshold level. The method further includes selecting a subject in which either the percentage or number of cells in the sample positive for the marker, and/or percentage or number of cells of the population in the sample, is at or above a threshold level, thereby identifying a subject that is at risk for developing a toxicity to the cell therapy; or the percentage or number of cells in the sample positive for the marker, and/or percentage or number of cells of the population in the sample, is below a threshold level.

In some embodiments, if the percentage or number of cells positive for the myeloid marker is at or above a threshold level, the agent or other treatment capable of treating, preventing, delaying, or attenuating the development of a toxicity is administered prior to and/or concurrently with administration of the therapeutic cell composition comprising the genetically engineered cells; and/or a dose of genetically engineered cells of the therapeutic cell composition that is not associated with risk of developing toxicity, or is not associated with a risk of developing a toxicity in a majority of subjects administered a therapeutic cell composition comprising the genetically engineered cells is administered to the subject; and/or the therapeutic cell composition comprising genetically engineered cells is administered to the subject in an in-patient setting and/or with admission to the hospital for one or more days, optionally wherein the cell therapy is otherwise to be administered to subjects on an outpatient basis.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. REAGENTS FOR DETECTING MYELOID CELLS OR A MARKER EXPRESSED ON MYELOID CELLS

Provided herein are articles of manufacture containing a reagent a reagent capable of detecting or that is specific for a population of myeloid cells or a marker expressed on a population of myeloid cells, such as on a population of monocytes, (e.g. CD14). In some embodiments, instructions are provided for using the reagent to assay a biological sample from a subject that is a candidate for treatment, optionally with a cell therapy, said cell therapy optionally including a dose or composition of genetically engineered cells expressing a recombinant receptor. In some embodiments, the biological sample is an apheresis sample. Also provided is an article of manufacture containing a cell therapy containing a dose or composition of genetically engineered cells expressing a recombinant receptor, and instructions for administering the cell therapy following or based on the results of an assessment, in a biological sample (e.g. apheresis or leukapheresis sample) of the presence or percentage or number of cells of a myeloid cell population or of a level of expression of a marker (e.g. CD14) expressed by cells of said population or of a myeloid marker. In some embodiments, the percentage is a percentage of the myeloid cell population or of cells positive for the myeloid marker among total leukocytes or total CD45+ cells, or viable cells thereof, in the sample. In some cases, the percentage is a percentage of the myeloid cell population or cells positive for the myeloid marker among total leukocytes or CD45+ cells, or viable cells thereof, in the sample. In some examples, the percentage is a percentage of CD14+ cells among total leukocytes or CD45+ cells. In some embodiments, the cells are surface positive for CD14.

In some aspects, the population of cells is or contains monocytes. In some embodiments, the biological sample obtained from the subject prior to administering the cell therapy and/or said biological sample not comprising the recombinant receptor and/or said engineered cells. In some embodiments, the marker is a myeloid cell marker and/or wherein the marker is CD14 and/or wherein the population of cells is or comprises CD14+ myeloid cells. In some cases, the marker is human, optionally human CD14. Also provided are methods for selecting a subject for treatment including contacting a biological sample (e.g. apheresis or leukapheresis sample) with the reagent capable of detecting or that is specific for a population of myeloid cells or a marker expressed on a population of myeloid cells (e.g. CD14).

A. Sample

In some embodiments, the biological sample is obtained from a subject or a group of subjects prior to receiving a cell therapy optionally including a dose or composition of genetically engineered cells expressing a recombinant receptor. For example, the biological sample is from a subject that is a candidate for treatment with a cell therapy containing a dose or composition of genetically engineered cells expressing a recombinant receptor and the biological sample is obtained from the subject prior to administering the cell therapy and/or said biological sample does not comprise the recombinant receptor and/or said engineered cells. In some cases, the biological sample is or is obtained from a blood, plasma or serum sample. For example, the biological sample is or is obtained from an apheresis or leukapheresis sample. In some embodiments, the sample is enriched for monocytes. In some cases, the sample is obtained from leukapheresis collection system. In some embodiments, the apheresis or leukapheresis sample is from the same sample from which the cell therapy is engineered.

In some embodiments, the sample is from a subject that has a disease or a condition. For example, the disease or condition is a cancer. In some cases, the subject is a candidate for treatment with a cell therapy containing a dose or composition of genetically engineered cells expressing a recombinant receptor. In some embodiments, the disease or condition is a tumor, such as a solid tumor, lymphoma, leukemia, blood tumor, metastatic tumor, or other cancer or tumor type. In some specific examples, the disease or condition is a myeloma, leukemia or lymphoma.

In some embodiments, the cancer or proliferative disease is a B cell malignancy or hematological malignancy. In some embodiments the cancer or proliferative disease is lymphoblastic leukemia (ALL), non-Hodgkin's lymphoma (NHL), or chronic lymphocytic leukemia (CLL). In some embodiments, the cancer is CLL. In some embodiments, the methods can be used to treat a myeloma, a lymphoma or a leukemia. In some embodiments, the methods can be used to treat a non-Hodgkin lymphoma (NHL), an acute lymphoblastic leukemia (ALL), a chronic lymphocytic leukemia (CLL), a diffuse large B-cell lymphoma (DLBCL), acute myeloid leukemia (AML), or a myeloma, e.g., a multiple myeloma (MM). In some embodiments, the methods can be used to treat a NHL or a DBCBL.

B. Method for Detecting

Provided herein are articles of manufacture and containing a reagent a reagent capable of detecting or that is specific for a population of myeloid cells or a marker expressed on a population of myeloid cells (e.g. CD14) and uses of the articles of manufacture. In some embodiments, instructions are also provided for using the reagent to assay a biological sample from a subject that is a candidate for treatment, optionally with a cell therapy, said cell therapy optionally including a dose or composition of genetically engineered cells expressing a recombinant receptor. In some embodiments of using the articles of manufacture, the detecting for a marker that is specific for a population of myeloid cells or a marker expressed on or by a population of myeloid cells is performed up to 2 days, up to 7 days, up to 14 days, up to 21 days, up to 28 days, up to 35 days or up to 40 days prior to initiation of the administration of the engineered cells.

In some embodiments, using the articles of manufacture includes detecting a marker expressed on a population of myeloid cells (e.g. CD14) or a portion thereof. The marker detected can be expressed on the surface of myeloid cells or in a population of myeloid cells. In some examples, it is expressed on monocytes. In some embodiments, the marker is a myeloid cell marker, such as a human myeloid cell marker, such as a monocyte marker, e.g., a human monocyte marker. In some aspects, the monocyte marker is a marker present on, e.g., on the surface of, all or most monocytes or most monocyte populations, optionally in a human or in a healthy individual. In some aspects, the monocyte marker is not present on or is not ordinarily expressed on populations of cells other than myeloid cells or other than monocytes, such as is not present on lymphocytes and/or is not expressed on neutrophils. In some aspects, the monocyte marker is a marker that is co-expressed or substantially co-expressed with, or that has a coextensive or essentially coextensive expression pattern, CD14 in human cells and/or has a similar or essentially the same expression pattern as CD14 in humans. In some embodiments, the marker is a myeloid cell marker and/or the marker is CD14 and/or wherein the population of cells is or comprises CD14+ myeloid cells. In some cases, the CD14 is membrane bound or expressed on the surface of a cell. In some embodiments, the CD14 is a human CD14. In some embodiments, the CD14 comprises the sequence of amino acids set forth in SEQ ID NOS: 27-28 or a sequence of amino acids having at least at or about 85%, 86%, 87%, 88%, 89%, 90%, 91%, 92%, 93%, 94%, 95%, 96%, 97%, 98%, 99% or more sequence identity to SEQ ID NOS: 27-28.

In some embodiments, the reagent capable of detecting or that is specific for a population of myeloid cells or a marker expressed on a population of myeloid cells binds the marker (e.g. CD14). In some cases, the assaying or assessing cells myeloid cells or a marker expressed on a population of myeloid cells is using flow cytometry. In some cases, the reagent is a soluble protein that binds CD14. For example, in some embodiments, bacterial lipopolysaccharide (LPS) can be used to bind and detect CD14. In some embodiments, the CD14 detecting antibody is selected from the group consisting of ab45870 (Abcam), HCD14 (Biolegend), M5E2 (Biolegend), TUK4 (Bio-Rad), and MAB3832 (R&D Systems).

The term "antibody" herein is used in the broadest sense and includes polyclonal and monoclonal antibodies, including intact antibodies and functional (antigen-binding) antibody fragments, including fragment antigen binding (Fab) fragments, F(ab)$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

Also provided are antibody immunoconjugates comprising an antibody against the marker expressed on a population of myeloid cells attached to a label, which can generate a detectable signal, indirectly or directly. These antibody immunoconjugates can be used for research or diagnostic applications. The label is preferably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I, $^{131}$I, a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example $^{99}$Tc or $^{123}$I, or a spin label for nuclear magnetic resonance (NMR) imaging (also known as magnetic resonance imaging, MM), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

In some embodiments, the antibody immunoconjugate is detectable indirectly. For example, a secondary antibody that is specific for the antibody against the marker expressed on a population of myeloid cells immunoconjugate and contains a detectable label can be used to detect the antibody immunoconjugate.

In some embodiments, antibodies capable of detecting or that is specific for a population of myeloid cells or a marker expressed on a population of myeloid cells (e.g. CD14) provided herein may be identified, screened for, or characterized for their physical/chemical properties and/or biological activities by various known assays. In one aspect, the antibody is tested for its antigen binding activity, e.g., by known methods such as an immunoassay, ELISA, Western blotting, and/or flow cytometric assays, including cell-based binding assays.

II. INTERVENTIONS OR AGENTS THAT TREAT OR AMELIORATE SYMPTOMS OF TOXICITY

The provided articles of manufacture or methods are for use in connection with, or involve or include, one or more agents or other treatments capable of treating, preventing, delaying, reducing or attenuating the development or risk of development of a toxicity. In some cases, the toxicity includes neurotoxicity or cytokine release syndrome (CRS), optionally grade 1 or higher neurotoxicity or CRS. In some embodiments, the toxicity includes severe neurotoxicity and/or comprises a grade 2 or higher neurotoxicity, a grade 3 or higher neurotoxicity, at least prolonged grade 3 neurotoxicity or is at or above grade 4 or grade 5 neurotoxicity; and/or the toxicity comprises severe CRS and/or comprises grade 2 or higher or grade 3 or higher CRS. In some embodiments, the toxicity is severe neurotoxicity (e.g. grade 3 or higher neurotoxicity). In some specific examples, the toxicity is associated with cerebral edema.

A. Toxicity

1. Neurotoxicity

In some embodiments, the therapy-induced toxic outcome or symptom is associated with neurotoxicity. In some embodiments, the therapy-induced toxic outcome or symptom is associated with severe neurotoxicity (e.g. grade 3 or higher neurotoxicity). In some embodiments, symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute—Common Toxicity Criteria version 4.03 (NCI-CTCAE v4.03). In some cases, the neurotoxicity is severe neurotoxicity and/or the neurotoxicity is a grade 3 or higher neurotoxicity. In some embodiments, the toxic outcome or symptom is associated with grade 3, grade 4 or grade 5 neurotoxicity.

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

As used herein, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 1.

TABLE 1

Exemplary Grading Criteria for neurotoxicity

| Grade | Description of Symptoms |
| --- | --- |
| 1 Asymptomatic or Mild | Mild or asymptomatic symptoms |
| 2 Moderate | Presence of symptoms that limit instrumental activities of daily living (ADL), such as preparing meals, shopping for groceries or clothes, using the telephone, managing money |
| 3 Severe | Presence of symptoms that limit self-care ADL, such as bathing, dressing and undressing, feeding self, using the toilet, taking medications |
| 4 Life-threatening | Symptoms that are life-threatening, requiring urgent intervention |
| 5 Fatal | Death |

In some embodiments, the methods reduce symptoms associated with CNS-outcomes or neurotoxicity compared to other methods. For example, subjects treated according to the present methods may lack detectable and/or have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods in which the inhibitor is not administered. In some embodiments, subjects treated according to the present methods may have reduced symptoms associated with peripheral motor neuropathy, peripheral sensory neuropathy, dysesthesia, neuralgia or paresthesia.

In some embodiments, the methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals. In some embodiments, the symptom or outcome is cerebral edema which co-presents with neurotoxicity. In some cases, the cerebral edema involves alterations in blood brain barrier function and or tight junction integrity.

In some embodiments, administration of the agent reduces symptoms associated with neurotoxicity compared to other methods. For example, subjects treated with the inhibitor may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects who do not receive the agent, or receive the agent at a time when physical symptoms of neurotoxicity have manifested in the subject. In some embodiments, subjects treated with the agent according to the present methods may have reduced symptoms associated with peripheral motor neuropathy, peripheral sensory neuropathy, dysesthesia, neuralgia or paresthesia.

The toxic outcome or symptoms is one or more of confusion, delirium, expressive aphasia, obtundation, myoclonus, lethargy, altered mental status, convulsions, seizure-like activity, seizures (optionally as confirmed by electroencephalogram [EEG]), cerebral edema, elevated levels of beta amyloid (Aβ), elevated levels of glutamate, and elevated levels of oxygen radicals, encephalopathy, dysphasia, tremor, choreoathetosis, symptoms that limit self-care, symptoms of peripheral motor neuropathy, symptoms of peripheral sensory neuropathy and combinations thereof.

In some embodiments, a toxic outcome or symptom of neurotoxicity in the subject at day up to or up to about day 7, 8, 9, 10, 11, 12, 13, 14, 15, 16, 17, 18, 19, 20, 21, 22, 23, 24, 25, 26, 27, 28, 29 or 30 following initiation of administration of the therapeutic agent, e.g. cell therapy, is not detectable or is reduced as compared to a method in which the cell therapy is administered to the subject in the absence of the agent. In some aspects, the toxic outcome or symptom of neurotoxicity is reduced by greater than 50%, 60%, 70%, 80%, 90% or more.

In some aspects, the physical signs or symptoms associated with toxicity include e.g., severe neurotoxicity, include confusion, delirium, expressive aphasia, obtundation, myoclonus, lethargy, altered mental status, convulsions, seizure-like activity, seizures (such as confirmed by electroencephalogram [EEG]), encephalopathy, dysphasia, tremor, choreoathetosis, symptoms that limit self-care, symptoms of peripheral motor neuropathy, symptoms of peripheral sensory neuropathy or combinations thereof. In some cases, the physical signs or symptoms associated with toxicity, e.g., severe neurotoxicity, are associated with grade 3, grade 4 or grade 5 neurotoxicity. In some embodiments, the physical signs or symptoms associated with toxicity, e.g., severe neurotoxicity, manifest greater than or greater than about or about 5 days after cell therapy, 6 days after cell therapy or 7 days after cell therapy.

In some embodiments, the method ameliorates neurotoxicity, e.g., severe neurotoxicity and/or reduces the physical signs or symptoms of severe neurotoxicity compared to a subject in which severe neurotoxicity is treated after the subject exhibits a physical sign or symptom of neurotoxicity and/or compared to a subject in which severe neurotoxicity is treated greater than 5 days, greater than 6 days or greater than 7 days after administration of the cell therapy. In some cases, the treated subject does not exhibit grade 3 or higher neurotoxicity or a majority of treated subjects do not exhibit grade 3 or higher neurotoxicity.

2. Cytokine Release Syndrome

In some embodiments, the toxic outcome or symptom is associated with cytokine-release syndrome (CRS). In some embodiments, the CRS is severe CRS and/or the CRS is grade 3 or higher CRS. In some cases, the toxic outcome or symptom is one or more of fever, hypotension, hypoxia, neurologic disturbances, or elevated serum level of an inflammatory cytokine or C reactive protein (CRP). In some embodiments, the toxic outcome or symptom of CRS in the subject at day up to or up to about day 7, 8, 9, 10, 11, 12, 13, 14, 15, 16, 17, 18, 19, 20, 21, 22, 23, 24, 25, 26, 27, 28, 29 or 30 following initiation of administration of the cell therapy is not detectable or is reduced as compared to a method in which the cell therapy is administered to the subject in the absence of the agent. In some embodiments, CRS is reduced by greater than 50%, 60%, 70%, 80%, 90% or more.

In some aspects, the toxic outcome of a therapy, such as a cell therapy, is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure.

Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS, such as severe CRS, typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1β, IL-6, IL-8, and IL-10.

CRS criteria that appear to correlate with the onset of CRS to predict which patients are more likely to be at risk for developing sCRS have been developed (see Davilla et al. Science translational medicine. 2014; 6(224):224ra25). Factors include fevers, hypoxia, hypotension, neurologic changes, elevated serum levels of inflammatory cytokines, such as a set of seven cytokines (IFNγ, IL-5, IL-6, IL-10, Flt-3L, fractalkine, and GM-CSF) whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 2 below.

TABLE 2

Exemplary Grading Criteria for CRS

| Grade | Description of Symptoms |
|---|---|
| 1<br>Mild | Not life-threatening, require only symptomatic treatment such as antipyretics and anti-emetics (e.g., fever, nausea, fatigue, headache, myalgias, malaise) |
| 2<br>Moderate | Require and respond to moderate intervention:<br>Oxygen requirement <40%, or<br>Hypotension responsive to fluids or low dose of a single vasopressor, or<br>Grade 2 organ toxicity (by CTCAE v4.0) |
| 3<br>Severe | Require and respond to aggressive intervention:<br>Oxygen requirement ≥40%, or<br>Hypotension requiring high dose of a single vasopressor (e.g., norepinephrine ≥20 µg/kg/min, dopamine ≥10 µg/kg/min, phenylephrine ≥200 µg/kg/min, or epinephrine ≥10 µg/kg/min), or<br>Hypotension requiring multiple vasopressors (e.g., vasopressin + one of the above agents, or combination vasopressors equivalent to ≥20 µg/kg/min norepinephrine), or<br>Grade 3 organ toxicity or Grade 4 transaminitis (by CTCAE v4.0) |
| 4<br>Life-threatening | Life-threatening:<br>Requirement for ventilator support, or<br>Grade 4 organ toxicity (excluding transaminitis) |
| 5<br>Fatal | Death |

As used herein, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia ($PO_2$<90%) or one or more neurologic disorder(s) (including mental status changes, obtundation, and/or seizures). In some embodiments, severe CRS includes CRS with a grade of 3 or greater.

In some embodiments, outcomes associated with severe CRS or grade 3 CRS include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures).

In some embodiments, severe CRS encompasses a combination of (1) persistent fever (fever of at least 38 degrees Celsius for at least three days) and (2) a serum level of CRP of at least at or about 20 mg/dL. In some embodiments, severe CRS encompasses hypotension requiring the use of two or more vasopressors or respiratory failure requiring mechanical ventilation.

In some embodiments, the subject exhibits a fever, and in some aspects is treated at a time at which the subject exhibits such fever and/or exhibits or has exhibited the fever for a particular period of time.

In some embodiments, the fever in the subject is characterized as a body temperature of the subject that is (or is measured at) at or above a certain threshold temperature or level. In some aspects, the threshold temperature is that associated with at least a low-grade fever, with at least a moderate fever, and/or with at least a high-grade fever. In some embodiments, the threshold temperature is a particular temperature or range. For example, the threshold temperature may be at or about 38, 39, 40, 41, or 42 degrees Celsius, and/or may be a range of at or about 38 degrees Celsius to at or about 39 degrees Celsius, a range of at or about 39 degrees Celsius to at or about 40 degrees Celsius, a range of at or about 40 degrees Celsius to at or about 41 degrees, or a range of at or about 41 degrees Celsius to at or about 42 degrees Celsius.

In some embodiments, the fever is a sustained fever; in some aspects, the subject is treated at a time at which a subject has been determined to have a sustained fever, such as within one, two, three, four, five six, or fewer hours of such determination or of the first such determination following the initial therapy having the potential to induce the toxicity, such as the disease-targeted therapy.

In some embodiments, the subject has, and/or is determined to or considered to have, a sustained fever if he or she exhibits a fever at or above the relevant threshold temperature, and where the fever or body temperature of the subject does not fluctuate by about, or by more than about, 1° C., and generally does not fluctuate by about, or by more than about, 0.5° C., 0.4° C., 0.3° C., or 0.2° C. Such absence of fluctuation above or at a certain amount generally is measured over a given period of time (such as over a 24-hour, 12-hour, 8-hour, 6-hour, 3-hour, or 1-hour period of time, which may be measured from the first sign of fever or the first temperature above the indicated threshold). For example, in some embodiments, a subject is considered to or is determined to exhibit sustained fever if he or she exhibits a fever of at least at or about 38 or 39 degrees Celsius, which does not fluctuate in temperature by more than at or about 0.5° C., 0.4° C., 0.3° C., or 0.2° C., over a period of 6 hours, over a period of 8 hours, or over a period of 12 hours, or over a period of 24 hours.

In some embodiments, the subject has, and/or is determined to or considered to have, a sustained fever if he or she exhibits a fever at or above the relevant threshold temperature, and where the fever or body temperature of the subject is not reduced, or is not reduced by or by more than a specified amount (e.g., by more than 1° C., and generally does not fluctuate by about, or by more than about, 0.5° C., 0.4° C., 0.3° C., or 0.2° C.), following a specified treatment, such as a treatment designed to reduce fever such as an antipyretic. An antipyretic may include any agent, e.g., compound, composition, or ingredient, that reduces fever, such as one of any number of agents known to have antipyretic effects, such as NSAIDs (such as ibuprofen, naproxen, ketoprofen, and nimesulide), salicylates, such as aspirin, choline salicylate, magnesium salicylate, and sodium salicylate, paracetamol, acetaminophen, Metamizole, Nabumetone, Phenaxone, antipyrine, febrifuges. In some embodiments, the antipyretic is acetaminophen. In some embodiments, it is or comprises ibuprophen or aspirin. For example, a subject is considered to have a sustained fever if he or she exhibits or is determined to exhibit a fever of at least at or about 38 or 39 degrees Celsius, which is not reduced by or is not reduced by more than at or about 0.5° C., 0.4° C., 0.3° C., or 0.2° C., or by at or about 1%, 2%, 3%, 4%, or 5%, over a period of 6 hours, over a period of 8 hours, or over a period of 12 hours, or over a period of 24 hours, even following treatment with the antipyretic such as tylenol. In some embodiments, the dosage of the antipyretic is a dosage ordinarily effective in such as subject to reduce fever or fever of a particular type such as fever associated with a bacterial or viral infection, e.g., a localized or systemic infection.

In some embodiments, the amelioration of CRS is determined by assessing biomarkers indicative of CRS including serum factors and inflammatory cytokines such as IFNγ, GM-CSF, TNFα, IL-6, IL-10, IL-1β, IL-8, IL-2, MIP-1, Flt-3L, fracktalkine, and IL-5. In some embodiments, assessment or monitoring of CRS biomarkers is performed at the time of the administration of the cell therapy and/or after the administration of the cell therapy.

In some aspects, detecting the biomarker includes performing an in vitro assay. In some embodiments, the in vitro assay is an immunoassay, an aptamer-based assay, a histological or cytological assay, or an mRNA expression level assay. In some embodiments, the parameter or parameters for one or more of each of the one or more biomarkers are detected by an enzyme linked immunosorbent assay (ELISA), immunoblotting, immunoprecipitation, radioimmunoassay (MA), immunostaining, flow cytometry assay, surface plasmon resonance (SPR), chemiluminescence assay, lateral flow immunoassay, inhibition assay or avidity assay.

In some embodiments, the parameter for at least one of the one or more biomarkers is determined using a binding reagent that specifically binds to at least one biomarker. In some cases, the binding reagent is an antibody or antigen-binding fragment thereof, an aptamer or a nucleic acid probe.

B. Interventions

In some examples, the agent or other treatment capable of treating, preventing, delaying, or attenuating the development of a toxicity is administered prior to and/or concurrently with administration of a therapeutic cell composition comprising the genetically engineered cells. In some examples, the agent or other treatment capable of treating, preventing, delaying, or attenuating the development of a toxicity is administered (i) prior to, (ii) within one, two, or three days of, (iii) concurrently with and/or (iv) at first fever following, the initiation of administration of the cell therapy to the subject.

The agent or treatments are administered following or based on the results of an assessment, in a biological sample (e.g. apheresis or leukapheresis sample) of the presence or percentage or number of cells of a myeloid cell population or of a level of expression of a marker (e.g. CD14) expressed by cells of said population or of a myeloid marker. For example, the assessment includes detection such as by contacting a reagent capable of directly or indirectly detecting myeloid cells or a marker expressed on a population of myeloid cells with the biological sample and determining the percentage or number of cells positive for, optionally surface positive for, the marker and/or level in the biological sample. In some embodiments, a threshold level is determined based on the percentage or number of cells in the sample positive for the marker, and/or percentage or number of cells of the population in the sample, positive for the marker. In some aspects, the threshold level is a percent of cells surface positive for the marker in the biological sample or blood or apheresis sample that is or is about 20%, 25%, 30%, 35%, 40%, 45%, 50%, 55% or 60%. In some cases, the threshold level is a percent of cells surface positive for the myeloid marker in the biological sample that is or is about 45%, 46%, 47%, 48%, 49%, 50%, 51%, 52%, 53%, 54%, 55%, 56%, 57%, 58%, 59% or 60%. In some embodiments, the percentage is a percentage of the myeloid cell population or of cells positive for the myeloid marker among total leukocytes or total CD45+ cells, or viable cells thereof, in the sample. In some cases, the percentage is a percentage of the myeloid cell population or cells positive for the myeloid marker among total leukocytes or CD45+ cells, or viable cells thereof, in the sample. In some examples, the percentage is a percentage of CD14+ cells among total leukocytes or CD45+ cells.

In some cases, the threshold level is the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

In some embodiments, provided are methods for selecting a subject for treatment including contacting a biological sample (e.g. apheresis or leukapheresis sample) with a reagent capable of detecting or that is specific for a population of myeloid cells or a marker expressed on a population of myeloid cells (e.g. CD14). In some embodiments of the method, the biological sample is from a subject that is a candidate for treatment with a cell therapy containing a dose or composition of genetically engineered cells expressing a recombinant receptor and the biological sample is obtained from the subject prior to administering the cell therapy and/or said biological sample does not comprise the recombinant receptor and/or said engineered cells. In some embodiments, the method also includes selecting a subject in which either the percentage or number of cells in the sample positive for the marker, and/or percentage or number of cells of the population in the sample, is at or above a threshold level as described, thereby identifying a subject that is at risk for developing a toxicity to the cell therapy or the percentage or number of cells in the sample positive for the marker, and/or percentage or number of cells of the population in the sample, is below a threshold level.

In some embodiments, the method allows for selection of a subject for administration of an agent or other treatment capable of treating, preventing, delaying, reducing or attenuating the development or risk of development of a toxicity and (2) the cell therapy, wherein administration of the agent is to be administered (i) prior to, (ii) within one, two, or three days of, (iii) concurrently with and/or (iv) at first fever following, the initiation of administration of the cell therapy to the subject.

In some embodiments, the agent, e.g., a toxicity-targeting agent, or treatment capable of treating, preventing, delaying, or attenuating the development of a toxicity is a steroid, is an antagonist or inhibitor of a cytokine receptor, such as IL-6 receptor, CD122 receptor (IL-2Rbeta receptor), or CCR2, or is an inhibitor of a cytokine, such as IL-6, MCP-1, IL-10, IFN-γ, IL-8, or IL-18. In some embodiments, the agent is an agonist of a cytokine receptor and/or cytokine, such as TGF-β. In some embodiments, the agent, e.g., agonist, antagonist or inhibitor, is an antibody or antigen-binding fragment, a small molecule, a protein or peptide, or a nucleic acid.

In some embodiments, a fluid bolus can be employed as an intervention, such as to treat hypotension associated with CRS. In some embodiments, the target hematocrit levels are >24%. In some embodiments, the intervention includes the use of absorbent resin technology with blood or plasma filtration. In some cases, the intervention includes dialysis, plasmapheresis, or similar technologies. In some embodiments, vassopressors or acetaminophen can be employed.

In some embodiments, the agent can be administered sequentially, intermittently, or at the same time as or in the same composition as the therapy, such as cells for adoptive cell therapy. For example, the agent can be administered before, during, simultaneously with, or after administration of the immunotherapy and/or cell therapy.

In some embodiments, the agent is administered at a time as described herein and in accord with the provided methods. In some embodiments, the toxicity-targeting agent is administered at a time that is within, such as less than or no more than, 3, 4, 5, 6, 7, 8, 9 or 10 days after initiation of the immunotherapy and/or cell therapy. In some embodiments, the toxicity-targeting agent is administered within or within about 1 day, 2 days or 3 days after initiation of administration of the immunotherapy and/or cell therapy.

In some embodiments, the agent, e.g., toxicity-targeting agent, is administered to a subject after initiation of administration of the immunotherapy and/or cell therapy at a time at which the subject does not exhibit grade 2 or higher CRS or grade 2 or higher neurotoxicity. In some aspects, the toxicity-targeting agent is administered after initiation of administration of the immunotherapy and/or cell therapy at a time at which the subject does not exhibit severe CRS or severe neurotoxicity. Thus, between initiation of administration of the immunotherapy and/or cell therapy and the toxicity-targeting agent, the subject is one that does not exhibit grade 2 or higher CRS, such as severe CRS, and/or does not exhibit grade 2 or higher neurotoxicity, such as severe neurotoxicity.

Non-limiting examples of interventions for treating or ameliorating a toxicity, such as severe CRS (sCRS), are described in Table 3. In some embodiments, the intervention includes tocilizumab or other toxicity-targeting agent as described, which can be at a time in which there is a sustained or persistent fever of greater than or about 38° C. or greater than or greater than about 39° C. in the subject. In some embodiments, the fever is sustained in the subject for more than 10 hours, more than 12 hours, more than 16 hours, or more than 24 hours before intervention.

TABLE 3

Examples of interventions for treating or ameliorating a toxicity

| Symptoms related to CRS | Suggested Intervention |
|---|---|
| Fever of ≥38.3° C. | Acetaminophen (12.5 mg/kg) PO/IV up to every four hours |
| Persistent fever of ≥39° C. for 10 hours that is unresponsive to acetaminophen | Tocilizumab (8-12 mg/kg) IV |

TABLE 3-continued

Examples of interventions for treating or ameliorating a toxicity

| Symptoms related to CRS | Suggested Intervention |
| --- | --- |
| Persistent fever of ≥39° C. after tocilizumab | Dexamethasone 5-10 mg IV/PO up to every 6-12 hours with continued fevers |
| Recurrence of symptoms 48 hours after initial dose of tocilizumab | Tocilizumab (8-12 mg/kg) IV |
| Hypotension | Fluid bolus, target hematocrit >24% |
| Persistent/recurrent hypotension after initial fluid bolus (within 6 hours) | Tocilizumab (8-12 mg/kg) IV |
| Use of low dose pressors for hypotension for longer than 12 hours | Dexamethasone 5-10 mg IV/PO up to every 6 hours with continued use of pressors |
| Initiation of higher dose pressors or addition of a second pressor for hypotension | Dexamethasone 5-10 mg IV/PO up to every 6 hours with continued use of pressors |
| Initiation of oxygen supplementation | Tocilizumab (8-12 mg/kg) IV |
| Increasing respiratory support with concern for impending intubation | Dexamethasone 5-10 mg IV/PO up to every 6 hours with continued use of pressors |
| Recurrence/Persistence of symptoms for which tocilizumab was given ≥48 hours after initial dose was administered | Tocilizumab (8-12 mg/kg) IV |

In some cases, the agent or treatment is administered alone or is administered as part of a composition or formulation, such as a pharmaceutical composition or formulation, as described herein. Thus, the agent alone or as part of a pharmaceutical composition can be administered intravenously or orally, or by any other acceptable known route of administration or as described herein.

In some embodiments, the dosage of agent or the frequency of administration of the agent in a dosage regimen is reduced compared to the dosage of the agent or its frequency in a method in which a subject is treated with the agent after grade 2 or higher CRS or neurotoxicity, such as after severe, e.g., grade 3 or higher, CRS or after severe, e.g., grade 3 or higher neurotoxicity, has developed or been diagnosed (e.g. after physical signs or symptoms of grade 3 or higher CRS or neurotoxicity has manifested). In some embodiments, the dosage of agent or the frequency of administration of the agent in a dosage regimen is reduced compared to the dosage of the agent or its frequency in a method in which a subject is treated for CRS or neurotoxicity greater than 3 days, 4 days, 5 days, 6 days, 1 week, 2 weeks, three weeks, or more after administration of the immunotherapy and/or cell therapy. In some embodiments, the dosage is reduced by greater than or greater than about 1.2-fold, 1.5-fold, 2-fold, 3-fold, 4-fold, 5-fold, 6-fold, 7-fold, 8-fold, 9-fold, 10-fold or more. In some embodiments, the dosage is reduced by greater than or about 10%, 20%, 30%, 40%, 50%, 60%, 70%, 80%, 90%, or more. In some embodiments, the frequency of dosing is reduced, such as the number of daily doses is reduced or the number of days of dosing is reduced.

C. Toxicity-Targeting Agents

In some embodiments, the agent, e.g., toxicity-targeting agent, that treats and/or that prevents, delays, or attenuates the development of or risk for developing a toxicity to an immunotherapy and/or a cell therapy, is a steroid, e.g., corticosteroid. Corticosteroids typically include glucocorticoids and mineralocorticoids.

Any corticosteroid, e.g., glucocorticoid, can be used in the methods provided herein. In some embodiments, glucocorticoids include synthetic and non-synthetic glucocorticoids. Exemplary glucocorticoids include, but are not limited to: alclomethasones, algestones, beclomethasones (e.g. beclomethasone dipropionate), betamethasones (e.g. betamethasone 17-valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones and hydrocortisones (e.g. hydrocortisone acetate), cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, fluprednisolones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylprednisolones (methylprednisolone aceponate, methylprednisolone acetate, methylprednisolone hemi succinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemi succinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21-palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980).

In some examples, the glucocorticoid is selected from among cortisones, dexamethasones, hydrocortisones, methylprednisolones, prednisolones and prednisones. In a particular example, the glucocorticoid is dexamethasone.

In some embodiments, the agent is a corticosteroid and is administered in an amount that is therapeutically effective to treat, ameliorate or reduce one or more symptoms of a toxicity to an immunotherapy and/or a cell therapy, such as CRS or neurotoxicity. In some embodiments, indicators of improvement or successful treatment include determination of the failure to manifest a relevant score on toxicity grading scale (e.g. CRS or neurotoxicity grading scale), such as a score of less than 3, or a change in grading or severity on the grading scale as discussed herein, such as a change from a score of 4 to a score of 3, or a change from a score of 4 to a score of 2, 1 or 0.

In some aspects, the corticosteroid is provided in a therapeutically effective dose. Therapeutically effective concentration can be determined empirically by testing in known in vitro or in vivo (e.g. animal model) systems. For example, the amount of a selected corticosteroid to be administered to ameliorate symptoms or adverse effects of a toxicity to an immunotherapy and/or a cell therapy, such as CRS or neurotoxicity, can be determined by standard clinical techniques. In addition, animal models can be employed to help identify optimal dosage ranges. The precise dosage, which can be determined empirically, can depend on the particular therapeutic preparation, the regime and dosing schedule, the route of administration and the seriousness of the disease.

The corticosteroid can be administered in any amount that is effective to ameliorate one or more symptoms associated with the toxicity, such as with the CRS or neurotoxicity. The corticosteroid, e.g., glucocorticoid, can be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid can be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

The corticosteroid, or glucocorticoid, for example dexamethasone, can be administered orally (tablets, liquid or liquid concentrate), PO, intravenously (IV), intramuscularly or by any other known route or route described herein (e.g., with respect to pharmaceutical formulations). In some aspects, the corticosteroid is administered as a bolus, and in other aspects it may be administered over a period of time.

In some aspects, the glucocorticoid can be administered over a period of more than one day, such as over two days, over 3 days, or over 4 or more days. In some embodiments, the corticosteroid can be administered one per day, twice per day, or three times or more per day. For example, the corticosteroid, e.g., dexamethasone, may in some examples be administered at 10 mg (or equivalent) IV twice a day for three days.

In some embodiments, the dosage of corticosteroid, e.g., glucocorticoid, is administered in successively lower dosages per treatment. Hence, in some such treatment regimes, the dose of corticosteroid is tapered. For example, the corticosteroid may be administered at an initial dose (or equivalent dose, such as with reference to dexamethasone) of 4 mg, and upon each successive administration the dose may be lowered, such that the dose is 3 mg for the next administration, 2 mg for the next administration, and 1 mg for the next administration Generally, the dose of corticosteroid administered is dependent upon the specific corticosteroid, as a difference in potency exists between different corticosteroids. It is typically understood that drugs vary in potency, and that doses can therefore vary, in order to obtain equivalent effects. Table 4 shows equivalence in terms of potency for various glucocorticoids and routes of administration. Equivalent potency in clinical dosing is well known. Information relating to equivalent steroid dosing (in a non-chronotherapeutic manner) may be found in the British National Formulary (BNF) 37, March 1999.

TABLE 4

| Glucocorticoid administration | |
| --- | --- |
| Glucocorticoid (Route) | Equivalency Potency |
| Hydrocortisone (IV or PO) | 20 |
| Prednisone | 5 |
| Prednisolone (IV or PO) | 5 |
| Methylprednisolone sodium succinate (IV) | 4 |
| Dexamethasone (IV or PO) | 0.5-0.75 |

Thus, in some embodiments, the steroid is administered in an equivalent dosage amount of from or from about 1.0 mg to 20 mg dexamethasone per day, such as 1.0 mg to 15 mg dexamethasone per day, 1.0 mg to 10 mg dexamethasone per day, 2.0 mg to 8 mg dexamethasone per day, or 2.0 mg to 6.0 mg dexamethasone per day, each inclusive. In some cases, the steroid is administered in an equivalent dose of at or about 4 mg or at or about 8 mg dexamethasone per day.

In some embodiments, the steroid is administered if fever persists after treatment with tocilizumab. For example, in some embodiments, dexamethasone is administered orally or intravenously at a dosage of 5-10 mg up to every 6-12 hours with continued fevers. In some embodiments, tocilizumab is administered concurrently with or subsequent to oxygen supplementation.

In some embodiments, the agent is an inhibitor of a microglial cell activity. In some embodiments, the administration of the inhibitor modulates the activity of microglia. In some embodiments, the inhibitor is an antagonist that inhibits the activity of a signaling pathway in microglia. In some embodiments, the microglia inhibitor affects microglial homeostasis, survival, and/or proliferation. In some embodiments, the inhibitor targets the CSF1R signaling pathway. In some embodiments, the inhibitor is an inhibitor of CSF1R. In some embodiments, the inhibitor is a small molecule. In some cases, the inhibitor is an antibody.

In some aspects, administration of the inhibitor results in one or more effects selected from an alteration in microglial homeostasis and viability, a decrease or blockade of microglial cell proliferation, a reduction or elimination of microglial cells, a reduction in microglial activation, a reduction in nitric oxide production from microglia, a reduction in nitric oxide synthase activity in microglia, or protection of motor neurons affected by microglial activation. In some embodiments, the agent alters the level of a serum or blood biomarker of CSF1R inhibition, or a decrease in the level of urinary collagen type 1 cross-linked N-telopeptide (NTX) compared to at a time just prior to initiation of the administration of the inhibitor. In some embodiments, the administration of the agent transiently inhibits the activity of microglia activity and/or wherein the inhibition of microglia activity is not permanent. In some embodiments, the administration of the agent transiently inhibits the activity of CSF1R and/or wherein the inhibition of CSF1R activity is not permanent.

In some embodiments, the agent that reduces microglial cell activity is a small molecule, peptide, protein, antibody or antigen-binding fragment thereof, an antibody mimetic, an aptamer, or a nucleic acid molecule. In some embodiments, the method involves administration of an inhibitor of microglia activity. In some embodiments, the agent is an antagonist that inhibits the activity of a signaling pathway in microglia. In some embodiments, the agent that reduces microglial cell activity affects microglial homeostasis, survival, and/or proliferation.

In some embodiments, the agent that reduces microglial cell activation is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155), upregulates microRNA-124 (miR-124), inhibits nitric oxide production in microglia, inhibits nitric oxide synthase, or activates the transcription factor NRF2 (also called nuclear factor (erythroid-derived 2)-like 2, or NFE2L2).

In some embodiments, the agent that reduces microglial cell activity targets CSF1 (also called macrophage colony-stimulating factor MCSF). In some embodiments, the agent that reduces microglial cell activity affects MCSF-stimulated phosphorylation of the M-CSF receptor (Pryer et al. *Proc Am Assoc Cancer Res*, AACR Abstract nr DDT02-2 (2009)). In some cases, the agent that reduces microglial cell activity is MCS110 (international patent application publication number WO2014001802; Clinical Trial Study Record Nos.: A1 NCT00757757; NCT02807844; NCT02435680; NCT01643850).

In some embodiments, the agent that reduces microglial cell activity is a small molecule that targets the CSF1 pathway. In some embodiments, the agent is a small molecule that binds CSF1R. In some embodiments, the agent is a small molecule which inhibits CSF1R kinase activity by competing with ATP binding to CSF1R kinase. In some embodiments, the agent is a small molecule which inhibits the activation of the CFS1R receptor. In some cases, the binding of the CSF-1 ligand to the CSF1R is inhibited. In some embodiments, the agent that reduces microglial cell activity is any of the inhibitors described in U.S. Patent Application Publication Number US20160032248.

In some embodiments, the agent is a small molecule inhibitor selected from PLX-3397, PLX7486, JNJ-40346527, JNJ28312141, ARRY-382, PLX73086 (AC-708), DCC-3014, AZD6495, GW2580, Ki20227, BLZ945, PLX647, PLX5622. In some embodiments, the agent is any of the inhibitors described in Conway et al., *Proc Natl Acad Sci USA*, 102(44):16078-83 (2005); Dagher et al., *Journal of Neuroinflammation*, 12:139 (2015); Ohno et al., *Mol Cancer Ther.* 5(11):2634-43 (2006); von Tresckow et al., *Clin Cancer Res.*, 21(8) (2015); Manthey et al. *Mol Cancer Ther.* (8(11):3151-61 (2009); Pyonteck et al., *Nat Med.* 19(10): 1264-1272 (2013); Haegel et al., *Cancer Res* AACR Abstract nr 288 (2015); Smith et al., Cancer Res AACR Abstract nr 4889 (2016); Clinical Trial Study Record Nos.: NCT01525602; NCT02734433; NCT02777710; NCT01804530; NCT01597739; NCT01572519; NCT01054014; NCT01316822; NCT02880371; NCT02673736; international patent application publication numbers WO2008063888A2, WO2006009755A2, U.S. patent application publication numbers US20110044998, US 2014/0065141, and US 2015/0119267.

In some embodiments, the agent that reduces microglial cell activity is 44(2-(((1R,2R)-2-hydroxycyclohexyl)amino) benzo[d]thiazol-6-yl)oxy)-N-methylpicolinamide (BLZ945) or a pharmaceutically acceptable salt thereof or derivatives thereof. In some embodiments, the agent is the following compound:

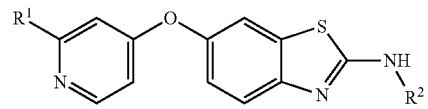

wherein R1 is an alkyl pyrazole or an alkyl carboxamide, and R2 is a hydroxycycloalkyl or a pharmaceutically acceptable salt thereof.

In some embodiments, the agent that reduces microglial cell activity is 5-((5-chloro-1H-pyrrolo[2,3-b]pyridin-3-yl) methyl)-N-((6-(trifluoromethyl)pyridin-3-yl)methyl)pyridin-2-amine, N-[5-[(5-Chloro-1H-pyrrolo[2,3-b]pyridin-3-yl)methyl]-2-pyridinyl]-6-(trifluoromethyl)-3-pyridinemethanamine) (PLX 3397) or a pharmaceutically acceptable salt thereof or derivatives thereof. In some embodiments, the agent is 5-(1H-Pyrrolo[2,3-b]pyridin-3-ylmethyl)-N-[[4-(trifluoromethyl)phenyl]methyl]-2-pyridinamine dihydrochloride (PLX647) or a pharmaceutically acceptable salt thereof or derivatives thereof. In some embodiments, the agent that reduces microglial cell activity is the following compound:

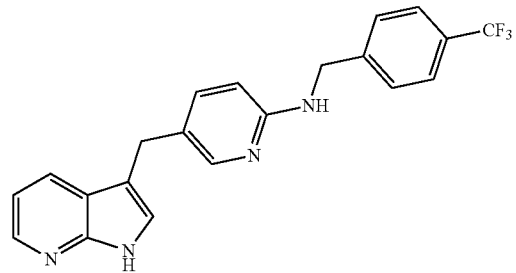 [SMILES: FC(F)(F)c1ccc(CNc2ccc(Cc3c[nH]c4ncccc34)cn2)cc1]

or a pharmaceutically acceptable salt thereof. In some embodiments, the agent that reduces microglial cell activity is the following compound:

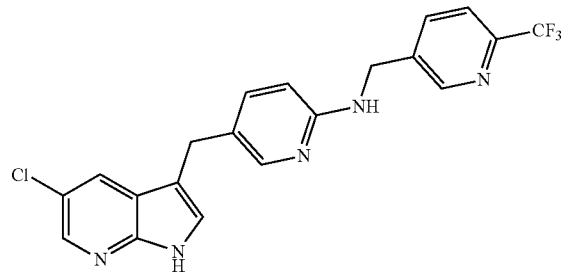 [SMILES: FC(F)(F)c1ccc(CNc2ccc(Cc3c[nH]c4ncc(Cl)cc34)cn2)cn1]

or a pharmaceutically acceptable salt thereof. In some embodiments, the agent is any of the inhibitors described in U.S. Pat. No. 7,893,075.

In some embodiments, the agent that reduces microglial cell activity is 4-cyano-N-[2-(1-cyclohexen-1-yl)-4-[1-[(dimethylamino)acetyl]-4-piperidinyl]phenyl]-1H-imidazole-2-carboxamide monohydrochloride (JNJ28312141) or a pharmaceutically acceptable salt thereof or derivatives thereof. In some embodiments, the agent is the following compound:

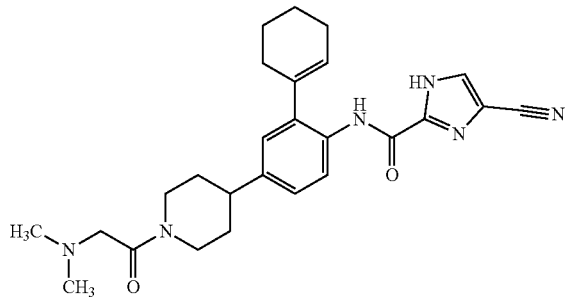 [SMILES: CN(C)CC(=O)N1CCC(c2ccc(NC(=O)c3nc(C#N)c[nH]3)c(C3=CCCCC3)c2)CC1]

or a pharmaceutically acceptable salt thereof. In some embodiments, the agent is any of the inhibitors described in U.S. Pat. No. 7,645,755.

In some embodiments, the agent that reduces microglial cell activity is 1H-Imidazole-2-carboxamide, 5-cyano-N-(2-(4,4-dimethyl-1-cyclohexen-1-yl)-6-(tetrahydro-2,2,6,6-tetramethyl-2H-pyran-4-yl)-3-pyridinyl)-, 4-Cyano-1H-imidazole-2-carboxylic acid N-(2-(4,4-dimethylcyclohex-1-enyl)-6-(2,2,6,6-tetramethyltetrahydropyran-4-yl)pyridin-3-yl)amide, 4-Cyano-N-(2-(4,4-dimethylcyclohex-1-en-1-yl)-6-(2,2,6,6-tetramethyl-tetrahydro-2H-pyran-4-yl)pyridin-3-yl)-1H-imidazole-2-carboxamide (JNJ-40346527) or a pharmaceutically acceptable salt thereof or derivatives thereof. In some embodiments, the agent is the following compound:

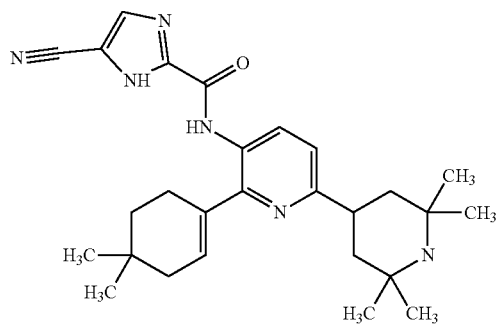 [SMILES: CC1(C)CC=C(c2nc(C3CC(C)(C)NC(C)(C)C3)ccc2NC(=O)c2ncc(C#N)[nH]2)CC1]

or a pharmaceutically acceptable salt thereof.

In another embodiment, the agent that reduces microglial cell activity is 5-(3-Methoxy-4-((4-methoxybenzyl)oxy)benzyl)pyrimidine-2,4-diamine (GW2580) or a pharmaceutically acceptable salt thereof or derivatives thereof. In some embodiments, the agent is the following compound:

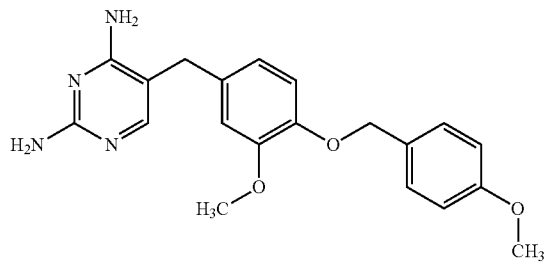 [SMILES: COc1ccc(COc2ccc(Cc3cnc(N)nc3N)cc2OC)cc1]

or a pharmaceutically acceptable salt thereof (international patent application publication number WO2009099553).

In some embodiments, the agent that reduces microglial cell activity is 4-(2,4-difluoroanilino)-7-ethoxy-6-(4-methylpiperazin-1-yl)quinoline-3-carboxamide (AZD6495) or a pharmaceutically acceptable salt thereof or derivatives thereof. In some embodiments, the agent is the following compound:

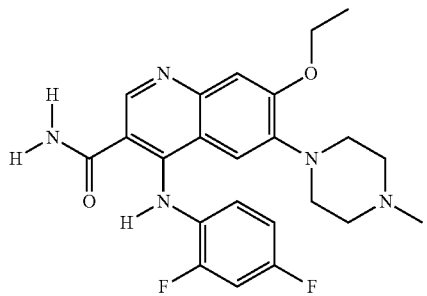 [SMILES: CCOc1cc2ncc(C(N)=O)c(Nc3ccc(F)cc3F)c2cc1N1CCN(C)CC1]

or a pharmaceutically acceptable salt thereof.

In some embodiments, the agent that reduces microglial cell activity is N-{4-[(6,7-dimethoxy-4-quinolyl)oxy]-2-methoxyphenyl}-N0-[1-(1,3-thiazole-2-yl)ethyl]urea (Ki20227) or a pharmaceutically acceptable salt thereof or derivatives thereof. In some embodiments, the agent is the following compound:

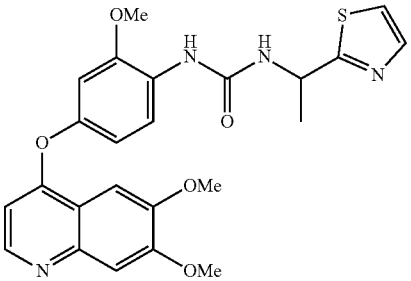 [SMILES: COc1cc(Oc2ccnc3cc(OC)c(OC)cc23)ccc1NC(=O)NC(C)c1nccs1]

or a pharmaceutically acceptable salt thereof.

In some embodiments, the agent that reduces microglial cell activation is an antibody that targets the CSF1 pathway. In some embodiments, the agent is an antibody that binds CSF1R. In some embodiments, the anti-CSF1R antibody blocks CSF1R dimerization. In some embodiments, the anti-CSF1R antibody blocks the CSF1R dimerization interface that is formed by domains D4 and D5 (Ries et al. *Cancer Cell* 25(6):846-59 (2014)). In some cases, the agent is selected from emactuzumab (RG7155; R05509554), Cabiralizumab (FPA-008), LY-3022855 (IMC-CS4), AMG- 820, TG-3003, MCS110, H27K15, 12-2D6, 2-4A5 (Rovida and Sbarba, *Clin Cell Immunol.* 6:6 (2015); Clinical Trial Study Record Nos.: NCT02760797; NCT01494688; NCT02323191; NCT01962337; NCT02471716; NCT02526017; NCT01346358; NCT02265536; NCT01444404; NCT02713529, NCT00757757; NCT02807844; NCT02435680; NCT01643850).

In some embodiments, the agent that reduces microglial cell activation is a tetracycline antibiotic. For example, the agent affects IL-1b, IL-6, TNF-α, or iNOS concentration in microglia cells (Yrjänheikki et al. *PNAS* 95(26): 15769-15774 (1998); Clinical Trial Study Record No: NCT01120899). In some embodiments, the agent is an opioid antagonist (Younger et al. *Pain Med.* 10(4):663-672 (2009.) In some embodiments, the agent reduces glutamatergic neurotransmission (U.S. Pat. No. 5,527,814). In some embodiments, the agent modulates NFkB signaling (Valera et al *J Neuroinflammation* 12:93 (2015); Clinical Trial Study Record No: NCT00231140). In some embodiments, the agent targets cannabinoid receptors (Ramirez et al. *J Neurosci* 25(8):1904-13(2005)). In some embodiments, the agent is selected from minocycline, naloxone, riluzole, lenalidomide, and a cannabinoid (optionally WIN55 or 212-2).

Nitric oxide production from microglia is believed, in some cases, to result in or increase neurotoxicity. In some embodiments, the agent modulates or inhibits nitric oxide production from microglia. In some embodiments, the agent inhibits nitric oxide synthase (NOS). In some embodiments, the NOS inhibitor is Ronopterin (VAS-203), also known as 4-amino-tetrahydrobiopterin (4-ABH4). In some embodiments, the NOS inhibitor is cindunistat, A-84643, ONO-1714, L-NOARG, NCX-456, VAS-2381, GW-273629, NXN-462, CKD-712, KD-7040, or guanidinoethyldisulfide. In some embodiments, the agent is any of the inhibitors described in Höing et al., Cell Stem Cell. 2012 Nov. 2; 11(5):620-32.

In some embodiments, the agent blocks T cell trafficking, such as to the central nervous system. In some embodiments, blocking T cell trafficking can reduce or prevent immune cells from crossing blood vessel walls into the central nervous system, including crossing the blood-brain barrier. In some cases, activated antigen-specific T cells produce proinflammatory cytokines, including IFN-γ and TNF, upon reactivation in the CNS, leading to activation of resident cells such as microglia and astrocytes. See Kivisakk et al., Neurology. 2009 Jun. 2; 72(22): 1922-1930. Thus, in some embodiments, sequestering activated T cells from microglial cells, such as by blocking trafficking and/or inhibiting the ability of such cells to cross the blood-brain barrier, can reduce or eliminate microglial activation. In some embodiments, the agent inhibits adhesion molecules on immune cells, including T cells. In some embodiments, the agent inhibits an integrin. In some embodiments, the integrin is alpha-4 integrin. In some embodiments, the agent is natalizumab (Tysabri®). In some embodiments, the agent modulates a cell surface receptor. In some embodiments, the agent modulates the sphingosine-1-phosphate (SIP) receptor, such as S1PR1 or S1PR5. In some embodiments, the agent causes the internalization of a cellular receptor, such as a sphingosine-1-phosphate (S1P) receptor, such as S1PR1 or S1PR5. In some embodiments, the agent is fingolimod (Gilenya®) or ozanimod (RPC-1063).

The transcription factor NRF2 is believed to regulate the anti-oxidant response, for example, by turning on genes that contain a cis-acting element in their promoter region. An example of such an element includes an antioxidant response element (ARE). In some embodiments, the agent activates NRF2. In some embodiments, activating NRF2 in microglial cells reduces the microglial cells' responsiveness to IFN and LPS. In some embodiments, activating NRF2 inhibits, slows, or reduces demyelination, axonal loss, neuronal death, and/or oligodendrocyte death. In some embodiments, the agent upregulates the cellular cytoprotective pathway regulated by NRF2. In some embodiments, the agent that activates NRF2 is dimethyl fumarate (Tecfidera®). In some embodiments, the agent is any of the inhibitors described in U.S. Pat. No. 8,399,514. In some embodiments, the agent is any of the inhibitors described in Höing et al., Cell Stem Cell. 2012 Nov. 2; 11(5):620-32.

In some embodiments, the agent that reduces microglial cell activation is (4S,4aS,5aR,12aS)-4,7-bis(dimethylamino)-3,10,12,12a-tetrahydroxy-1,11-dioxo-1,4,4a,5,5a,6,11,12a-octahydrotetracene-2-carboxamide (Minocycline) or a pharmaceutically acceptable salt thereof or derivatives thereof. In some embodiments, the agent is any of the compounds described in U.S. patent application publication number US20100190755. In some embodiments, the agent is the following compound:

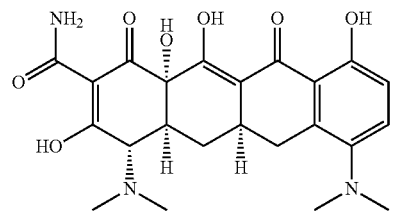 [SMILES: CN(C)c1ccc(O)c2c1C[C@H]1C[C@H]3[C@H](N(C)C)C(O)=C(C(N)=O)C(=O)[C@@]3(O)C(O)=C1C2=O]

or a pharmaceutically acceptable salt thereof.

In some embodiments, the agent that reduces microglial cell activation is 3-(7-amino-3-oxo-1H-isoindol-2-yl)piperidine-2,6-dione (lenalidomide) or a pharmaceutically acceptable salt thereof or derivatives thereof. In some embodiments, the agent is the following compound:

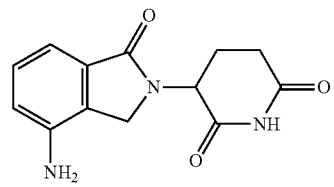 [SMILES: Nc1cccc2c1CN(C1CCC(=O)NC1=O)C2=O]

or a pharmaceutically acceptable salt thereof.

In some embodiments, the agent that reduces microglial cell activation is 4R,4aS,7aR,12bS)-4a,9-dihydroxy-3-prop-2-enyl-2,4,5,6,7a,13-hexahydro-1H-4,12-methanobenzofuro[3,2-e]isoquinoline-7-one (naloxone) or a pharmaceutically acceptable salt thereof or derivatives thereof. In some embodiments, the agent is any of the compounds described in U.S. Pat. No. 8,247,425. In some embodiments, the agent is the following compound:

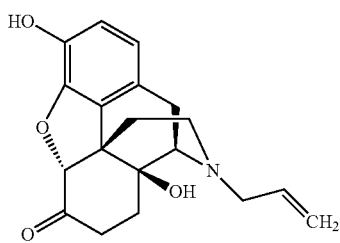 [SMILES: C=CCN1CC[C@]23c4c5ccc(O)c4O[C@H]2C(=O)CC[C@@]3(O)[C@H]1C5]

or a pharmaceutically acceptable salt thereof.

In some embodiments, the agent that reduces microglial cell activation is 2-amino-6-(trifluoromethoxy)benzothiazole, 6-(trifluoromethoxy)benzo[d]thiazol-2-amine, or 6-(trifluoromethoxy)-1,3-benzothiazol-2-amine (riluzole) or a pharmaceutically acceptable salt thereof or derivatives thereof as described in U.S. Pat. No. 5,527,814. In some embodiments, the agent is the following compound:

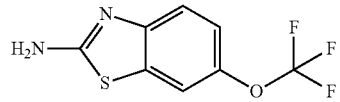

or a pharmaceutically acceptable salt thereof.

In some embodiments, the agent that reduces microglial cell activation is a modulator of a signaling pathway in microglia. In some cases, the agent reduces microglia singling. In some embodiments, the agent is a GM-CSF (CSF2) inhibitor. In other embodiments, the agent that reduces microglial cell activation is an ion channel blocker. In some specific embodiments, the agent is a calcium channel blocker. For example, in some specific examples, the agent is a dihydropyridine calcium channel blocker. In some embodiments, the agent is a microRNA inhibitor. For example, the agent targets miR-155. In some embodiments, the agent that reduces microglial cell activation is selected from MOR103, Nimodipine, IVIg, and LNA-anti-miR-155 (Butoxsky et al. *Ann Neurol.*, 77(1):75-99 (2015) and Sanz et al., *Br J Pharmacol.* 167(8): 1702-1711 (2012); Winter et al., *Ann Clin and Transl Neurol.* 2328-9503 (2016); Clinical Trial Study Record Nos.: NCT01517282, NCT00750867).

In some embodiments, the agent that reduces microglial cell activation is 3-(2-methoxyethyl) 5-propan-2-yl 2,6-dimethyl-4-(3-nitrophenyl)-1,4-dihydropyridine-3,5-dicarboxylate (nimodipine) or a pharmaceutically acceptable salt thereof or derivatives thereof. In some embodiments, the agent is any of the inhibitors described in U.S. Pat. No. 3,799,934. In some embodiments, the agent is the following compound:

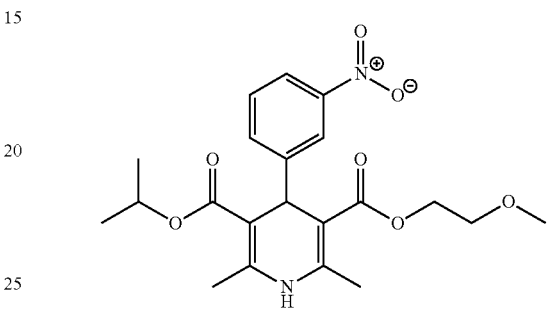

or a pharmaceutically acceptable salt thereof.

In some cases, the agent that reduces microglial cell activation is administered in a form that only affects to central nervous system and/or does not affect tumor-associated macrophages. In some embodiments, the agent promotes microglia quiescence but does not eliminate or reduce the number of microglia. In some embodiments, the method involves inhibiting microglia activity specifically in the brain such as described in Ponomarev et al., *Nature Medicine*, (1):64-70 (2011)

Exemplary agents that reduce microglial cell activation, and exemplary dosing regimens for administering such agents, are set forth in Table 5 below.

TABLE 5

Exemplary microglia inhibitors and dosage regimens

| Exemplary Inhibitor | Type of Molecule | Molecular Target(s) | Exemplary Dosing Regimen(s) |
|---|---|---|---|
| Pexidartinib (PLX3397) | small molecule | CSF1R; c-Kit; FLT3 | 200 mg tablets, twice daily for 28 days; Administer daily as split dose regimen, five dose-levels possible in dose escalation part: 400 mg 5 days on 2 days off (intermittent schedule), 400 mg, 600 mg, 800 mg or 1000 mg; 1000 mg/day for 2 weeks then 800 mg/day for 22 weeks |
| Emactuzumab (RG1755; RO5509554) | monoclonal antibody | CSF1R | 100-3000 mg once every 2 weeks |
| Cabiralizumab (FPA-008) | antibody | CSF1R | Intravenous infusion over 30 minutes every 2 weeks |
| LY-3022855 (IMC-CS4) | monoclonal antibody | CSF1R | 1.25 mg/kg intravenous delivery every 2 weeks for 6 weeks |
| JNJ-40346527 | small molecule | CSF1R | 100 mg twice daily for 12 weeks; 100-1000 mg capsule daily |
| MCS110 | antibody | MCSF (CSF1) | Up to 4 doses of 10 mg/kg MCS110 administered intravenously once every 4 weeks starting at Day 1 |
| MOR103 | antibody | GM-CSF | 6 doses of 0.5-2.0 mg/kg over 70 days |

TABLE 5-continued

Exemplary microglia inhibitors and dosage regimens

| Exemplary Inhibitor | Type of Molecule | Molecular Target(s) | Exemplary Dosing Regimen(s) |
|---|---|---|---|
| IVIg | immunoglobulin | Unknown | Intravenous infusion of 0.4 g/kg each month for 6 months |
| Minocyline | small molecule | broad spectrum antibiotic: IL-1b; IL-6, TNF-a; iNOS | Oral dose of 100 mg of minocycline twice daily for 24 months |
| Naloxone | small molecule | Opioid receptors | 4.5 mg naltrexone hydrochloride capsules once/day for 8 weeks |
| Lenalidomide/ thalidomide | small molecule | NFkB signaling | 100-400 mg daily |
| Riluzole | small molecule | Glutamate release by microglia | 50 mg twice daily |
| Cannabinoids/ cannabidiol (e.g. WIN55, 212-2) | small molecule | cannabinoid receptors | Orally 10 mg/kg/day for 6 weeks (average of 700 mg/day) |
| Dimethyl fumarate (Tecfidera ®). | small molecule | Nrf2 signaling | Starting dose of 120 mg taken orally twice/day for 7 days. Dose increased to 240 mg taken orally twice/day thereafter |
| natalizumab (Tysabri ®) | antibody | alpha-4 integrin | 300 mg infused intravenously over one hour, every four weeks |
| fingolimod (Gilenya ®) | small molecule | S1P receptors, including S1PR1 | 0.5 mg orally once-daily |
| ozanimod (RPC-1063) | small molecule | S1PR1 and S1PR5 | 0.25 mg, 0.5 mg, or 1 mg once daily |

D. Other Agents

In some embodiments, the agent or other treatment that treats or ameliorates symptoms of a toxicity of immunotherapy and/or a cell therapy, such as CRS or neurotoxicity, is one that targets a cytokine, e.g., is an antagonist or inhibitor of a cytokine, such as transforming growth factor beta (TGF-beta), interleukin 6 (IL-6), interleukin 10 (IL-10), IL-2, MIP1β (CCL4), TNF alpha, IL-1, interferon gamma (IFN-gamma), or monocyte chemoattractant protein-1 (MCP-1). In some embodiments, the agent that treats or ameliorates symptoms of a toxicity of an immunotherapy and/or a cell therapy, such as CRS or neurotoxicity, is one that targets (e.g. inhibits or is an antagonist of) a cytokine receptor, such as IL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1β receptor (e.g., CCR5), TNF alpha receptor (e.g., TNFR1), IL-1 receptor (IL1-Rα/IL-1Rβ), or IL-10 receptor (IL-10R).

The amount of a selected agent that treats or ameliorates symptoms of a toxicity of an immunotherapy and/or a cell therapy, such as CRS or neurotoxicity to be administered to ameliorate symptoms or adverse effects of a toxicity to an immunotherapy and/or a cell therapy, such as CRS or neurotoxicity, can be determined by standard clinical techniques. Exemplary adverse events include, but are not limited to, an increase in alanine aminotransferase, an increase in aspartate aminotransferase, chills, febrile neutropenia, headache, hypotension, left ventricular dysfunction, encephalopathy, hydrocephalus, seizure, and/or tremor.

In some embodiments, the agent is administered in a dosage amount of from or from about 30 mg to 5000 mg, such as 50 mg to 1000 mg, 50 mg to 500 mg, 50 mg to 200 mg, 50 mg to 100 mg, 100 mg to 1000 mg, 100 mg to 500 mg, 100 mg to 200 mg, 200 mg to 1000 mg, 200 mg to 500 mg or 500 mg to 1000 mg.

In some embodiments, the agent is administered from or from about 0.5 mg/kg to 100 mg/kg, such as from or from about 1 mg/kg to 50 mg/kg, 1 mg/kg to 25 mg/kg, 1 mg/kg to 10 mg/kg, 1 mg/kg to 5 mg/kg, 5 mg/kg to 100 mg/kg, 5 mg/kg to 50 mg/kg, 5 mg/kg to 25 mg/kg, 5 mg/kg to 10 mg/kg, 10 mg/kg to 100 mg/kg, 10 mg/kg to 50 mg/kg, 10 mg/kg to 25 mg/kg, 25 mg/kg to 100 mg/kg, 25 mg/kg to 50 mg/kg to 50 mg/kg to 100 mg/kg. In some embodiments, the agent is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive. In some aspects, the agent is administered in a dosage amount of at least or at least about or about 1 mg/kg, 2 mg/kg, 4 mg/kg, 6 mg/kg, 8 mg/kg, 10 mg/kg or more. In some embodiments, the agent is administered at a dose of 4 mg/kg or 8 mg/kg.

In some embodiments, the agent is administered by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

In some embodiments, the amount of the agent is administered about or approximately twice daily, daily, every other day, three times a week, weekly, every other week or once a month.

In some embodiments, the agent is administered as part of a composition or formulation, such as a pharmaceutical composition or formulation as described below. Thus, in some cases, the composition comprising the agent is administered as described below. In other aspects, the agent is administered alone and may be administered by any known acceptable route of administration or by one described herein, such as with respect to compositions and pharmaceutical formulations.

In some embodiments, the agent that treats or ameliorates symptoms of a toxicity of the immunotherapy and/or cell therapy, such as CRS or neurotoxicity, is an antibody or antigen binding fragment. In some embodiments, the agent is tocilizumab, siltuximab, sarilumab, olokizumab (CDP6038), elsilimomab, ALD518/BMS-945429, sirukumab (CNTO 136), CPSI-2634, ARGX-109, FE301, or FM101.

In some embodiments, the agent is an antagonist or inhibitor of IL-6 or the IL-6 receptor (IL-6R). In some aspects, the agent is an antibody that neutralizes IL-6 activity, such as an antibody or antigen-binding fragment that binds to IL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-IL-6 antibody, such as siltuximab, elsilimomab, ALD518/BMS-945429, sirukumab (CNTO 136), CPSI-2634, ARGX-109, FE301, FM101, or olokizumab (CDP6038). In some aspects, the agent may neutralize IL-6 activity by inhibiting the ligand-receptor interactions. The feasibility of this general type of approach has been demonstrated with a natural occurring receptor antagonist for interleukin-1. See Harmurn, C. H. et al., Nature (1990) 343:336-340. In some aspects, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, the agent is tocilizumab. In some embodiments, tocilizumab is administered as an early intervention in accord with the provided methods a dosage of from or from about 1 mg/kg to 12 mg/kg, such as at or about 4 mg/kg, 8 mg/kg, or 10 mg/kg. In some embodiments, tocilizumab is administered by intravenous infusion. In some embodiments, tocilizumab is administered for a persistent fever of greater than 39° C. lasting 10 hours that is unresponsive to acetaminophen. In some embodiments, a second administration of tocilizumab is provided if symptoms recur after 48 hours of the initial dose.

In some embodiments, the agent is an agonist or stimulator of TGF-β or a TGF-β receptor (e.g., TGF-β receptor I, II, or III). In some aspects, the agent is an antibody that increases TGF-β activity, such as an antibody or antigen-binding fragment that binds to TGF-β or one of its receptors. In some embodiments, the agent that is an agonist or stimulator of TGF-β and/or its receptor is a small molecule, a protein or peptide, or a nucleic acid.

In some embodiments, the agent is an antagonist or inhibitor of MCP-1 (CCL2) or a MCP-1 receptor (e.g., MCP-1 receptor CCR2 or CCR4). In some aspects, the agent is an antibody that neutralizes MCP-1 activity, such as an antibody or antigen-binding fragment that binds to MCP-1 or one of its receptors (CCR2 or CCR4). In some embodiments, the MCP-1 antagonist or inhibitor is any described in Gong et al. J Exp Med. 1997 Jul. 7; 186(1): 131-137 or Shahrara et al. J Immunol 2008; 180:3447-3456. In some embodiments, the agent that is an antagonist or inhibitor of MCP-1 and/or its receptor (CCR2 or CCR4) is a small molecule, a protein or peptide, or a nucleic acid.

In some embodiments, the agent is an antagonist or inhibitor of IFN-γ or an IFN-γ receptor (IFNGR). In some aspects, the agent is an antibody that neutralizes IFN-γ activity, such as an antibody or antigen-binding fragment that binds to IFN-γ or its receptor (IFNGR). In some aspects, the IFN-gamma neutralizing antibody is any described in Dobber et al. Cell Immunol. 1995 February; 160(2):185-92 or Ozmen et al. J Immunol. 1993 Apr. 1; 150(7):2698-705. In some embodiments, the agent that is an antagonist or inhibitor of IFN-γ/IFNGR is a small molecule, a protein or peptide, or a nucleic acid.

In some embodiments, the agent is an antagonist or inhibitor of IL-10 or the IL-10 receptor (IL-10R). In some aspects, the agent is an antibody that neutralizes IL-10 activity, such as an antibody or antigen-binding fragment that binds to IL-10 or IL-10R. In some aspects, the IL-10 neutralizing antibody is any described in Dobber et al. Cell Immunol. 1995 February; 160(2):185-92 or Hunter et al. J Immunol. 2005 Jun. 1; 174(11):7368-75. In some embodiments, the agent that is an antagonist or inhibitor of IL-10/IL-10R is a small molecule, a protein or peptide, or a nucleic acid.

In some embodiments, the agent is an antagonist or inhibitor of IL-1 or the IL-1 receptor (IL-1R). In some aspects, the agent is an IL-1 receptor antagonist, which is a modified form of IL-1R, such as anakinra (see, e.g., Fleischmann et al., (2006) Annals of the rheumatic diseases. 65(8):1006-12). In some aspects, the agent is an antibody that neutralizes IL-1 activity, such as an antibody or antigen-binding fragment that binds to IL-1 or IL-1R, such as canakinumab (see also EP 2277543). In some embodiments, the agent that is an antagonist or inhibitor of IL-1/IL-1R is a small molecule, a protein or peptide, or a nucleic acid.

In some embodiments, the agent is an antagonist or inhibitor of a tumor necrosis factor (TNF) or a tumor necrosis factor receptor (TNFR). In some aspects, the agent is an antibody that blocks TNF activity, such as an antibody or antigen-binding fragment that binds to a TNF, such as TNFα, or its receptor (TNFR, e.g., TNFRp55 or TNFRp75). In some aspects, the agent is selected from among infliximab, adalimumab, certolizumab pegol, golimumab and etanercept. In some embodiments, the agent that is an antagonist or inhibitor of TNF/TNFR is a small molecule, a protein or peptide, or a nucleic acid. In some embodiments, the agent is a small molecule that affects TNF, such as lenalidomide (see, e.g., Muller et al. (1999) Bioorganic & Medicinal Chemistry Letters. 9 (11):1625).

In some embodiments, the agent is an antagonist or inhibitor of signaling through the Janus kinase (JAK) and two Signal Transducer and Activator of Transcription (STAT) signaling cascade. JAK/STAT proteins are common components of cytokine and cytokine receptor signaling. In some embodiments, the agent that is an antagonist or inhibitor of JAK/STAT, such as ruxolitinib (see, e.g., Mesa et al. (2012) Nature Reviews Drug Discovery. 11(2):103-104), tofacitinib (also known as Xeljanz, Jakvinus tasocitinib and CP-690550), Baricitinib (also known as LY-3009104, INCB-28050), Filgotinib (G-146034, GLPG-0634), Gandotinib (LY-2784544), Lestaurtinib (CEP-701), Momelotinib (GS-0387, CYT-387), Pacritinib (SB1518), and Upadacitinib (ABT-494). In some embodiments, the agent is a small molecule, a protein or peptide, or a nucleic acid.

In some embodiments, the agent is a kinase inhibitor. In some embodiments, the agent is an inhibitor of Bruton's tyrosine kinase (BTK). In some embodiments, the inhibitor is or comprises ibrutinib or acalabrutinib (see, e.g., Barrett et al., ASH 58th Annual Meeting San Diego, Calif. Dec. 3-6, 2016, Abstract 654; Ruella et al., ASH 58th Annual Meeting San Diego, Calif. Dec. 3-6, 2016, Abstract 2159). In some embodiments, the agent is an inhibitor as described in U.S.

Pat. Nos. 7,514,444; 8,008,309; 8,476,284; 8,497,277; 8,697,711; 8,703,780; 8,735,403; 8,754,090; 8,754,091; 8,957,079; 8,999,999; 9,125,889; 9,181,257; or 9,296,753.

In some embodiments, a device, such as absorbent resin technology with blood or plasma filtration, can be used to reduce cytokine levels. In some embodiments, the device used to reduce cytokine levels is a physical cytokine absorber, such as an extracorporeal cytokine absorber. In some embodiments, a physical cytokine absorber can be used to eliminate cytokines from the bloodstream in an ex vivo, extracorporeal manner. In some embodiments, the agent is a porous polymer. In some embodiments, the agent is CytoSorb (see, e.g., Basu et al. Indian J Crit Care Med. (2014) 18(12): 822-824).

III. CELL THERAPY AND ENGINEERING CELLS

In some embodiments, the cell therapy, e.g. T cell therapy, for use in accord with the provided methods and articles of manufacture includes administering a therapeutic cell composition containing engineered cells expressing recombinant receptors designed to recognize and/or specifically bind to molecules associated with the disease or condition and result in a response, such as an immune response against such molecules upon binding to such molecules. In some embodiments, the articles of manufacture contain a cell therapy containing a dose or composition of genetically engineered cells expressing a recombinant receptor, and instructions for administering the cell therapy following or based on the results of an assessment, in a biological sample (e.g. apheresis or leukapheresis sample) of the presence or percentage or number of cells of a myeloid cell population or of a level of expression of a marker (e.g. CD14) expressed by cells of said population or of a myeloid marker. The receptors may include chimeric receptors, e.g., chimeric antigen receptors (CARs), and other transgenic antigen receptors including transgenic T cell receptors (TCRs).

In some embodiments, the cells contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or CD8+ or CD4+ cells are enriched or selected. Among the compositions are pharmaceutical compositions and formulations for administration, such as for adoptive cell therapy. Also provided are therapeutic methods for administering the cells and compositions to subjects, e.g., patients.

Thus, in some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

A. Recombinant Receptors

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

1. Chimeric Antigen Receptors (CARs)

In some embodiments, engineered cells, such as T cells, are provided that express a CAR with specificity for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as chimeric receptor, contains an intracellular signaling region, which includes a cytoplasmic signaling domain (also interchangeably called an intracellular signaling domain), such as a cytoplasmic (intracellular) region capable of inducing a primary activation signal in a T cell, for example, a cytoplasmic signaling domain of a T cell receptor (TCR) component (e.g. a cytoplasmic signaling domain of a zeta chain of a CD3-zeta (CD3ξ) chain or a functional variant or signaling portion thereof) and/or that comprises an immunoreceptor tyrosine-based activation motif (ITAM).

In some embodiments, the chimeric receptor further contains an extracellular ligand-binding domain that specifically binds to a ligand (e.g. antigen) antigen. In some embodiments, the chimeric receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MEW) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the antibody or antigen-binding portion thereof is expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR. In some embodiments, the extracellular antigen binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the recombinant receptor, such as a chimeric receptor (e.g. CAR), includes a ligand-binding domain that binds, such as specifically binds, to an antigen (or a ligand). Among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the CAR contains an antibody or an antigen-binding fragment (e.g. scFv) that specifically recognizes an antigen, such as an intact antigen, expressed on the surface of a cell.

In some embodiments, the antigen (or a ligand) is a tumor antigen or cancer marker. In some embodiments, the antigen (or a ligand) is or includes Receptor tyrosine kinase like orphan receptor 1 (ROR1), B cell maturation antigen (BCMA), carbonic anhydrase 9 (CA9, also known as G250 or CAIX), Her2/neu (receptor tyrosine kinase erb-B2), CD19, CD20, CD22, and hepatitis B surface antigen, anti-folate receptor, CD23, CD24, CD30, CD33, CD38, CD44, chondroitin sulfate proteoglycan 4 (CSPG4), epidermal growth factor protein (EGFR), epithelial glycoprotein 2 (EPG-2), epithelial glycoprotein 40 (EPG-40), ephrinB2, ephrin receptor A2 (EPHa2), Her3 (erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, glypican-3 (GPC3), G Protein Coupled Receptor 5D (GPCR5D), Human high molecular weight-melanoma-associated antigen (HMW-MAA), IL-22 receptor alpha(IL-22Rα or IL-22R-alpha), IL-13 receptor alpha 2 (IL-13Rα2 or IL-13R-alpha2), kinase insert domain receptor (kdr), kappa light chain, Leucine Rich Repeat Containing 8 Family Member A (LRRC8A), Lewis Y, L1-cell adhesion molecule, (L1-CAM), Melanoma-associated antigen (MAGE)-A1, MAGE-A3, MAGE-A6, MAGE-A10, Preferentially expressed antigen of melanoma (PRAME), survivin, TAG72, B7-H3, B7-H6, IL-13 receptor alpha 2 (IL-13Rα2), CD171, Human leukocyte antigen A1 (HLA-AI), Human leukocyte antigen A2 (HLA-A2), folate receptor-alpha, CD44v6, CD44v7/8, αvβ6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, dual antigen, a cancer-testes antigen, mesothelin (MSLN), murine cytomegalovirus (CMV), mucin 1 (MUC1), MUC16, prostate specific antigen, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), oncofetal antigen, tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific or pathogen-expressed antigen and an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the antigen is a pathogen-specific antigen. In some embodiments, the antigen is a viral antigen (such as a viral antigen from HIV, HCV, HBV, etc.), bacterial antigens, and/or parasitic antigens.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a WIC-peptide complex. In some embodiments, an antibody or antigen-binding portion thereof that recognizes an WIC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

In some embodiments the scFv is derived from FMC63. FMC63 is a mouse monoclonal IgG1 antibody raised against Nalm-1 and -16 cells expressing CD19 of human origin (Ling, N. R., et al. (1987). Leucocyte typing III. 302). The FMC63 antibody comprises CDRH1 and H2 set forth in SEQ ID NOS: 43 and 44 respectively, and CDRH3 set forth in SEQ ID NOS: 45 or 59 and CDRL1 set forth in SEQ ID NOS: 40 and CDR L2 set forth in SEQ ID NOS: 41 or 60 and CDR L3 set forth in SEQ ID NOS: 42 or 61. The FMC63 antibody comprises the heavy chain variable region ($V_H$) comprising the amino acid sequence of SEQ ID NO: 46 and the light chain variable region ($V_L$) comprising the amino acid sequence of SEQ ID NO: 47. In some embodiments, the svFv comprises a variable light chain containing the CDRL1 set forth in SEQ ID NO: 40, a CDRL2 set forth in SEQ ID NO: 41 or 60, and a CDRL3 set forth in SEQ ID NO: 42 or 61 and/or a variable heavy chain containing a CDRH1 set forth in SEQ ID NO:43, a CDRH2 set forth in SEQ ID NO:44, and a CDRH3 set forth in SEQ ID NO:45 or 59. In some embodiments, the scFv comprises a variable heavy chain region of FMC63 set forth in SEQ ID NO:46 and a variable light chain region of FMC63 set forth in SEQ ID NO: 47. In some embodiments, the variable heavy and variable light chain are connected by a linker. In some embodiments, the linker is set forth in SEQ ID NO:29. In some embodiments, the scFv comprises, in order, a VH, a linker, and a VL. In some embodiments, the scFv comprises, in order, a VL, a linker, and a VH. In some embodiments, the svFc is encoded by a sequence of nucleotides set forth in SEQ ID NO:30 or a sequence that exhibits at least 85%, 86%, 87%, 88%, 89%, 90%, 91%, 92%, 93%, 94%, 95%, 96%, 97%, 98%, or 99% sequence identity to SEQ ID NO:30. In some embodiments, the scFv comprises the sequence of amino acids set forth in SEQ ID NO:48 or a sequence that exhibits at least 85%, 86%, 87%, 88%, 89%, 90%, 91%, 92%, 93%, 94%, 95%, 96%, 97%, 98%, or 99% sequence identity to SEQ ID NO:48.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III.* 302). The SJ25C1 antibody comprises CDRH1, H2 and H3 set forth in SEQ ID NOS: 52-54, respectively, and CDRL1, L2 and L3 sequences set forth in SEQ ID NOS: 49-51, respectively. The SJ25C1 antibody comprises the heavy chain variable region ($V_H$) comprising the amino acid sequence of SEQ ID NO: 55 and the light chain variable region ($V_L$) comprising the amino acid sequence of SEQ ID NO: 56. In some embodiments, the svFv comprises a variable light chain containing the CDRL1 set forth in SEQ ID NO: 49, a CDRL2 set forth in SEQ ID NO: 50, and a CDRL3 set forth in SEQ ID NO:51 and/or a variable heavy chain containing a CDRH1 set forth in SEQ ID NO:52, a CDRH2 set forth in SEQ ID NO: 53, and a CDRH3 set forth in SEQ ID NO:54. In some embodiments, the scFv comprises a variable heavy chain region of SJ25C1 set forth in SEQ ID NO:55 and a variable light chain region of SJ25C1 set forth in SEQ ID NO: 56. In some embodiments, the variable heavy and variable light chains are connected by a linker. In some embodiments, the linker is set forth in SEQ ID NO:57. In some embodiments, the scFv comprises, in order, a VH, a linker, and a VL. In some embodiments, the scFv comprises, in order, a VL, a linker, and a VH. In some embodiments, the scFv comprises the sequence of amino acids set forth in SEQ ID NO:58 or a sequence that exhibits at least 85%, 86%, 87%, 88%, 89%, 90%, 91%, 92%, 93%, 94%, 95%, 96%, 97%, 98%, or 99% sequence identity to SEQ ID NO:58. Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MEW class I molecules are heterodimers having a membrane spanning a chain, in some cases with three a domains, and a non-covalently associated β2 microglobulin. Generally, MHC class II molecules are composed of two transmembrane glycoproteins, α and β, both of which typically span the membrane. An WIC molecule can include an effective portion of an MHC that contains an antigen binding site or sites for binding a peptide and the sequences necessary for recognition by the appropriate antigen receptor. In some embodiments, WIC class I molecules deliver peptides originating in the cytosol to the cell surface, where a MHC-peptide complex is recognized by T cells, such as generally $CD8^+$ T cells, but in some cases CD4+ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human WIC can also be referred to as human leukocyte antigen (HLA).

The term "MHC-peptide complex" or "peptide-WIC complex" or variations thereof, refers to a complex or association of a peptide antigen and an WIC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an WIC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the WIC Class II complex. In some embodiments, a peptide has a length of from or from about 8 to 13 amino acids for recognition in the MHC Class I complex. In some embodiments, upon recognition of the peptide in the context of an WIC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by methods known in the art (see e.g. US Published Application Nos. US 2002/0150914; US 2003/0223994; US 2004/0191260; US 2006/0034850; US 2007/00992530; US20090226474; US20090304679; and International PCT Publication No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US published application No. US20020150914, US2014/0294841; and Cohen C J. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some aspects, the chimeric antigen receptor includes an extracellular portion containing the antibody or fragment and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a $C_H1/C_L$ and/or Fc region. In some embodiments, the recombinant receptor further comprises a spacer and/or a hinge region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.,* 19:3153 or international patent application publication number WO2014031687. In some embodiments, the spacer has the sequence set forth in SEQ ID NO: 1, and is encoded by the sequence set forth in SEQ ID NO: 2. In some embodiments, the spacer has the sequence set forth in SEQ ID NO: 3. In some embodiments, the spacer has the sequence set forth in SEQ ID NO: 4.

In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 and 5. In some embodiments, the spacer has the sequence set forth in SEQ ID NOS: 31-39. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 31-39.

The antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen binding component (e.g., antibody) is linked to one or more transmembrane and intracellular signaling regions. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling region are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the ROR1-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ξ) or Fc receptor γ and CD8, CD4, CD25 or CD16.

In some embodiments, upon ligation of the CAR, the cytoplasmic domain or intracellular signaling region of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling region of an antigen receptor component or costimulatory molecule is used in place of an intact immunostimulatory chain, for example, if it transduces the effector function signal. In some embodiments, the intracellular signaling regions, e.g., comprising intracellular domain or domains, include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma or FcR beta. In some embodiments, cytoplasmic signaling molecule(s) in the CAR contain(s) a cytoplasmic signaling domain, portion thereof, or sequence derived from CD3 zeta.

In some embodiments, the CAR includes a signaling region and/or transmembrane portion of a costimulatory receptor, such as CD28, 4-1BB, OX40, DAP10, and ICOS. In some aspects, the same CAR includes both the signaling region and costimulatory components.

In some embodiments, the signaling region is included within one CAR, whereas the costimulatory component is provided by another CAR recognizing another antigen. In some embodiments, the CARs include activating or stimulatory CARs, and costimulatory CARs, both expressed on the same cell (see WO2014/055668).

In certain embodiments, the intracellular signaling region comprises a CD28 transmembrane and signaling domain linked to a CD3 (e.g., CD3-zeta) intracellular domain. In some embodiments, the intracellular signaling region comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain disposed between the extracellular domain and the intracellular signaling region.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 4-1BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 4-1BB.

In some embodiments, the intracellular signaling region comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular region comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling region comprises a human CD3 chain, optionally a CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190 or 8,911,993. In some embodiments, the intracellular signaling region comprises the sequence of amino acids set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO:1. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO:3. In some embodiments, the spacer is an Ig hinge, e.g., an IgG4 hinge, linked to a $C_H3$ domain only, such as set forth in SEQ ID NO:4. In some embodiments, the spacer is or comprises a glycine-serine rich sequence or other flexible linker such as known flexible linkers.

2. T Cell Receptor

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MEW molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or $C_β$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ξ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPred1 (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known to those of skill in the art. For predicting MHC class I binding sites, such models include, but are not limited to, ProPred1 (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known to those of skill in the art, See e.g., Soo Hoo, W. F. et al. PNAS (USA) 89, 4759 (1992); Wülfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula —P-AA-P— wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula —PGGG-(SGGGG)5-P— wherein P is proline, G is glycine and S is serine (SEQ ID NO:16). In some embodiments, the linker has the sequence GSADDAKKDAAKKDGKS (SEQ ID NO:17)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other WIC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

3. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in PCT Pub. No. WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, and/or ICOS. In some embodiments, the first and second receptors include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

B. Nucleic Acids and Vectors

Also provided are one or more polynucleotides (e.g., nucleic acid molecules) encoding recombinant receptors, vectors for genetically engineering cells to express receptors and methods for producing the engineered cells.

Also provided are sets or combinations of polynucleotides. Also provided are compositions containing such set or combination of polynucleotides. In some embodiments, the set or combination of polynucleotides, are used together for engineering of cells. In some embodiments, the first and the second polynucleotides in the set are introduced simultaneously or sequentially, in any order into a cell for engineering.

In other aspects, the signal sequence may encode a heterologous or non-native signal peptide, such as the exemplary signal peptide of the GMCSFR alpha chain set forth in SEQ ID NO: 25 and encoded by the nucleotide sequence set forth in SEQ ID NO:24. In some cases, the nucleic acid sequence encoding the recombinant receptor, e.g., chimeric antigen receptor (CAR) contains a signal sequence that encodes a signal peptide. Non-limiting exemplary examples of signal peptides include, for example, the GMCSFR alpha chain signal peptide set forth in SEQ ID NO: 25 and encoded by the nucleotide sequence set forth in SEQ ID NO:24, or the CD8 alpha signal peptide set forth in SEQ ID NO:26.

In certain cases where nucleic acid molecules encode two or more different polypeptide chains, each of the polypeptide chains can be encoded by a separate nucleic acid molecule. For example, two separate nucleic acids are provided, and each can be individually transferred or introduced into the cell for expression in the cell.

In some embodiments, such as those where the polynucleotide contains a first and second nucleic acid sequence, the coding sequences encoding each of the different polypeptide chains can be operatively linked to a promoter, which can be the same or different. In some embodiments, the nucleic acid molecule can contain a promoter that drives the expression of two or more different polypeptide chains. In some embodiments, such nucleic acid molecules can be multicistronic (bicistronic or tricistronic, see e.g., U.S. Pat. No. 6,060,273). In some embodiments, transcription units can be engineered as a bicistronic unit containing an IRES (internal ribosome entry site), which allows coexpression of gene products by a message from a single promoter. Alternatively, in some cases, a single promoter may direct expression of an RNA that contains, in a single open reading frame (ORF), two or three genes separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as a T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Various 2A elements are known. Examples of 2A sequences that can be used in the methods and system disclosed herein, without limitation, 2A sequences from the foot-and-mouth disease virus (F2A, e.g., SEQ ID NO: 23), equine rhinitis A virus (E2A, e.g., SEQ ID NO: 22), Thosea asigna virus (T2A, e.g., SEQ ID NO: 6 or 18), and porcine teschovirus-1 (P2A, e.g., SEQ ID NO: 20 or 21) as described in U.S. Patent Publication No. 20070116690.

In some embodiments, the vector contains a nucleic acid sequence encoding one or more marker(s). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, an E2A or an F2A. Extrinsic marker genes may in some cases be utilized in connection with engineered cell to permit detection or selection of cells and, in some cases, also to promote cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO: 7) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the nucleic acid encoding the marker is operably linked to a polynucleotide encoding for a linker sequence, such as a cleavable linker sequence, e.g., a T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7.

Also provided are vectors or constructs containing such nucleic acids and/or polynucleotides. In some embodiments, the vectors or constructs contain one or more promoters operatively linked to the nucleic acid encoding the recombinant receptor to drive expression thereof. In some embodiments, the promoter is operatively linked to one or more than one nucleic acid molecules or polynucleotides. Thus, also provided are vectors, such as those that contain any of the polynucleotides provided herein.

In some cases, the vector is a viral vector, such as a retroviral vector, e.g., a lentiviral vector or a gammaretroviral vector. Also provided a set or combination of vectors. In some embodiments, the set or combination of vectors comprises a first vector and a second vector. Also provided are compositions containing such set or combination of vectors. In some embodiments, the set or combination of vectors, are used together for engineering of cells. In some embodiments, the first and the second vectors in the set are introduced simultaneously or sequentially, in any order into a cell for engineering.

In some embodiments, the vectors include viral vectors, e.g., retroviral or lentiviral, non-viral vectors or transposons, e.g. Sleeping Beauty transposon system, vectors derived from simian virus 40 (SV40), adenoviruses, adeno-associated virus (AAV), lentiviral vectors or retroviral vectors, such as gamma-retroviral vectors, retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV) or adeno-associated virus (AAV).

C. Cells and Preparation of Cells for Engineering

Provided herein are cells, such as engineered cells that contain a recombinant receptor. Also provided are populations of such cells, compositions containing such cells and/or enriched for such cells, such as in which cells expressing the recombinant receptor, e.g. chimeric receptor, make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are methods for engineering, producing or generating such cells, therapeutic methods for administering the cells and compositions to subjects, e.g., patients, and methods for detecting, selecting, isolating or separating such cells.

Thus, provided are genetically engineered cells expressing the recombinant receptors e.g., CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In some embodiments, the cell is a regulatory T cell (Treg). In some embodiments, the cell further comprises a recombinant FOXP3 or variant thereof.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for engineering may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) *Blood.* 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or ROR1, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are $CD45RO^-$, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are $CD62L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotec, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain aspects, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International PCT Publication No. WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) *Blood.* 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10:1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant receptor, e.g., CAR.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling region of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

D. Methods for Genetic Engineering

Various methods for the introduction of genetically engineered components, such as recombinant receptors, e.g., CARs or TCRs, are well known and may be used with the provided methods and compositions. Exemplary methods include those for transfer of nucleic acids encoding the polypeptides or receptors, including via viral vectors, e.g., retroviral or lentiviral, non-viral vectors or transposons, e.g. Sleeping Beauty transposon system. Methods of gene transfer can include transduction, electroporation or other method that results into gene transfer into the cell.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, it may be desired to safeguard against the potential that overexpression of a stimulatory factor (for example, a lymphokine or a cytokine) could potentially result in an unwanted outcome or lower efficacy in a subject, such as a factor associated with toxicity in a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) *Blood.* 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl* Acids 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion, e.g. with nucleic acids encoding a recombinant receptor, e.g., a T cell receptor (TCR) or a chimeric antigen receptor (CAR). This transfection for the introduction of the gene of the desired polypeptide or receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.*, 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

As described above, in some embodiments, the cells are incubated and/or cultured prior to or in connection with genetic engineering. The incubation steps can include culture, cultivation, stimulation, activation, propagation and/or freezing for preservation, e.g. cryopreservation.

IV. METHODS OF ASSESSING, ADMINISTRATION AND TREATMENT

Provided herein are articles of manufacture, kits and methods involving reagents that are capable of detecting or that are specific for a population of myeloid cells or a marker expressed on a population of myeloid cells for use in conjunction with a cell therapy (e.g. CAR+ T cells) and/or agents for treating a toxicity, including for use as a companion diagnostic and/or in prophylactic treatment methods in connection with adoptive cell therapy. In some embodiments, the provided articles of manufacture and methods are associated with reducing the risk of developing a toxicity, such as a severe toxicity, e.g. severe neurotoxicity, in subjects administered a cell therapy, such as a CAR+ T cell therapy.

A. Method of Treatment

Provided are methods of assessing myeloid markers and articles of manufacture, including using and uses in the treatment of diseases, conditions, and disorders in which the antigen recognized by the recombinant receptor (e.g. CAR) is expressed. Provided are articles of manufacture containing a cell therapy containing a dose or composition of genetically engineered cells expressing a recombinant receptor, and instructions for administering the cell therapy following or based on the results of an assessment, in a biological sample (e.g. apheresis or leukapheresis sample) of the presence or percentage or number of cells of a myeloid cell population or of a level of expression of a marker (e.g. CD14) expressed by cells of said population or of a myeloid marker. In some embodiments, the administered cells express a recombinant receptor, e.g., CAR. In some embodiments, the methods of treatment involve administering any of the engineered cells provided herein, or any of the compositions provided herein, to a subject. In addition, the method further includes providing an intervention such as any that are described in Section II.B.

Provided herein are methods of assessing a risk of toxicity (e.g. neurotoxicity or severe neurotoxicity) by assaying an apheresis sample from a subject for the presence or percentage or number of cells of a myeloid cell population or of cells positive for a marker expressed by cells of said population or positive for expression of a myeloid marker. In some embodiments, the method of assessing then includes, following or based on the results of the assay, determining if the subject is at risk of developing neurotoxicity (e.g. severe neurotoxicity) following administration of a cell therapy, in a subject is a candidate for treatment with the cell therapy. In some embodiments, the assessing is performed on an apheresis sample that is obtained from the subject prior to administering the cell therapy and/or said apheresis sample does not comprise the recombinant receptor and/or said engineered cells. In some embodiments, the subject is assessed as at risk of developing neurotoxicity or severe neurotoxicity if the percentage or number of cells in the sample positive for the myeloid marker, and/or percentage or number of cells of the population of myeloid cells in the sample, is at or above a threshold level. In some embodiments, the percentage is a percentage of the myeloid cell population or of cells positive for the myeloid marker among total leukocytes or total CD45+ cells, or viable cells thereof, in the sample. In some cases, the percentage is a percentage of the myeloid cell population or cells positive for the myeloid marker among total leukocytes or CD45+ cells, or viable cells thereof, in the sample. In some examples, the percentage is a percentage of CD14+ cells among total leukocytes or CD45+ cells.

In some embodiments, the method of assessing further includes monitoring the subject after administration of the cell therapy for development of a sign or symptom of a neurotoxicity other than fever. In some cases, based on the results of the assessment, the method further includes administering to the subject the agent or other treatment capable of treating, preventing, delaying, reducing or attenuating the development or risk of development of a neurotoxicity (i) prior to, (ii) within one, two, or three days of, (iii) concurrently with and/or (iv) at first fever following, the initiation of administration of the cell therapy to the subject; administering to the subject the cell therapy at a reduced dose or at a dose that is not associated with risk of developing neurotoxicity or severe neurotoxicity, or is not associated with a risk of developing a neurotoxicity or severe neurotoxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

In some embodiments, the methods includes comparing the percentage or number of cells in the sample positive for the marker, to a threshold level. In some embodiments, the subject is assessed as not suspected to be at risk or as not likely to be at risk of developing neurotoxicity or severe neurotoxicity if the percentage or number of cells in the sample positive for the marker, and/or percentage or number of cells of the population of myeloid cells in the sample, is below a threshold level. In some cases, if the subject is not assessed as being at risk for developing neurotoxicity or severe neurotoxicity, the subject is not further administered, prior to or concurrently with administering the cell therapy and/or prior to the development of a sign or symptom of a neurotoxicity other than fever, an agent or treatment capable of treating, preventing, delaying, or attenuating the development of the neurotoxicity; or the method further comprises administering the cell therapy to the subject on an outpatient setting and/or without admission of the subject to the hospital overnight or for one or more consecutive days and/or is without admission of the subject to the hospital for one or more days. In some aspects, the assessing is performed as part of or prior to treatment with the cell therapy.

Also provided are methods for selecting a subject for treatment including contacting a biological sample (e.g. apheresis or leukapheresis sample) with a reagent capable of detecting or that is specific for a population of myeloid cells or a marker expressed on a population of myeloid cells (e.g. CD14). In some embodiments of the method, the biological sample is from a subject that is a candidate for treatment with a cell therapy containing a dose or composition of genetically engineered cells expressing a recombinant receptor and the biological sample is obtained from the subject prior to administering the cell therapy and/or said biological sample does not comprise the recombinant receptor and/or said engineered cells.

In some embodiments, methods and article manufacture further include instructions for administering the cell therapy to the subject. In some cases, the instructions specify, for example, that if the percentage or number of cells in the sample positive for the marker, and/or percentage or number of cells of the population in the sample, is at or above a threshold level, an agent or other treatment capable of treating, preventing, delaying, reducing or attenuating the development or risk of development of a toxicity is administered to the subject (i) prior to, (ii) within one, two, or three days of, (iii) concurrently with and/or (iv) at first fever following, the initiation of administration of the cell therapy to the subject. In some embodiments, the percentage is a percentage of the myeloid cell population or of cells positive for the myeloid marker among total leukocytes or total CD45+ cells, or viable cells thereof, in the sample. In some cases, the percentage is a percentage of the myeloid cell population or cells positive for the myeloid marker among total leukocytes or CD45+ cells, or viable cells thereof, in the sample. In some examples, the percentage is a percentage of CD14+ cells among total leukocytes or CD45+ cells. In some cases, the instructions specify administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy if the percentage or number of cells in the sample positive for the marker, and/or percentage or number of cells of the population in the sample, is at or above a threshold level. Further, in some embodiments, the instructions specify administering to the subject the cell therapy in an in-patient setting and/or with admission to the hospital for one or more days, optionally wherein the cell therapy is otherwise to be administered to subjects on an outpatient basis or without admission to the hospital for one or more days if the percentage or number of cells in the sample positive for the marker, and/or percentage or number of cells of the population in the sample, is at or above a threshold level. In some embodiments, the instructions further specify that if the number or percentage of cells in the sample positive for the marker, and/or percentage or number of cells of the population in the sample, is below a threshold level, a cell therapy, optionally at a non-reduced dose, optionally on an outpatient basis or without admission to the hospital for one or more days is administered to the subject.

In some embodiments, the toxicity is neurotoxicity. In some cases, the neurotoxicity is severe neurotoxicity (e.g. grade 3 or higher neurotoxicity).

In some embodiments, the instructions further specify, if the number or percentage of cells in the sample positive for the marker, and/or percentage or number of cells of the population in the sample, is below a threshold level, administering to the subject the cell therapy, optionally at a non-reduced dose, optionally on an outpatient basis or without admission to the hospital for one or more days. If the number or percentage of cells in the sample positive for the marker, and/or percentage or number of cells of the population in the sample, is below a threshold level, in some embodiments, the administration of the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

Also provided is a method of monitoring a subject following administration of the cell therapy. In some embodiments, the method includes observing a subject administered a cell therapy for the development of a sign or symptom of a neurotoxicity or severe neurotoxicity other than fever, wherein the subject is one that has been determined to be at risk of, or likely to be at risk of, developing neurotoxicity or severe neurotoxicity as determined based on assaying a biological sample from the patient by detecting a population of myeloid cells or a marker expressed by myeloid cells. In some embodiments, the apheresis sample is obtained from the subject prior to the administration of the cell therapy. In some embodiments, the monitoring is on a subject that has been administered the cell therapy in an in-patient setting and/or with admission to the hospital for one or more days or is admitted to the hospital during the period or a portion of the period of the observation.

Also provided is method of prophylactic treatment including administering, to a subject, an agent or other treatment capable of treating, preventing, delaying, reducing or attenuating the development or risk of development of a toxicity. In some embodiments of the method, the subject is a candidate for treatment optionally with a cell therapy, said cell therapy optionally comprising a dose or composition of genetically engineered cells expressing a recombinant receptor for treating a disease or condition; and the subject has been identified as at risk for developing a toxicity following or based on the results of an assay, of a biological sample from a subject, for the presence or percentage or number of cells of a myeloid cell population or of a level of expression of a marker expressed by cells of said population or of a myeloid marker, said biological sample obtained from the subject prior to administering the cell therapy and/or said biological sample not comprising the recombinant receptor and/or said engineered cells.

In some cases, the cell therapy is administered following or based on the results of an assessment, in a biological sample (e.g. apheresis or leukapheresis sample) of the presence or percentage or number of cells of a myeloid cell population or of a level of expression of a marker (e.g. CD14) expressed by cells of said population or of a myeloid marker. For example, the assessment includes detection such as by contacting a reagent capable of directly or indirectly detecting myeloid cells or a marker expressed on a population of myeloid cells with the biological sample and determining the percentage or number of cells positive for, optionally surface positive for, the marker and/or level in the biological sample. In some embodiments, a threshold level is determined based on the percentage or number of cells in the sample positive for the marker, and/or percentage or number of cells of the population in the sample, positive for the marker. In some aspects, the threshold level is a percent of cells surface positive for the marker in the biological sample or blood or apheresis sample that is or is about 20%, 25%, 30%, 35%, 40%, 45%, 50%, 55% or 60%. In some cases, the threshold level is a percent of cells surface positive for the myeloid marker in the biological sample that is or is about 50%, 55% or 60%.

In some cases, the threshold level is the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

Provided are articles of manufacture containing the engineered cells or methods of administering the engineered cells and compositions, and uses of such engineered cells and compositions to treat or prevent diseases, conditions, and disorders, including cancers. In some embodiments, the engineered cells and compositions are administered to a subject or patient having the particular disease or condition to be treated, e.g., via adoptive cell therapy, such as adoptive T cell therapy. In some embodiments, provided cells and compositions are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

The disease or condition that is treated in some aspects can be any in which expression of an antigen is associated with, specific to, and/or expressed on a cell or tissue of a disease, disorder or condition and/or involved in the etiology of a disease, condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the immunomodulatory polypeptide and/or recombinant receptor, e.g., the chimeric antigen receptor or TCR, specifically binds to an antigen associated with the disease or condition. In some embodiments, the subject has a disease, disorder or condition, optionally a cancer, a tumor, an autoimmune disease, disorder or condition, or an infectious disease.

In some embodiments, the disease, disorder or condition includes tumors associated with various cancers. The cancer can in some embodiments be any cancer located in the body of a subject, such as, but not limited to, cancers located at the head and neck, breast, liver, colon, ovary, prostate, pancreas, brain, cervix, bone, skin, eye, bladder, stomach, esophagus, peritoneum, or lung. For example, the anti-cancer agent can be used for the treatment of colon cancer, cervical cancer, cancer of the central nervous system, breast cancer, bladder cancer, anal carcinoma, head and neck cancer, ovarian cancer, endometrial cancer, small cell lung cancer, non-small cell lung carcinoma, neuroendocrine cancer, soft tissue carcinoma, penile cancer, prostate cancer, pancreatic cancer, gastric cancer, gall bladder cancer or esophageal cancer. In some cases, the cancer can be a cancer of the blood. In some embodiments, the disease, disorder or condition is a tumor, such as a solid tumor, lymphoma, leukemia, blood tumor, metastatic tumor, or other cancer or tumor type. In some embodiments, the disease, disorder or condition is selected from among cancers of the colon, lung, liver, breast, prostate, ovarian, skin, melanoma, bone, brain cancer, ovarian cancer, epithelial cancers, renal cell carcinoma, pancreatic adenocarcinoma, cervical carcinoma, colorectal cancer, glioblastoma, neuroblastoma, Ewing sarcoma, medulloblastoma, osteosarcoma, synovial sarcoma, and/or mesothelioma.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CIVIL), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM), a B cell malignancy is selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of receptor tyrosine kinase like orphan receptor 1 (ROR1), B cell maturation antigen (BCMA), carbonic anhydrase 9 (CA9, also known as G250 or CAIX), Her2/neu (receptor tyrosine kinase erb-B2), CD19, CD20, CD22, and hepatitis B surface antigen, anti-folate receptor, CD23, CD24, CD30, CD33, CD38, CD44, chondroitin sulfate proteoglycan 4 (CSPG4), epidermal growth factor protein (EGFR), epithelial glycoprotein 2 (EPG-2), epithelial glycoprotein 40 (EPG-40), ephrinB2, ephrin receptor A2 (EPHa2), Her3

(erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, glypican-3 (GPC3), G Protein Coupled Receptor 5D (GPCR5D), Human high molecular weight-melanoma-associated antigen (HMW-MAA), IL-22 receptor alpha(IL-22Rα or IL-22R-alpha), IL-13 receptor alpha 2 (IL-13Rα2 or IL-13R-alpha2), kinase insert domain receptor (kdr), kappa light chain, Leucine Rich Repeat Containing 8 Family Member A (LRRC8A), Lewis Y, L1-cell adhesion molecule, (L1-CAM), Melanoma-associated antigen (MAGE)-A1, MAGE-A3, MAGE-A6, MAGE-A10, Preferentially expressed antigen of melanoma (PRAME), survivin, TAG72, B7-H3, B7-H6, IL-13 receptor alpha 2 (IL-13Rα2), CD171, Human leukocyte antigen A1 (HLA-AI), Human leukocyte antigen A2 (HLA-A2), folate receptor-alpha, CD44v6, CD44v7/8, αvβ6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, dual antigen, a cancer-testes antigen, mesothelin (MSLN), murine cytomegalovirus (CMV), mucin 1 (MUC1), MUC16, prostate specific antigen, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), oncofetal antigen, tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific or pathogen-expressed antigen and an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

As used herein, a "subject" is a mammal, such as a human or other animal, and typically is human. In some embodiments, the subject, e.g., patient, to whom the immunomodulatory polypeptides, engineered cells, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or engineered cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the immunomodulatory polypeptides or engineered cells administered. In some embodiments, the provided methods involve administering the immunomodulatory polypeptides, engineered cells, or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The provided methods and uses include methods and uses for adoptive cell therapy. In some embodiments, the methods include administration of the engineered cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or super type as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

B. Dosing

In some embodiments, a dose of cells is administered to subjects in accord with the provided methods. In some embodiments, the size or timing of the doses is determined as a function of the particular disease or condition in the subject. In some cases, the size or timing of the doses for a particular disease in view of the provided description may be empirically determined.

In some embodiments, the dose of cells comprises between at or about $2\times10^5$ of the cells/kg and at or about $2\times10^6$ of the cells/kg, such as between at or about $4\times10^5$ of the cells/kg and at or about $1\times10^6$ of the cells/kg or between at or about $6\times10^5$ of the cells/kg and at or about $8\times10^5$ of the cells/kg. In some embodiments, the dose of cells comprises no more than $2\times10^5$ of the cells (e.g. antigen-expressing, such as CAR-expressing cells) per kilogram body weight of the subject (cells/kg), such as no more than at or about $3\times10^5$ cells/kg, no more than at or about $4\times10^5$ cells/kg, no more than at or about $5\times10^5$ cells/kg, no more than at or about $6\times10^5$ cells/kg, no more than at or about $7\times10^5$ cells/kg, no more than at or about $8\times10^5$ cells/kg, no more than at or about $9\times10^5$ cells/kg, no more than at or about $1\times10^6$ cells/kg, or no more than at or about $2\times10^6$ cells/kg. In some embodiments, the dose of cells comprises at least or at least about or at or about $2\times10^5$ of the cells (e.g. antigen-expressing, such as CAR-expressing cells) per kilogram body weight of the subject (cells/kg), such as at least or at least about or at or about $3\times10^5$ cells/kg, at least or at least about or at or about $4\times10^5$ cells/kg, at least or at least about or at or about $5\times10^5$ cells/kg, at least or at least about or at or about $6\times10^5$ cells/kg, at least or at least about or at or about $7\times10^5$ cells/kg, at least or at least about or at or about $8\times10^5$ cells/kg, at least or at least about or at or about $9\times10^5$ cells/kg, at least or at least about or at or about $1\times10^6$ cells/kg, or at least or at least about or at or about $2\times10^6$ cells/kg.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose includes fewer than about $1\times10^8$ total recombinant receptor (e.g., CAR)-expressing cells, T cells, or peripheral blood mononuclear cells (PBMCs), e.g., in the range of about $1\times10^6$ to $1\times10^8$ such cells, such as $2\times10^6$, $5\times10^6$, $1\times10^7$, $5\times10^7$, or $1\times10^8$ or total such cells, or the range between any two of the foregoing values. In some embodiments, where the subject is a human, the dose includes between about $1\times10^6$ and $3\times10^8$ total recombinant receptor (e.g., CAR)-expressing cells, e.g., in the range of about $1\times10^7$ to $2\times10^8$ such cells, such as $1\times10^7$, $5\times10^7$, $1\times10^8$ or $1.5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^5$ to $5\times10^8$ total recombinant receptor-expressing T cells or total T cells, $1\times10^5$ to $1\times10^8$ total recombinant receptor-expressing T cells or total T cells, from or from about $5\times10^5$ to $1\times10^7$ total recombinant receptor-expressing T cells or total T cells, or from or from about $1\times10^6$ to $1\times10^7$ total recombinant receptor-expressing T cells or total T cells, each inclusive.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose.

Thus, the dose of cells may be administered as a split dose, e.g., a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include $CD8^+$ and $CD4^+$ T cells, respectively, and/or CD8+- and CD4+-enriched populations, respectively, e.g., CD4+ and/or CD8+ T cells each individually including cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ cells expressing a recombinant receptor to CD8+ cells expressing a recombinant receptor and/or of CD4+ cells to CD8+ cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+CD4+:CAR+CD8+ ratio, e.g., 1:1) involves the administration of a cell composition containing one of the populations and then administration of a separate cell composition comprising the other of the populations, where the administration is at or approximately at the target or desired ratio.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, the methods also include administering one or more additional doses of cells expressing a chimeric antigen receptor (CAR) and/or lymphodepleting therapy, and/or one or more steps of the methods are repeated. In some embodiments, the one or more additional dose is the same as the initial dose. In some embodiments, the one or more additional dose is different from the initial dose, e.g., higher, such as 2-fold, 3-fold, 4-fold, 5-fold, 6-fold, 7-fold, 8-fold, 9-fold or 10-fold or more higher than the initial dose, or lower, such as e.g., higher, such as 2-fold, 3-fold, 4-fold, 5-fold, 6-fold, 7-fold, 8-fold, 9-fold or 10-fold or more lower than the initial dose. In some embodiments, administration of one or more additional doses is determined based on response of the subject to the initial treatment or any prior treatment, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose includes fewer than about $1 \times 10^8$ total recombinant receptor (e.g., CAR)-expressing cells, T cells, or peripheral blood mononuclear cells (PBMCs), e.g., in the range of about $1 \times 10^6$ to $1 \times 10^8$ such cells, such as $2 \times 10^6$, $5 \times 10^6$, $1 \times 10^7$, $5 \times 10^7$, or $1 \times 10^8$ or total such cells, or the range between any two of the foregoing values.

In some embodiments, the dose of genetically engineered cells comprises from or from about $1 \times 10^5$ to $5 \times 10^8$ total CAR-expressing T cells, $1 \times 10^5$ to $2.5 \times 10^8$ total CAR-expressing T cells, $1 \times 10^5$ to $1 \times 10^8$ total CAR-expressing T cells, $1 \times 10^5$ to $5 \times 10^7$ total CAR-expressing T cells, $1 \times 10^5$ to $2.5 \times 10^7$ total CAR-expressing T cells, $1 \times 10^5$ to $1 \times 10^7$ total CAR-expressing T cells, $1 \times 10^5$ to $5 \times 10^6$ total CAR-expressing T cells, $1 \times 10^5$ to $2.5 \times 10^6$ total CAR-expressing T cells, $1 \times 10^5$ to $1 \times 10^6$ total CAR-expressing T cells, $1 \times 10^6$ to $5 \times 10^8$ total CAR-expressing T cells, $1 \times 10^6$ to $2.5 \times 10^8$ total CAR-expressing T cells, $1 \times 10^6$ to $1 \times 10^8$ total CAR-expressing T cells, $1 \times 10^6$ to $5 \times 10^7$ total CAR-expressing T cells, $1 \times 10^6$ to $2.5 \times 10^7$ total CAR-expressing T cells, $1 \times 10^6$ to $1 \times 10^7$ total CAR-expressing T cells, $1 \times 10^6$ to $5 \times 10^6$ total CAR-expressing T cells, $1 \times 10^6$ to $2.5 \times 10^6$ total CAR-expressing T cells, $2.5 \times 10^6$ to $5 \times 10^8$ total CAR-expressing T cells, $2.5 \times 10^6$ to $2.5 \times 10^8$ total CAR-expressing T cells, $2.5 \times 10^6$ to $1 \times 10^8$ total CAR-expressing T cells, $2.5 \times 10^6$ to $5 \times 10^7$ total CAR-expressing T cells, $2.5 \times 10^6$ to $2.5 \times 10^7$ total CAR-expressing T cells, $2.5 \times 10^6$ to $1 \times 10^7$ total CAR-expressing T cells, $2.5 \times 10^6$ to $5 \times 10^6$ total CAR-expressing T cells, $5 \times 10^6$ to $5 \times 10^8$ total CAR-expressing T cells, $5 \times 10^6$ to $2.5 \times 10^8$ total CAR-expressing T cells, $5 \times 10^6$ to $1 \times 10^8$ total CAR-expressing T cells, $5 \times 10^6$ to $5 \times 10^7$ total CAR-expressing T cells, $5 \times 10^6$ to $2.5 \times 10^7$ total CAR-expressing T cells, $5 \times 10^6$ to $1 \times 10^7$ total CAR-expressing T cells, $1 \times 10^7$ to $5 \times 10^8$ total CAR-expressing T cells, $1 \times 10^7$ to $2.5 \times 10^8$ total CAR-expressing T cells, $1 \times 10^7$ to $1 \times 10^8$ total CAR-expressing T cells, $1 \times 10^7$ to $5 \times 10^7$ total CAR-expressing T cells, $1 \times 10^7$ to $2.5 \times 10^7$ total CAR-expressing T cells, $2.5 \times 10^7$ to $5 \times 10^8$ total CAR-expressing T cells, $2.5 \times 10^7$ to $2.5 \times 10^8$ total CAR-expressing T cells, $2.5 \times 10^7$ to $1 \times 10^8$ total CAR-expressing T cells, $2.5 \times 10^7$ to $5 \times 10^7$ total CAR-expressing T cells, $5 \times 10^7$ to $5 \times 10^8$ total CAR-expressing T cells, $5 \times 10^7$ to $2.5 \times 10^8$ total CAR-expressing T cells, $5 \times 10^7$ to $1 \times 10^8$ total CAR-expressing T cells, $1 \times 10^8$ to $5 \times 10^8$ total CAR-expressing T cells, $1 \times 10^8$ to $2.5 \times 10^8$ total CAR-expressing T cells, or $2.5 \times 10^8$ to $5 \times 10^8$ total CAR-expressing T cells.

In some embodiments, the dose of genetically engineered cells comprises at least or at least about $1 \times 10^5$ CAR-expressing cells, at least or at least about $2.5 \times 10^5$ CAR-expressing cells, at least or at least about $5 \times 10^5$ CAR-expressing cells, at least or at least about $1 \times 10^6$ CAR-expressing cells, at least or at least about $2.5 \times 10^6$ CAR-expressing cells, at least or at least about $5 \times 10^6$ CAR-expressing cells, at least or at least about $1 \times 10^7$ CAR-expressing cells, at least or at least about $2.5 \times 10^7$ CAR-expressing cells, at least or at least about $5 \times 10^7$ CAR-expressing cells, at least or at least about $1 \times 10^8$ CAR-expressing cells, at least or at least about $2.5 \times 10^8$ CAR-expressing cells, or at least or at least about $5 \times 10^8$ CAR-expressing cells.

In some embodiments, the cell therapy comprises administration of a dose comprising a number of cell from or from about $1 \times 10^5$ to $5 \times 10^8$ total recombinant receptor-expressing cells, total T cells, or total peripheral blood mononuclear cells (PBMCs), from or from about $5 \times 10^5$ to $1 \times 10^7$ total recombinant receptor-expressing cells, total T cells, or total peripheral blood mononuclear cells (PBMCs) or from or from about $1 \times 10^6$ to $1 \times 10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1 \times 10^5$ total recombinant receptor-expressing cells, total T cells, or total peripheral blood mononuclear cells (PBMCs), such at least or at least $1 \times 10^6$, at least or at least about $1 \times 10^7$, at least or at least about $1 \times 10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1 \times 10^5$ to $5 \times 10^8$ CD3+ or CD8+ total T cells or CD3+ or CD8+ recombinant receptor-expressing cells, from or from about $5 \times 10^5$ to $1 \times 10^7$ CD3+ or CD8+ total T cells or CD3+ or CD8+ recombinant receptor-expressing cells, or from or from about $1 \times 10^6$ to $1 \times 10^7$ CD3+ or CD8+ total T cells or CD3+ or CD8+ recombinant receptor-expressing cells, each inclusive. In some embodiments, the cell therapy comprises administration of a dose comprising a number of cell from or from about $1 \times 10^5$ to $5 \times 10^8$ total CD3+/CAR+ or CD8+/CAR+ cells, from or from about $5 \times 10^5$ to $1 \times 10^7$ total CD3+/CAR+ or CD8+/CAR+ cells, or from or from about $1 \times 10^6$ to $1 \times 10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1 \times 10^6$ and $5 \times 10^8$ total recombinant receptor (e.g., CAR)-expressing CD8+ cells, e.g., in the range of about $5 \times 10^6$ to $1 \times 10^8$ such cells, such cells $1 \times 10^7$, $2.5 \times 10^7$, $5 \times 10^7$, $7.5 \times 10^7$, $1 \times 10^8$, or $5 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1 \times 10^7$ to $0.75 \times 10^8$ total recombinant receptor-expressing CD8+ T cells, $1 \times 10^7$ to $2.5 \times 10^7$ total recombinant receptor-expressing CD8+ T cells, from or from about $1 \times 10^7$ to $0.75 \times 10^8$ total recombinant receptor-expressing CD8+ T cells, each inclusive. In some embodiments, the dose of cells comprises the administration of or about $1 \times 10^7$, $2.5 \times 10^7$, $5 \times 10^7$ $7.5 \times 10^7$, $1 \times 10^8$, or $5 \times 10^8$ total recombinant receptor-expressing CD8+ T cells.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the size of the dose is determined by the burden of the disease or condition in the subject. For example, in some aspects, the number of cells administered in the dose is determined based on the tumor burden that is present in the subject immediately prior to administration of the initiation of the dose of cells. In some embodiments, the size of the first and/or subsequent dose is inversely correlated with disease burden. In some aspects, as in the context of a large disease burden, the subject is administered a low number of cells. In other embodiments, as in the context of a lower disease burden, the subject is administered a larger number of cells.

In some embodiments, the dose is determined based on the results of an assay, of a biological sample from a subject, for the presence or percentage or number of cells of a myeloid cell population or of a level of expression of a marker expressed by cells of said population or of a myeloid marker. In some cases, based on the results of the assay, a subject is administered a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy.

In some embodiments, the cell therapy comprises the administration of no more than $1 \times 10^8$ total recombinant receptor-expressing cells, total T cells, or total peripheral blood mononuclear cells (PBMCs), no more than $1 \times 10^7$ total recombinant receptor-expressing cells, total T cells, or total peripheral blood mononuclear cells (PBMCs), no more than $0.5 \times 10^7$ total recombinant receptor-expressing cells, total T cells, or total peripheral blood mononuclear cells (PBMCs), no more than $1 \times 10^6$ total recombinant receptor-expressing cells, total T cells, or total peripheral blood mononuclear cells (PBMCs), no more than $0.5 \times 10^6$ total recombinant receptor-expressing cells, total T cells, or total peripheral blood mononuclear cells (PBMCs). In some cases where a reduced dose or a dose that is not associated with risk of developing toxicity or severe toxicity is or contains less than or less than about $5 \times 10^7$ total recombinant receptor-expressing cells, optionally CAR+ cells, total T cells, or total peripheral blood mononuclear cells (PBMCs), such as less than or less than about $2.5 \times 10^7$, less than or less than about $1.0 \times 10^7$, less than or less than about $5.0 \times 10^6$, less than or less than about $1.0 \times 10^6$, less than or less than about $5.0 \times 10^5$, or less than or less than about $1 \times 10^5$ total recombinant receptor-expressing cells, optionally CAR+ cells, total T cells, or total peripheral blood mononuclear cells (PBMCs).

In some examples, the dose that is not associated with risk of developing toxicity or severe toxicity is or comprises from or from about $1 \times 10^5$ to $5 \times 10^7$ total recombinant receptor-expressing cells, optionally CAR+ cells, total T cells, or total peripheral blood mononuclear cells (PBMCs), such as $1 \times 10^5$ to $2.5 \times 10^7$, $1 \times 10^5$ to $1.0 \times 10^7$, $1 \times 10^5$ to $5.0 \times 10^6$, $1 \times 10^5$ to $1.0 \times 10^6$, $1.0 \times 10^5$ to $5.0 \times 10^5$, $5.0 \times 10^5$ to $5 \times 10^7$, $5 \times 10^5$ to $2.5 \times 10^7$, $5 \times 10^5$ to $1.0 \times 10^7$, $5 \times 10^5$ to $5.0 \times 10^6$, $5 \times 10^5$ to $1.0 \times 10^6$, $1.0 \times 10^6$ to $5 \times 10^7$, $1 \times 10^6$ to $2.5 \times 10^7$, $1 \times 10^6$ to $1.0 \times 10^7$, $1 \times 10^6$ to $5.0 \times 10^6$, $5.0 \times 10^6$ to $5 \times 10^7$, $5 \times 10^6$ to $2.5 \times 10^7$, $5 \times 10^6$ to $1.0 \times 10^7$, $1.0 \times 10^7$ to $5 \times 10^7$, $1 \times 10^7$ to $2.5 \times 10^7$ or $2.5 \times 10^7$ to $5 \times 10^7$ total recombinant receptor-expressing cells, optionally CAR+ cells, total T cells, or total peripheral blood mononuclear cells (PBMCs).

In some embodiments, the one or more additional therapeutic agents include a cytokine, such as IL-2, for example, to enhance persistence. In some embodiments, the methods comprise administration of a chemotherapeutic agent. In some embodiments, the one or more additional therapeutic agents include one or more lymphodepleting therapies, such as prior to or simultaneous with initiation of administration of the engineered cells. In some embodiments, the lymphodepleting therapy comprises administration of a phosphamide, such as cyclophosphamide. In some embodiments, the lymphodepleting therapy can include administration of fludarabine. In some embodiments, fludarabine is excluded in the lymphodepleting therapy. In some embodiments, a lymphodepleting therapy is not administered.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered recombinant receptor, such as CAR or TCR, expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

V. ARTICLES OF MANUFACTURE

Provided are articles of manufacture containing the regents described above and instructions for use are provided. The articles of manufacture relate to a reagent capable of detecting or that is specific for a population of myeloid cells or a marker expressed on a population of myeloid cells (e.g. CD14). In some embodiments, the reagent detects a marker that is a myeloid cell marker, such as a human myeloid cell marker, such as a monocyte marker, e.g., a human monocyte marker. In some aspects, the monocyte marker is a marker present on, e.g., on the surface of, all or most monocytes or most monocyte populations, optionally in a human or in a healthy individual. In some aspects, the monocyte marker is not present on or is not ordinarily expressed on populations of cells other than myeloid cells or other than monocytes, such as is not present on lymphocytes and/or is not expressed on neutrophils. In some aspects, the monocyte marker is a marker that is co-expressed or substantially co-expressed with, or that has a coextensive or essentially coextensive expression pattern, CD14 in human cells and/or has a similar or essentially the same expression pattern as CD14 in humans.

In some embodiments, instructions are provided for using the reagent to assay a biological sample from a subject that is a candidate for treatment, optionally with a cell therapy, said cell therapy optionally including a dose or composition of genetically engineered cells expressing a recombinant receptor.

In some embodiments, provided are articles of manufacture that include a dose or composition of genetically engineered cells expressing a recombinant receptor, and instructions for administering the cell therapy following or based on the results of an assessment, in a biological sample (e.g. apheresis or leukapheresis sample) of the presence or percentage or number of cells of a myeloid cell population or of a level of expression of a marker (e.g. CD14) expressed by cells of said population or of a myeloid marker. In some embodiments, the article of manufacture includes a composition comprising a therapeutically effective amount of any of the engineered cells described herein, and instructions for administering, to a subject for treating a disease or condition.

Further provided are articles of manufacture containing an agent capable of treating, preventing, delaying, reducing or attenuating the development or risk of development of a toxicity, and instructions for administering the agent following or based on the results of an assessment in a biological sample of the presence or percentage or number of cells of a myeloid cell population or of a level of expression of a marker expressed by cells of said population or of a myeloid marker.

The articles of manufacture provided may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition.

In some embodiments of the article of manufacture, instructions are also provided. The instructions specify, for example, that if the percentage or number of cells in the sample positive for the marker, and/or percentage or number of cells of the population in the sample, is at or above a threshold level, an agent or other treatment capable of treating, preventing, delaying, reducing or attenuating the development or risk of development of a toxicity is administered to the subject (i) prior to, (ii) within one, two, or three days of, (iii) concurrently with and/or (iv) at first fever following, the initiation of administration of the cell therapy to the subject.

In some cases, the instructions specify administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy if the percentage or number of cells in the sample positive for the marker, and/or percentage or number of cells of the population in the sample, is at or above a threshold level. Further, in some embodiments, the instructions specify administering to the subject the cell therapy in an in-patient setting and/or with admission to the hospital for one or more days, optionally wherein the cell therapy is otherwise to be administered to subjects on an outpatient basis or without admission to the hospital for one or more days if the percentage or number of cells in the sample positive for the marker, and/or percentage or number of cells of the population in the sample, is at or above a threshold level.

In some embodiments, the instructions further specify that if the number or percentage of cells in the sample positive for the marker, and/or percentage or number of cells of the population in the sample, is below a threshold level, a cell therapy, optionally at a non-reduced dose, optionally on an outpatient basis or without admission to the hospital for one or more days is administered to the subject.

In some aspects, the instructions are for administering the cell therapy and optionally one or more other agents or treatments for treating, preventing, delaying, reducing or attenuating the development or risk of development of a toxicity, based on detection of a marker (e.g. CD14) in a biological sample obtained from the subject prior to administering the cell therapy. In some embodiments, the marker detected is a myeloid cell marker, such as a human myeloid cell marker, such as a monocyte marker, e.g., a human monocyte marker. In some aspects, the monocyte marker is a marker present on, e.g., on the surface of, all or most monocytes or most monocyte populations, optionally in a human or in a healthy individual. In some aspects, the monocyte marker is not present on or is not ordinarily expressed on populations of cells other than myeloid cells or other than monocytes, such as is not present on lymphocytes and/or is not expressed on neutrophils. In some aspects, the monocyte marker is a marker that is co-expressed or substantially co-expressed with, or that has a coextensive or essentially coextensive expression pattern, CD14 in human cells and/or has a similar or essentially the same expression pattern as CD14 in humans. In some embodiments, the instructions specify if the percentage of cells positive for the myeloid marker is below the threshold level, administering to the subject the cell therapy, optionally at a non-reduced dose, optionally on an outpatient basis or without admission to the hospital for one or more days is administered to the subject. In some aspects, the administration of the cell therapy does not include administering, prior to or concurrently with administering the cell therapy and/or prior to the development of a sign or symptom of a toxicity other than fever, an agent or treatment capable of treating, preventing, delaying, or attenuating the development of the toxicity. In some cases, the instructions specify the cell therapy is to be or may be administered to the subject on an outpatient setting and/or without admission of the subject to the hospital overnight or for one or more consecutive days and/or is without admission of the subject to the hospital for one or more days.

In some examples, the articles of manufacture may further contain one or more therapeutic agents. In some embodiments, the therapeutic agent is an immunomodulatory agent, a cytotoxic agent, an anti-cancer agent or a radiotherapeutic.

The articles of manufacture may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

VI. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, a "subject" is a mammal, such as a human or other animal, and typically is human. In some embodiments, the subject, e.g., patient, to whom the immunomodulatory polypeptides, engineered cells, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or engineered cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the immunomodulatory polypeptides or engineered cells administered. In some embodiments, the provided methods involve administering the immunomodulatory polypeptides, engineered cells, or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

VII. EXEMPLARY EMBODIMENTS

Among the exemplary embodiments are:

1. An article of manufacture comprising a reagent capable of detecting or that is specific for a population of myeloid cells or a marker expressed on a population of myeloid cells, and instructions for using the reagent to assay a biological sample from a subject that is a candidate for treatment, optionally with a cell therapy, said cell therapy optionally comprising a dose or composition of genetically engineered cells expressing a recombinant receptor.

2. The article of manufacture of embodiment 1, wherein the population of cells is or comprises monocytes.

3. The article of manufacture of embodiment 1 or embodiment 2, wherein the marker is a myeloid cell marker and/or wherein the marker is CD14 and/or wherein the population of cells is or comprises CD14+ myeloid cells.

4. The article of manufacture of any of embodiments 1-3, wherein the marker is human, optionally human CD14.

5. The article of manufacture of any of embodiments 1-4, wherein the reagent is a binding molecule that specifically binds to the marker or cells of the myeloid cell population.

6. The article of manufacture of any of embodiments 1-5, wherein the reagent is an antibody or an antigen-binding fragment thereof.

7. The article of manufacture of any of embodiments 1-6, wherein the biological sample is or is obtained from a blood, plasma or serum sample.

8. The article of manufacture of any of embodiments 1-7, wherein the biological sample is or is obtained from an apheresis or leukapheresis sample.

9. The article of manufacture of any of embodiments 1-8, further comprising the cell therapy and/or further comprising instructions for use with, prior to and/or in connection with treatment with the cell therapy.

10. The article of manufacture of any of embodiments 1-9, further comprising one or more agents or treatments for treating, preventing, delaying, reducing or attenuating the development or risk of development of a toxicity and/or instructions for the administration of one or more agents or treatments for treating, preventing, delaying, reducing or attenuating the development or risk of development of a toxicity in the subject.

11. The article of manufacture of any of embodiments 1-9, wherein the instructions further specify, if the percentage or number of cells in the sample positive for the marker, and/or percentage or number of cells of the population in the sample, is at or above a threshold level:

administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of the cell therapy to the subject; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

12. The article of manufacture of any of embodiments 1-11, wherein the instructions further specify, if the number or percentage of cells in the sample positive for the marker, and/or percentage or number of cells of the population in the sample, is below a threshold level, administering to the subject the cell therapy, optionally at a non-reduced dose, optionally on an outpatient basis or without admission to the hospital for one or more days.

13. The article of manufacture of any of embodiments 1-12, wherein the instructions further specify administering the cell therapy to the subject and wherein the instructions further specify, if the number or percentage of cells in the sample positive for the marker, and/or percentage or number of cells of the population in the sample, is below a threshold level:

the administration of the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

14. The article of manufacture of any of embodiments 11-13, wherein the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

15. The article of manufacture of any of embodiments 11-14, wherein the threshold level is a percent of cells surface positive for the marker in the biological sample or blood or apheresis sample that is or is about 20%, 25%, 30%, 35%, 40%, 45%, 50%, 55% or 60%.

16. An article of manufacture comprising a cell therapy, said cell therapy optionally comprising a dose or composition of genetically engineered cells expressing a recombinant receptor, and instructions for administering the T cell therapy, wherein:

(A) the instructions or literature further provide that the administration is carried out following or based on the results of an assessment, in a biological sample, of the presence or percentage or number of cells of a myeloid cell population or of a level of expression of a marker expressed by cells of said population or of a myeloid marker, optionally said biological sample obtained from the subject prior to administering the cell therapy and/or said biological sample not comprising the recombinant receptor and/or said engineered cells; and/or (B) the instructions or literature further specify one or more specific aspects of the treatment or carrying out one or more interventions to be carried out in association with the administration, optionally based on a parameter assessed in a biological sample from the subject and/or an assessed level of risk of developing a toxicity or toxic outcome following administration of the cell therapy, wherein (i) the parameter is or comprises the presence or percentage or number of cells of a myeloid cell population or of a level of expression of a marker expressed by cells of said population or of a myeloid marker or (ii) the assessed level of risk is based on the presence or percentage or number of cells of a myeloid cell population or of a level of expression of a marker expressed by cells of said population or of a myeloid marker, in a cell, sample, or tissue of the subject.

17. The article of manufacture of embodiment 16, 155, or 156, wherein said assessment in (A) comprises detection which optionally comprises contacting a reagent capable of directly or indirectly detecting myeloid cells or the marker expressed on a population of myeloid cells with the biological sample and determining the percentage or number of cells positive for, optionally surface positive for, the marker and/or level in the biological sample.

18. The article of manufacture of embodiment 16, wherein the population of cells is or comprises monocytes.

19. The article of manufacture of any of embodiments 16-18, wherein the marker is a myeloid cell marker and/or wherein the marker is CD14 and/or wherein the population of cells is or comprises CD14+ myeloid cells, optionally wherein the marker is expressed on the surface of human cells, optionally wherein the marker is human CD14.

20. The article of manufacture of any of embodiments 16-19, wherein the marker is a myeloid marker that is a monocyte marker, optionally wherein:

the monocyte marker is not present on or is not ordinarily expressed on populations of cells other than myeloid cells or other than monocytes; and/or is a marker that is co-expressed or substantially co-expressed with, or that has a coextensive or essentially coextensive expression pattern, as CD14 in human cells and/or has a similar or essentially the same expression pattern as CD14 in humans.

21. The article of manufacture of any of embodiments 17-20, wherein the reagent is a binding molecule that specifically binds to the marker or cells of the myeloid cell population.

22. The article of manufacture of any of embodiments 17-21, wherein the reagent is an antibody or an antigen-binding fragment thereof.

23. The article of manufacture of any of embodiments 16-22, wherein the biological sample is or is obtained from a blood, plasma or serum sample.

24. The article of manufacture of any of embodiments 16-23, wherein the biological sample is or is obtained from an apheresis or leukapheresis sample.

25. The article of manufacture of any of embodiments 17-24, further comprising the reagent for detecting myeloid cells or a marker expressed on a population of myeloid cells and/or further comprising instructions for use with, prior to and/or in connection with the reagent for detecting myeloid cells or a marker expressed on a population of myeloid cells.

26. The article of manufacture of any of embodiments 16-25, further comprising one or more agents or treatments for treating, preventing, delaying, reducing or attenuating the development or a risk of development of a toxicity and/or instructions for the administration of one or more agents or treatments for treating, preventing, delaying, reducing or attenuating the development or risk of development of a toxicity in the subject.

27. The article of manufacture of any of embodiments 16-26, wherein the instructions for administering the cell therapy specify, if the percentage or number of cells in the sample positive for the marker and/or percentage or number of cells of the population in the sample, is at or above a threshold level:

administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of administration of the therapeutic cell composition or the genetically engineered cells; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

28. The article of manufacture of any of embodiments 16-27, wherein the instructions for administering the cell therapy specify, if the number or percentage of cells in the sample positive for the marker, and/or percentage or number of cells of the population in the sample, is below a threshold level, administering to the subject the cell therapy, optionally at a non-reduced dose, optionally on an outpatient basis or without admission to the hospital for one or more days.

29. The article of manufacture of any of embodiments 16-28, wherein the instructions further specify administering the cell therapy to the subject and wherein the instructions further specify, if the number or percentage of cells in the sample positive for the marker, and/or percentage or number of cells of the population in the sample, is below a threshold level:

not administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

30. The article of manufacture of any of embodiments 27-29, wherein the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

31. The article of manufacture of any of embodiments 27-30, wherein the threshold level is a percent of cells surface positive for the marker in the biological sample or blood or apheresis sample that is or is about 20%, 25%, 30%, 35%, 40%, 45%, 50%, 55% or 60%.

32. An article of manufacture comprising an agent capable of treating, preventing, delaying, reducing or attenuating the development or risk of development of a toxicity, and instructions for administering the agent following or based on the results of an assessment in a biological sample of the presence or percentage or number of cells of a myeloid cell population or of a level of expression of a marker expressed by cells of said population or of a myeloid marker.

33. The article of manufacture of embodiment 32, wherein said assessment comprises detection which optionally comprises contacting a reagent capable of directly or indirectly detecting myeloid cells or a marker expressed on a population of myeloid cells with the biological sample and determining the percentage or number of cells positive for, optionally surface positive for, the myeloid marker and/or level in the biological sample.

34. The article of manufacture of embodiment 32 or embodiment 33, wherein the instructions specify that the agent is to be administered i) prior to, (ii) within one, two, or three days of, (iii) concurrently with and/or (iv) at first fever following, the initiation of administration of the cell therapy to the subject and/or further comprises instructions for use with, prior to and/or in connection with treatment with the cell therapy.

35. The article of manufacture of any of embodiments 32-34, wherein said biological sample is obtained from the subject prior to administering the agent or cell therapy.

36. The article of manufacture of any of embodiments 32-35, wherein the population of cells is or comprise monocytes.

37. The article of manufacture of any of embodiments 32-34, wherein the marker is a myeloid cell marker and/or wherein the marker is CD14 and/or wherein the population of cells is or comprises CD14+ myeloid cells, optionally wherein the marker is expressed on the surface of human cells, optionally wherein the marker is human CD14.

38. The article of manufacture of any of embodiments 32-37, wherein the marker is a myeloid marker that is a monocyte marker, optionally wherein:

the monocyte marker is not present on or is not ordinarily expressed on populations of cells other than myeloid cells or other than monocytes; and/or is a marker that is co-expressed or substantially co-expressed with, or that has a coextensive or essentially coextensive expression pattern, as CD14 in human cells and/or has a similar or essentially the same expression pattern as CD14 in humans.

39. The article of manufacture of any of embodiments 33-38, wherein the reagent is a binding molecule that specifically binds to the marker or cells of the myeloid cell population.

40. The article of manufacture of any of embodiments 33-39, wherein the reagent is an antibody or an antigen-binding fragment thereof.

41. The article of manufacture of any of embodiments 32-40, wherein the biological sample is or is obtained from a blood, plasma or serum sample.

42. The article of manufacture of any of embodiments 32-41, wherein the biological sample is or is obtained from an apheresis or leukapheresis sample.

43. The article of manufacture of any of embodiments 33-42, further comprising the reagent for detecting myeloid cells or a marker expressed on a population of myeloid cells and/or further comprising instructions for use with, prior to and/or in connection with the reagent for detecting myeloid cells or a marker expressed on a population of myeloid cells.

44. The article of manufacture of any of embodiments 34-43, further comprising the cell therapy and/or further comprising instructions for use with, prior to and/or in connection with treatment with the cell therapy.

45. The article of manufacture of any of embodiments 32-44, wherein the instructions for administering the agent specify, if the percentage or number of cells in the sample positive for the marker and/or percentage or number of cells of the population in the sample, is at or above a threshold level administering to the subject the agent.

46. The article of manufacture of embodiment 45, wherein the instruction further specify administering a cell therapy to the subject, wherein administration of the agent is to be carried out (i) prior to, (ii) within one, two, or three days of, (iii) concurrently with and/or (iv) at first fever following, the initiation of administration of the cell therapy to the subject.

47. The method of any of embodiments 32-44, wherein the instructions for administering the agent specify, if the percentage of cells positive in the sample for the marker is below the threshold level administering to the subject the cell therapy, optionally wherein the instructions specify the cell therapy is to be or may be administered to the subject on an outpatient setting and/or without admission of the subject to the hospital overnight or for one or more consecutive days and/or is without admission of the subject to the hospital for one or more days.

48. The article of manufacture of any of embodiments 32-47, wherein the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

49. The article of manufacture of any of embodiments 32-48, wherein the threshold level is a percent of cells surface positive for the myeloid marker in the biological sample or blood or apheresis that is or is about 20%, 25%, 30%, 35%, 40%, 45%, 50%, 55% or 60%.

50. The article of manufacture of any of embodiments 1-49, wherein assaying or assessing cells myeloid cells or a marker expressed on a population of myeloid cells comprises flow cytometry.

51. The article of manufacture of any of embodiments 10-50, wherein the toxicity comprises neurotoxicity or cytokine release syndrome (CRS), optionally grade 1 or higher neurotoxicity or CRS.

52. The article of manufacture of any of embodiments 10-51, wherein the toxicity comprises neurotoxicity.

53. The article of manufacture of any of embodiments 10-51, wherein:
the toxicity comprises severe neurotoxicity and/or comprises a grade 2 or higher neurotoxicity, a grade 3 or higher neurotoxicity, at least prolonged grade 3 neurotoxicity or is at or above grade 4 or grade 5 neurotoxicity; and/or
the toxicity comprises severe CRS and/or comprises grade 2 or higher or grade 3 or higher CRS.

54. The article of manufacture of any of embodiments 10-53, wherein the toxicity comprises severe neurotoxicity and/or a grade 3 or higher neurotoxicity.

55. The article of manufacture of any of embodiments 10-54, wherein the toxicity is associated with cerebral edema.

56. The article of manufacture of any of embodiments 10-15 and 26-55, wherein the agent or other treatment is or comprises one or more of a steroid, an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function.

57. The article of manufacture of embodiment 56, wherein the antagonist or inhibitor is or comprises an agent selected from among an antibody or antigen-binding fragment, a small molecule, a protein or peptide and a nucleic acid.

58. The article of manufacture of any of embodiments 10-15 and 27-56 wherein the agent or other treatment is an anti-IL-6 antibody or an anti-IL6 receptor antibody.

59. The article of manufacture of any of embodiments 10-15 and 27-58, wherein the agent or other treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101.

60. The article of manufacture of any of embodiments 10-15 and 27-59, wherein the agent or other treatment is or comprises tocilizumab.

61. The article of manufacture of any of embodiments 10-15 and 27-59, wherein the agent or other treatment is or comprises siltuximab.

62. The article of manufacture of embodiment 56, wherein the steroid is or comprises dexamethasone.

63. The article of manufacture of embodiment 56, wherein the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155) or upregulates microRNA-124 (miR-124).

64. The article of manufacture of embodiment 63, wherein the agent capable of preventing, blocking or reducing microglial cell activation or function is a small molecule, peptide, protein, antibody or antigen-binding fragment thereof, an antibody mimetic, an aptamer, or a nucleic acid molecule.

65. The article of manufacture of embodiment 63 or embodiment 64, wherein the agent is selected from minocycline, naloxone, nimodipine, Riluzole, MOR103, lenalidomide, a cannabinoid (optionally WIN55 or 212-2), intravenous immunoglobulin (IVIg), ibudilast, anti-miR-155 locked nucleic acid (LNA), MCS110, PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945, emactuzumab, IMC-CS4, FPA008, LY-3022855, AMG-820 and TG-3003.

66. The article of manufacture of any of embodiments 63-65, wherein the agent is an inhibitor of colony stimulating factor 1 receptor (CSF1R).

67. The article of manufacture of any of embodiments 63-66, wherein the inhibitor is selected from:
PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof;
emactuzumab, IMC-CS4, FPA008, LY-3022855, AMG-820 and TG-3003 or is an antigen-binding fragment thereof;
or a combination of any of the foregoing.

68. The article of manufacture of any of embodiments 63-67, wherein the inhibitor is PLX-3397.

69. The article of manufacture of any of embodiments 1-68, wherein the recombinant receptor specifically binds to an antigen associated with the disease or condition or expressed in cells of the environment of a lesion associated with the disease or condition.

70. The article of manufacture of any of embodiments 1-69, wherein the disease or condition is a cancer.

71. The article of manufacture of any of embodiments 1-70, wherein the disease or condition is a myeloma, leukemia or lymphoma.

72. The article of manufacture of any of embodiments 1-71, wherein the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

73. The article of manufacture of any of embodiments 69-72, wherein the antigen is Receptor Tyrosine Kinase Like Orphan Receptor 1 (ROR1), B cell maturation antigen (BCMA), carbonic anhydrase 9 (CA9, also known as G250 or CAIX), Her2/neu (receptor tyrosine kinase erb-B2), CD19, CD20, CD22, and hepatitis B surface antigen, antifolate receptor, CD23, CD24, CD30, CD33, CD38, CD44, chondroitin sulfate proteoglycan 4 (CSPG4), epidermal growth factor protein (EGFR), epithelial glycoprotein 2 (EPG-2), epithelial glycoprotein 40 (EPG-40), ephrinB2, ephrin receptor A2 (EPHa2), Her3 (erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, glypican-3 (GPC3), G Protein Coupled Receptor 5D (GPCR5D), Human high molecular weight-melanoma-associated antigen (HMW-MAA), IL-22 receptor alpha(IL-22Rα or IL-22R-alpha), IL-13 receptor alpha 2 (IL-13Rα2 or IL-13R-alpha2), kinase insert domain receptor (kdr), kappa light chain, Leucine Rich Repeat Containing 8 Family Member A (LRRC8A), Lewis Y, L1-cell adhesion molecule, (L1-CAM), Melanoma-associated antigen (MAGE)-A1, MAGE-A3, MAGE-A6, MAGE-A10, Preferentially expressed antigen of melanoma (PRAME), survivin, TAG72, B7-H3, B7-H6, IL-13 receptor alpha 2 (IL-13Rα2), CD171, Human leukocyte antigen A1 (HLA-AI), Human leukocyte antigen A2 (HLA-A2), folate receptor-alpha, CD44v6, CD44v7/8, αvβ6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, dual antigen, a cancer-testes antigen, mesothelin (MSLN), murine cytomegalovirus (CMV), mucin 1 (MUC1), MUC16, prostate specific antigen, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), oncofetal antigen, tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific or pathogen-expressed antigen.

74. The article of manufacture of any of embodiments 1-73, wherein the recombinant receptor is a T cell receptor or a functional non-T cell receptor.

75. The article of manufacture of any of embodiments 1-74, wherein the recombinant receptor is a chimeric antigen receptor (CAR).

76. The article of manufacture of embodiment 75, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3ξ) chain; and/or wherein the CAR further comprises a costimulatory signaling region, which optionally comprises a signaling domain of CD28 or 4-1BB.

77. The article of manufacture of any of embodiments 1-74, wherein the engineered cells comprise T cells, optionally CD4+ and/or CD8+ T cells.

78. The article of manufacture of embodiment 77, wherein the T cells are primary T cells obtained from a subject.

79. The article of manufacture of any of embodiments 1-78, wherein the dose that is not associated with risk of developing toxicity or severe toxicity is or comprises less than or less than about $5 \times 10^7$ total recombinant receptor-expressing cells, optionally CAR+ cells, total T cells, or total peripheral blood mononuclear cells (PBMCs), such as less than or less than about $2.5 \times 10^7$, less than or less than about $1.0 \times 10^7$, less than or less than about $5.0 \times 10^6$, less than or less than about $1.0 \times 10^6$, less than or less than about $5.0 \times 10^5$, or less than or less than about $1 \times 10^5$ total recombinant receptor-expressing cells, optionally CAR+ cells, total T cells, or total peripheral blood mononuclear cells (PBMCs).

80. The article of manufacture of any of embodiments 1-79, wherein the dose that is not associated with risk of developing toxicity or severe toxicity is or comprises from or from about $1 \times 10^5$ to $5 \times 10^7$ total recombinant receptor-expressing cells, optionally CAR+ cells, total T cells, or total peripheral blood mononuclear cells (PBMCs), such as $1\times10^5$ to $2.5\times10^7$, $1\times10^5$ to $1.0\times10^7$, $1\times10^5$ to $5.0\times10^6$, $1\times10^5$ to $1.0\times10^6$, $1.0\times10^5$ to $5.0\times10^5$, $5.0\times10^5$ to $5\times10^7$, $5\times10^5$ to $2.5\times10^7$, $5\times10^5$ to $1.0\times10^7$, $5\times10^5$ to $5.0\times10^6$, $5\times10^5$ to $1.0\times10^6$, $1.0\times10^6$ to $5\times10$, $1\times10^6$ to $2.5\times10^7$, $1\times10^6$ to $1.0\times10^7$, $1\times10^6$ to $5.0\times10^6$, $5.0\times10^6$ to $5\times10^7$, $5\times10^6$ to $2.5\times10^7$, $5\times10^6$ to $1.0\times10^7$, $1.0\times10^7$ to $5\times10^7$, $1\times10^7$ to $2.5\times10^7$ or $2.5\times10^7$ to $5\times10^7$ total recombinant receptor-expressing cells, optionally CAR+ cells, total T cells, or total peripheral blood mononuclear cells (PBMCs).

81. The article of manufacture of any of embodiments 1-80, wherein the reagent is detectably labeled, optionally fluorescently labeled.

82. A method of selecting a subject for treatment, the method comprising:
(a) contacting a biological sample with a reagent capable of detecting or that is specific for a population of myeloid cells or a marker expressed on a population of myeloid cells, wherein:
the biological sample is from a subject that is a candidate for treatment with a cell therapy, said cell therapy optionally comprising a dose or composition of genetically engineered cells expressing a recombinant receptor; and
the biological sample is obtained from the subject prior to administering the cell therapy and/or said biological sample does not comprise the recombinant receptor and/or said engineered cells; and
(b) selecting a subject in which either:
i) the percentage or number of cells in the sample positive for the marker, and/or percentage or number of cells of the population in the sample, is at or above a threshold level, thereby identifying a subject that is at risk for developing a toxicity to the cell therapy; or
ii) the percentage or number of cells in the sample positive for the marker, and/or percentage or number of cells of the population in the sample, is below a threshold level.

83. The method of embodiment 82, wherein:
(a) the subject in i) is selected for treatment, and the treatment is for administering to the subject (1) an agent or other treatment capable of treating, preventing, delaying, reducing or attenuating the development or risk of development of a toxicity and (2) the cell therapy, wherein administration of the agent is to be administered (i) prior to, (ii) within one, two, or three days of, (iii) concurrently with and/or (iv) at first fever following, the initiation of administration of the cell therapy to the subject; and/or
(b) the subject in i) is selected for treatment, and the treatment is for administering to the subject a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or
(c) the subject in i) is selected for treatment, and the treatment is administering to the subject a cell therapy in an in-patient setting and/or with admission to the hospital for one or more days, optionally wherein the cell therapy is otherwise to be administered to subjects on an outpatient basis or without admission to the hospital for one or more days.

84. The method of embodiment 82 or embodiment 83, wherein a subject in i) is selected for treatment, and the method further comprises: (a) administering to the subject (1) an agent or other treatment capable of treating, preventing, delaying, reducing or attenuating the development or risk of development of a toxicity and (2) the cell therapy, wherein administration of the agent is carried out (i) prior to, (ii) within one, two, or three days of, (iii) concurrently with and/or (iv) at first fever following, the initiation of administration of the cell therapy to the subject;
(b) administering to the subject a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy;
(c) administering to the subject a cell therapy or a dose of genetically engineered cells of a cell therapy that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or
(d) administering to the subject a cell therapy in an in-patient setting and/or with admission to the hospital for one or more days, optionally wherein the cell therapy is otherwise to be administered to subjects on an outpatient basis or without admission to the hospital for one or more days.

85. The method of embodiment 82, wherein:
(a) the subject in ii) is selected for treatment, and the treatment is for administering to the subject a cell therapy, optionally at a non-reduced dose, or optionally on an outpatient basis or without admission to the hospital for one or more days;
(b) the subject in ii) is selected for treatment, and the treatment is for administering to the subject a cell therapy, wherein the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or
(c) the subject in ii) is selected for treatment, and the treatment is for administering a cell therapy on an outpatient setting and/or without admission of the subject to the hospital overnight or for one or more consecutive days and/or is without admission of the subject to the hospital for one or more days.

86. The method of embodiment 82 or embodiment 85, wherein a subject in ii) is selected, and the method further comprises administering to the subject the cell therapy, optionally at a non-reduced dose, optionally on an outpatient basis or without admission to the hospital for one or more days.

87. The method of embodiment 82, embodiment 85 or embodiment 86, wherein a subject in ii) is selected, and the method further comprises administering to the subject the cell therapy, wherein:
the administration of the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or
the administration of the cell therapy is to be or may be administered to the subject on an outpatient setting and/or without admission of the subject to the hospital overnight or for one or more consecutive days and/or is without admission of the subject to the hospital for one or more days.

88. A method of treatment, comprising:
(a) assaying a biological sample for the presence or percentage or number of cells of a myeloid cell population or of a level of expression of a marker expressed by cells of said population or of a myeloid marker, wherein the biological sample is from a subject that is a candidate for treatment, optionally with a cell therapy, said cell therapy optionally comprising a dose or composition of genetically engineered cells expressing a recombinant receptor for treating a disease or condition; and
(b) following or based on the results of the assay, administering to the subject the cell therapy, and, optionally, an agent or other treatment capable of treating, preventing, delaying, reducing or attenuating the development or risk of development of a toxicity.

89. A method of treatment, comprising, following or based on the results of an assay, of a biological sample from a subject, for the presence or percentage or number of cells of a myeloid cell population or of a level of cells positive for expression of a marker expressed by cells of said population or positive for expression of a myeloid marker, administering to the subject (i) a cell therapy, optionally comprising a dose or composition of genetically engineered cells expressing a recombinant receptor for treating a disease or condition, and, optionally, (ii) an agent or other treatment capable of treating, preventing, delaying, reducing or attenuating the development or risk of development of a toxicity, wherein the biological sample is obtained from the subject prior to administering the cell therapy.

90. The method of embodiment 88 or embodiment 89, wherein said assaying comprises detection which optionally comprises contacting a reagent capable of directly or indirectly detecting myeloid cells or a marker expressed on a population of myeloid cells with the biological sample and determining the percentage or number of cells positive for, optionally surface positive for, the myeloid marker and/or level in the biological sample.

91. The method of any of embodiments 88-90, wherein if the percentage or number of cells in the sample positive for the marker, and/or percentage or number of cells of the population in the sample, is at or above a threshold level:
administering to the subject the agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of the cell therapy to the subject; and/or
administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or
administering to the subject the cell therapy in an in-patient setting and/or with admission to the hospital for one or more days, optionally wherein the cell therapy is otherwise to be administered to subjects on an outpatient basis or without admission to the hospital for one or more days.

92. The method of any of embodiments 88-90, wherein if the percentage or number or percentage of cells in the sample positive for the marker, and/or percentage or number of cells of the population in the sample, is at or below a threshold level:
the administration of the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or
the administration of the cell therapy is to be or may be administered to the subject on an outpatient setting and/or without admission of the subject to the hospital overnight or for one or more consecutive days and/or is without admission of the subject to the hospital for one or more days.

93. A method of assessing a risk of neurotoxicity, comprising:
assaying an apheresis sample from a subject for the presence or percentage or number of cells of a myeloid cell population or of cells positive for a marker expressed by cells of said population or positive for expression of a myeloid marker; and
following or based on the results of the assay, determining if the subject is at risk of developing neurotoxicity or severe neurotoxicity following administration of a cell therapy, said cell therapy comprising a composition comprising a dose of genetically engineered cells expressing a recombinant receptor for treating a disease or condition in the subject,
wherein the subject is a candidate for treatment with the cell therapy and the apheresis sample is obtained from the subject prior to administering the cell therapy and/or said apheresis sample does not comprise the recombinant receptor and/or said engineered cells.

94. The method of embodiment 93, wherein the subject is assessed as at risk of developing neurotoxicity or severe neurotoxicity if the percentage or number of cells in the sample positive for the myeloid marker, and/or percentage or number of cells of the population of myeloid cells in the sample, is at or above a threshold level.

95. The method of embodiment 94, wherein if the subject is assessed as at risk of developing neurotoxicity or severe neurotoxicity, the method further comprising:
monitoring the subject after administration of the cell therapy for development of a sign or symptom of a neurotoxicity other than fever;
administering to the subject the agent or other treatment capable of treating, preventing, delaying, reducing or attenuating the development or risk of development of a neurotoxicity (i) prior to, (ii) within one, two, or three days of, (iii) concurrently with and/or (iv) at first fever following, the initiation of administration of the cell therapy to the subject;
administering to the subject the cell therapy at a reduced dose or at a dose that is not associated with risk of developing neurotoxicity or severe neurotoxicity, or is not associated with a risk of developing a neurotoxicity or severe neurotoxicity in a majority of subjects, and/or a majority of subjects having a disease or condition that the subject has or is suspected of having, following administration of the cell therapy; and/or
administering to the subject the cell therapy in an in-patient setting and/or with admission to the hospital for one or more days, optionally wherein the cell therapy is otherwise to be administered to subjects on an outpatient basis or without admission to the hospital for one or more days.

96. The method of embodiment 93, wherein the subject is assessed as not suspected to be at risk or as not likely to be at risk of developing neurotoxicity or severe neurotoxicity if the percentage or number of cells in the sample positive for the marker, and/or percentage or number of cells of the population of myeloid cells in the sample, is below a threshold level.

97. The method of embodiment 96, wherein if the subject is assessed as not suspected, or not likely, to be at risk of developing neurotoxicity or severe neurotoxicity:

the subject is not further administered, prior to or concurrently with administering the cell therapy and/or prior to the development of a sign or symptom of a neurotoxicity other than fever, an agent or treatment capable of treating, preventing, delaying, or attenuating the development of the neurotoxicity; or the method further comprises administering the cell therapy to the subject on an outpatient setting and/or without admission of the subject to the hospital overnight or for one or more consecutive days and/or is without admission of the subject to the hospital for one or more days.

98. A method of monitoring a subject following administration of a cell therapy, the method comprising observing a subject administered a cell therapy for the development of a sign or symptom of a neurotoxicity or severe neurotoxicity other than fever, wherein the subject is one that has been determined to be at risk of, or likely to be at risk of, developing neurotoxicity or severe neurotoxicity as determined based on assaying the presence or percentage or number of cells of a myeloid cell population or of cells positive for a marker expressed by cells of said population or positive for expression of a myeloid marker at or above a threshold level in an apheresis sample, said apheresis sample having been obtained from the subject prior to the administration of the cell therapy and/or said apheresis sample not comprising the recombinant receptor and/or said engineered cells, wherein the cell therapy comprises a composition comprising a dose of genetically engineered cells expressing a recombinant receptor for treating a disease or condition in the subject.

99. The method of embodiment 98, wherein the subject has been administered the cell therapy in an in-patient setting and/or with admission to the hospital for one or more days or is admitted to the hospital during the period or a portion of the period of the observation, optionally wherein the cell therapy is otherwise to be administered to subjects on an outpatient basis or without admission to the hospital for one or more days in the absence of the subject being determined to be at risk.

100. A method of prophylactic treatment, comprising administering, to a subject, an agent or other treatment capable of treating, preventing, delaying, reducing or attenuating the development or risk of development of a toxicity, wherein:

the subject is a candidate for treatment optionally with a cell therapy, said cell therapy optionally comprising a dose or composition of genetically engineered cells expressing a recombinant receptor for treating a disease or condition; and the subject has been identified as at risk for developing a toxicity following or based on the results of an assay, of a biological sample from the subject, for the presence or percentage or number of cells of a myeloid cell population or of a level of expression of a marker expressed by cells of said population or of a myeloid marker, said biological sample obtained from the subject prior to administering the cell therapy and/or said biological sample not comprising the recombinant receptor and/or said engineered cells.

101. The method of any of embodiments 91-97, and 100, wherein said assay comprises detection which optionally comprises contacting a reagent capable of directly or indirectly detecting myeloid cells or a marker expressed on a population of myeloid cells with the biological sample and determining the percentage or number of cells positive, optionally surface positive, for the marker and/or level in the biological sample.

102. The method of embodiments 91-97, and 100-101, wherein the agent is administered to the subject if the percentage or number of cells in the sample positive for the marker, and/or percentage or number of cells of the population in the sample, is at or above a threshold level.

103. The method of any of embodiments 91-97, and 100-102, wherein the agent is administered (i) prior to, (ii) within one, two, or three days of, (iii) concurrently with and/or (iv) at first fever following, the initiation of administration of the cell therapy to the subject.

104. The method of any of embodiments 82-103, wherein the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

105. The method of any of embodiments 82-104, wherein the threshold level is a percent of cells surface positive for the marker in the biological sample or blood or apheresis sample that is or is about 20%, 25%, 30%, 35%, 40%, 45%, 50%, 55% or 60%.

106. The method of any of embodiments 82-105, wherein the percentage is a percentage of the myeloid cell population or of cells positive for the myeloid marker among total leukocytes or total CD45+ cells, or viable cells thereof, in the sample or is a percentage of the myeloid cell population or cells positive for the myeloid marker among total leukocytes or CD45+ cells, or viable cells thereof, in the sample.

107. The method of any of embodiments 82-106, wherein the apheresis sample is a leukapheresis sample.

108. The method of any of embodiments 82-107, wherein the population of cells is or comprises monocytes.

109. The method of any of embodiments 82-108, wherein the marker is a myeloid cell marker and/or wherein the marker is CD14 and/or wherein the population of cells is or comprises CD14+ myeloid cells, optionally wherein the marker is expressed on the surface of human cells, optionally wherein the marker is human CD14.

110. The method of any of embodiments 82-109, wherein the marker is a myeloid marker that is a monocyte marker, optionally wherein:

the monocyte marker is not present on or is not ordinarily expressed on populations of cells other than myeloid cells or other than monocytes; and/or is a marker that is co-expressed or substantially co-expressed with, or that has a coextensive or essentially coextensive expression pattern, as CD14 in human cells and/or has a similar or essentially the same expression pattern as CD14 in humans.

111. The method of embodiment 82-110, wherein the marker is CD14 or the myeloid cell population is CD14+ and the percentage is a percentage of CD14+ cells among total viable leukocytes or total viable CD45+ cells in the sample.

112. The method of embodiment 111, wherein the threshold level is a percentage of CD14+ cells among total viable leukocytes or total viable CD45+ cells in the apheresis sample, wherein the percentage is or is about 45%, 46%, 47%, 48%, 49%, 50%, 51%, 52%, 53%, 54%, 55%, 56%, 57%, 58%, 59% or 60%

113. The method of any of embodiments 82-112, wherein the reagent is a binding molecule that specifically binds to the marker or cells of the myeloid cell population.

114. The method of any of embodiments 82-113, wherein the reagent is an antibody or an antigen-binding fragment thereof.

115. The method of any of embodiments 82-114, wherein the biological sample is or is obtained from a blood, plasma or serum sample.

116. The method of any of embodiments 82-115, wherein the biological sample is or is obtained from an apheresis or leukapheresis sample.

117. The method of any of embodiments 82-116, wherein assaying or assessing cells myeloid cells or a marker expressed on a population of myeloid cells comprises flow cytometry.

118. The method of any of embodiments 82-117, wherein the toxicity comprises neurotoxicity or cytokine release syndrome (CRS), optionally grade 1 or higher neurotoxicity or CRS.

119. The method of any of embodiments 82-118, wherein the toxicity is neurotoxicity. 120. The method of embodiment 119, wherein the neurotoxicity is severe neurotoxicity or is a grade 3 or higher neurotoxicity.

121. The method of any of embodiments 82-120, wherein:
the toxicity comprises severe neurotoxicity and/or comprises a grade 2 or higher neurotoxicity, a grade 3 or higher neurotoxicity, at least prolonged grade 3 neurotoxicity or is at or above grade 4 or grade 5 neurotoxicity; and/or
the toxicity comprises severe CRS and/or comprises grade 2 or higher or grade 3 or higher CRS.

122. The method of any of embodiments 82-121, wherein the toxicity is associated with cerebral edema.

123. The method of any of embodiments 82-122, wherein the agent or other treatment is or comprises one or more of a steroid, an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function.

124. The method of embodiment 123, wherein the antagonist or inhibitor is or comprises an agent selected from among an antibody or antigen-binding fragment, a small molecule, a protein or peptide and a nucleic acid.

125. The method of any of embodiments 83-124, wherein the agent or other treatment is an anti-IL-6 antibody or an anti-IL6 receptor antibody.

126. The method of any of embodiments 83-125, wherein the agent or other treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101.

127. The method of any of embodiments 83-126, wherein the agent or other treatment is or comprises tocilizumab.

128. The method of any of embodiments 83-127, wherein the agent or other treatment is or comprises siltuximab.

129. The method of embodiment 123, wherein the steroid is or comprises dexamethasone.

130. The method of embodiment 123, wherein the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155) or upregulates microRNA-124 (miR-124).

131. The method of embodiment 130, wherein the agent capable of preventing, blocking or reducing microglial cell activation or function is a small molecule, peptide, protein, antibody or antigen-binding fragment thereof, an antibody mimetic, an aptamer, or a nucleic acid molecule.

132. The method of embodiment 130 or embodiment 131, wherein the agent is selected from minocycline, naloxone, nimodipine, Riluzole, MOR103, lenalidomide, a cannabinoid (optionally WIN55 or 212-2), intravenous immunoglobulin (IVIg), ibudilast, anti-miR-155 locked nucleic acid (LNA), MCS110, PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945, emactuzumab, IMC-CS4, FPA008, LY-3022855, AMG-820 and TG-3003.

133. The method of any of embodiments 130-132, wherein the agent is an inhibitor of colony stimulating factor 1 receptor (CSF1R).

134. The method of any of embodiments 130-133, wherein the inhibitor is selected from:
PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof;
emactuzumab, IMC-CS4, FPA008, LY-3022855, AMG-820 and TG-3003 or is an antigen-binding fragment thereof;
or a combination of any of the foregoing.

135. The method of any of embodiments 130-133, wherein the inhibitor is PLX-3397.

136. The method of any of embodiments 83-135, wherein the recombinant receptor specifically binds to an antigen associated with the disease or condition or expressed in cells of the environment of a lesion associated with the disease or condition.

137. The method of any of embodiments 83-136, wherein the disease or condition is a cancer.

138. The method of any of embodiments 83-137, wherein the disease or condition is a myeloma, leukemia or lymphoma.

139. The method of any of embodiments 83-138, wherein the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

140. The method of any of embodiments 82-139, wherein the recombinant receptor specifically binds an antigen associated with, or expressed or present on cells of, the disease or condition.

141. The method of embodiment 140, wherein the antigen is Receptor Tyrosine Kinase Like Orphan Receptor 1 (ROR1), B cell maturation antigen (BCMA), carbonic anhydrase 9 (CA9, also known as G250 or CAIX), Her2/neu (receptor tyrosine kinase erb-B2), CD19, CD20, CD22, and hepatitis B surface antigen, anti-folate receptor, CD23, CD24, CD30, CD33, CD38, CD44, chondroitin sulfate proteoglycan 4 (CSPG4), epidermal growth factor protein (EGFR), epithelial glycoprotein 2 (EPG-2), epithelial glycoprotein 40 (EPG-40), ephrinB2, ephrin receptor A2 (EPHa2), Her3 (erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, glypican-3 (GPC3), G Protein Coupled Receptor 5D (GPCR5D), Human high molecular weight-melanoma-associated antigen (HMW-MAA), IL-22 receptor alpha(IL-22Rα or IL-22R-alpha), IL-13 receptor alpha 2 (IL-13Rα2 or IL-13R-alpha2), kinase insert domain receptor (kdr), kappa light chain, Leucine Rich Repeat Containing 8 Family Member A (LRRC8A), Lewis Y, L1-cell adhesion molecule, (L1-CAM), Melanoma-associated antigen (MAGE)-A1, MAGE-A3, MAGE-A6, MAGE-A10, Preferentially expressed antigen of melanoma (PRAME), survivin, TAG72, B7-H3, B7-H6, IL-13 receptor alpha 2 (IL-13Rα2), CD171, Human leukocyte antigen A1 (HLA-AI), Human leukocyte antigen A2 (HLA-A2), folate receptor-alpha, CD44v6, CD44v7/8, αvβ6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, dual antigen, a cancer-testes antigen, mesothelin (MSLN), murine cytomegalovirus (CMV), mucin 1 (MUC1), MUC16, prostate specific antigen, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), oncofetal antigen, tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific or pathogen-expressed antigen.

142. The method of any of embodiments 1-141, wherein the recombinant receptor specifically binds to a tag comprised by a therapeutic agent that specifically targets the disease or condition or cells of the disease or condition, said tag having been or is to be administered to the subject.

143. The method of any of embodiments 82-142, wherein the recombinant receptor is a T cell receptor or a functional non-T cell receptor.

144. The method of any of embodiments 82-143, wherein the recombinant receptor is a chimeric antigen receptor (CAR).

145. The method of embodiment 144, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3ξ) chain; and/or wherein the CAR further comprises a costimulatory signaling region, which optionally comprises a signaling domain of CD28 or 4-1BB.

146. The method of any of embodiments 82-145, wherein the engineered cells comprise T cells, optionally CD4+ and/or CD8+ T cells.

147. The method of embodiment 146, wherein the T cells are primary T cells obtained from a subject.

148. The method of any of embodiments 82-147, wherein the cell therapy comprises the administration of from or from about $1\times10^5$ to $1\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive.

149. The method of any of embodiments 82-148, wherein the cell therapy comprises the administration of no more than $1\times10^8$ total recombinant receptor-expressing cells, total T cells, or total peripheral blood mononuclear cells (PBMCs), no more than $1\times10^7$ total recombinant receptor-expressing cells, total T cells, or total peripheral blood mononuclear cells (PBMCs), no more than $0.5\times10^7$ total recombinant receptor-expressing cells, total T cells, or total peripheral blood mononuclear cells (PBMCs), no more than $1\times10^6$ total recombinant receptor-expressing cells, total T cells, or total peripheral blood mononuclear cells (PBMCs), no more than $0.5\times10^6$ total recombinant receptor-expressing cells, total T cells, or total peripheral blood mononuclear cells (PBMCs).

150. The method of any of embodiments 82-149, wherein the dose that is not associated with risk of developing toxicity or severe toxicity is or comprises less than or less than about $5\times10^7$ total recombinant receptor-expressing cells, optionally CAR+ cells, total T cells, or total peripheral blood mononuclear cells (PBMCs), such as less than or less than about $2.5\times10^7$, less than or less than about $1.0\times10^7$, less than or less than about $5.0\times10^6$, less than or less than about $1.0\times10^6$, less than or less than about $5.0\times10^5$, or less than or less than about $1\times10^5$ total recombinant receptor-expressing cells, optionally CAR+ cells, total T cells, or total peripheral blood mononuclear cells (PBMCs).

151. The method of any of embodiments 82-150, wherein the dose that is not associated with risk of developing toxicity or severe toxicity is or comprises from or from about $1\times10^5$ to $5\times10^7$ total recombinant receptor-expressing cells, optionally CAR+ cells, total T cells, or total peripheral blood mononuclear cells (PBMCs), such as $1\times10^5$ to $2.5\times10^7$, $1\times10^5$ to $1.0\times10^7$, $1\times10^5$ to $5.0\times10^6$, $1\times10^5$ to $1.0\times10^6$, $1.0\times10^5$ to $5.0\times10^5$, $5.0\times10^5$ to $5\times10^7$, $5\times10^5$ to $2.5\times10^7$, $5\times10^5$ to $1.0\times10^7$, $5\times10^5$ to $5.0\times10^6$, $5\times10^5$ to $1.0\times10^6$, $1.0\times10^6$ to $5\times10^7$, $1\times10^6$ to $2.5\times10^7$, $1\times10^6$ to $1.0\times10^7$, $1\times10^6$ to $5.0\times10^6$, $5.0\times10^6$ to $5\times10^7$, $5\times10^6$ to $2.5\times10^7$, $5\times10^6$ to $1.0\times10^7$, $1.0\times10^7$ to $5\times10^7$, $1\times10^7$ to $2.5\times10^7$ or $2.5\times10^7$ to $5\times10^7$ total recombinant receptor-expressing cells, optionally CAR+ cells, total T cells, or total peripheral blood mononuclear cells (PBMCs).

152. The method of any of any of embodiments 82-151, wherein the engineered cells are autologous to the subject.

153. The method of any of embodiments 82-152, wherein the engineered cells are allogeneic to the subject.

154. The method of any of embodiments 82-153, wherein the reagent is detectably labeled, optionally fluorescently labeled.

155. The article of manufacture of embodiment 16, wherein the further specifying in (B) comprises specifying administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of administration of the therapeutic cell composition or the genetically engineered cells; and/or specifying administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or specifying administering to the subject the cell therapy in an in-patient setting and/or with admission to the hospital for one or more days, optionally wherein the cell therapy is otherwise to be administered to subjects on an outpatient basis or without admission to the hospital for one or more days.

156. The article of manufacture of embodiment 16 or embodiment 155, wherein the instructions further specify the level of the parameter or assessed risk.

157. The article of manufacture of any of embodiments 1-81 and 155-156, wherein the instructions specify carrying out the methods of any of embodiments 82-154.

VIII. EXAMPLES

The following examples are included for illustrative purposes only and are not intended to limit the scope of the invention.

Example 1: Assessment of CD14+ Monocytes in Apheresis Samples as Predictive of Neurotoxicity in Connection with Autologous CAR+ T Cell Therapy Apheresis samples from subjects, obtained prior to generation of an autologous CAR+ T cell composition from isolated cells from the apheresis, were assessed for the percentage of CD14+ monocytes. The percentage of CD14+ monocytes was correlated, post facto, to the development of neurotoxicity in individual subjects following administration of the autologous therapeutic CAR+ T cell composition.

A human leukapheresis sample enriched in mononuclear cells was obtained from a whole blood sample from a subject using a leukapheresis collection system. A sample of the leukapheresis was assessed for the presence of CD14+ monocytes by flow cytometry using an anti-CD14 antibody.

CD4+ and CD8+ T cells were isolated by immunoaffinity-based enrichment from leukapheresis samples from individual subjects, activated and transduced with a viral vector encoding an anti-CD19 CAR, followed by expansion and cryopreservation. The CAR contained an anti-CD19 scFv derived from a murine antibody, an immunoglobulin spacer, a transmembrane domain derived from CD28, a costimulatory region derived from 4-1BB, and a CD3-zeta intracellular signaling domain.

Fifty eight subjects with relapsed or refractory non-Hodgkin's lymphoma with an Easter Cooperative Oncology Group (ECOG) score of 0-2, including subjects with diffuse large B cell lymphoma (DLBCL), NOS (de novo and transformed from indolent), primary mediastinal large B cell lymphoma (PMBCL) and follicular lymphoma Grade 3B (FL3B), were administered the generated autologous T cells expressing an anti-CD19 chimeric antigen receptor (CAR). The cryopreserved cell compositions were thawed at bedside prior to intravenous administration. The therapeutic T cell composition was administered as a defined composition cell product with formulated CD4+ and CD8+ populations of CAR+ engineered T cells derived from the same subject administered at a target ratio of approximately 1:1. Subjects were treated with either dose level 1 (DL-1) containing $5 \times 10^7$ total CAR-expressing T cells or dose level 2 (DL-2) containing $1 \times 10^8$ (DL-2) total CAR-expressing T cells.

Prior to administration of the CAR-expressing T cells, subjects were treated with 30 mg/m² fludarabine daily for 3 days and 300 mg/m² cyclophosphamide daily for 3 days.

After treatment, subjects were assessed and monitored for neurotoxicity (neurological complications including symptoms of confusion, aphasia, encephalopathy, myoclonus seizures, convulsions, lethargy, and/or altered mental status), graded on a 1-5 scale, according to the National Cancer Institute—Common Toxicity Criteria (CTCAE) scale, version 4.03 (NCI-CTCAE v4.03). Common Toxicity Criteria (CTCAE) scale, version 4.03 (NCI-CTCAE v4.03). See Common Terminology for Adverse Events (CTCAE) Version 4, U.S. Department of Health and Human Services, Published: May 28, 2009 (v4.03: Jun. 14, 2010); and Guido Cavaletti & Paola Marmiroli *Nature Reviews Neurology* 6, 657-666 (December 2010). Of the assessed subjects, 83% (48/58) of the treated subjects did not exhibit any neurotoxicity, while 17% (10/58) of subjects developed a grade 1-4 of neurotoxicity (any NTX Gr), with Grade 3 or higher (NTX Gr3+) neurotoxicity observed in 12% (7/58) of subjects.

Figure 1A:
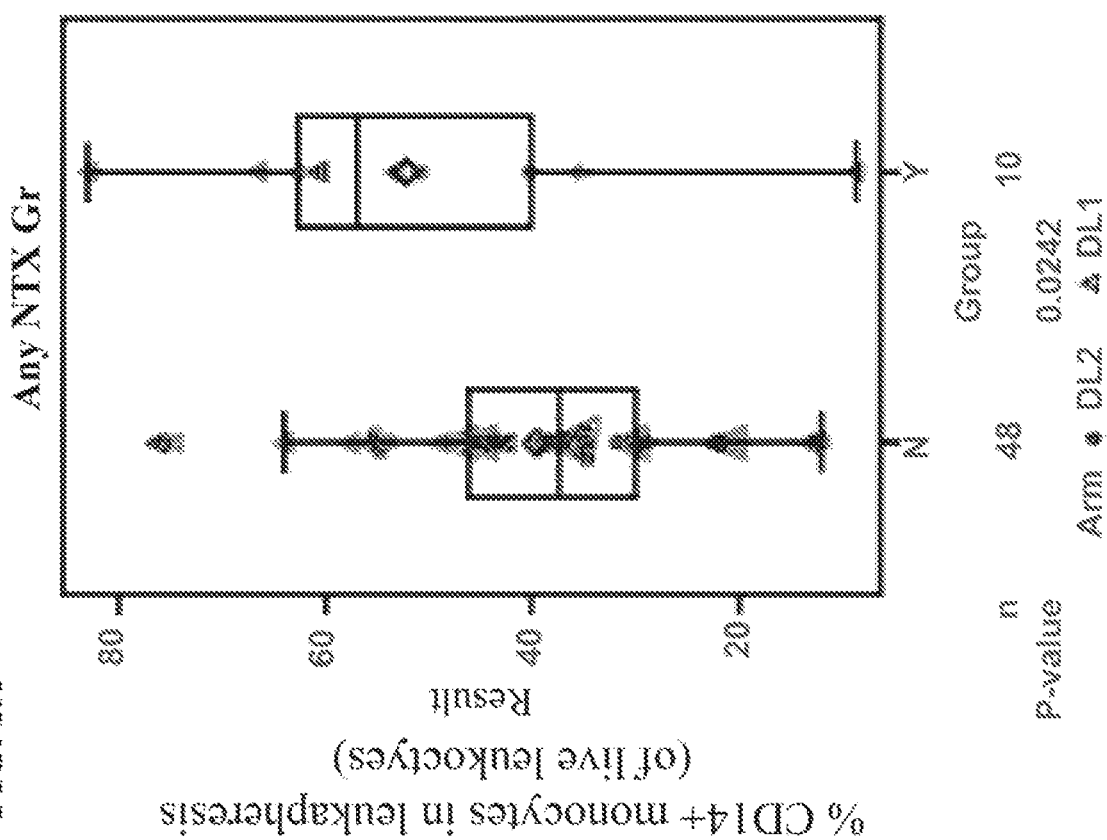
FIG. 1A shows a graph displaying the percentages of CD14+ monocytes in leukapheresis samples in subjects. Data is shown for subjects who did not develop neurotoxicity (left) versus subjects who developed neurotoxicity (right).

The degree of correlation of percent CD14+ monocytes in apheresis samples to neurotoxicity in individual subjects following infusion of autologous CAR+ T cells was assessed by univariate analysis. As shown in FIGS. 1A and 1B, subjects that did not develop any neurotoxicity had a significantly lower percentage of CD14+ monocytes of live leukocytes in leukapheresis samples than subjects that developed neurotoxicity (p=0.0242) or grade 3+ higher neurotoxicity (p=0.0149). Similar results were observed with other statistical methods.

The results are consistent with a finding that the presence of myeloid cells (e.g. monocytes), such as determined by the myeloid-specific marker CD14, is an intrinsic factor of leukapheresis samples in individual subjects for predicting risk of developing neurotoxicity in connection with subsequent administration of autologous CAR-expressing T cells. These results support the use of CD14 as a marker in apheresis or other blood-derived samples, from subjects that are candidates for CAR+ T cell therapy, to identify or screen subjects for prophylactic treatment with interventions to ameliorate the risk of neurotoxicity to the CAR+ T cell therapy.

Example 2: Administration of Anti-CD19 CAR-Expressing Cells to Subjects with Relapsed and Refractory Non-Hodgkin's Lymphoma (NHL)

A. Subjects and Treatment

Therapeutic CAR+ T cell compositions containing autologous T cells expressing a chimeric antigen-receptor (CAR) specific for CD19 were administered to subjects with B cell malignancies. Results are described in this example for evaluation through a particular time-point in an ongoing study for cohort (full cohort) of fifty-five (55) adult human subjects with relapsed or refractory (R/R) aggressive non-Hodgkin's lymphoma (NHL), including diffuse large B-cell lymphoma (DLBCL), de novo or transformed from indolent lymphoma (NOS), primary mediastinal large b-cell lymphoma (PMBCL), and follicular lymphoma grade 3b (FLG3B) after failure of 2 lines of therapy. Among the subjects treated were those having Eastern Cooperative Oncology Group (ECOG) scores of between 0 and 2 (median follow-up 3.2 months). The 55 subjects did not include subjects with mantle cell lymphoma (MCL). No subjects were excluded based on prior allogenic stem cell transplantation (SCT) and there was no minimum absolute lymphocyte count (ALC) for apheresis required.

Outcomes at this time-point for a core subset of the 55 subjects (the subset excluding those subjects with a poor performance status (ECOG 2), DLBCL transformed from marginal zone lymphomas (MZL) and/or chronic lymphocytic leukemia (CLL, Richter's) (core cohort)) were separately assessed.

The demographics and baseline characteristics of the full and core cohort are set forth in Table 6.

TABLE 6

Demographics and Baseline Characteristics

| Characteristic | FULL N = 55 | CORE N = 44 |
|---|---|---|
| Median Age, years (range) | 61 (29-82) | 61 (29-82) |
| ≥65 years, n (%) | 22 (40) | 17 (39) |
| Male/Female, n (%) | 38/17 (69/31) | 28/16 (64/36) |
| Months from diagnosis, median (range) | 17 (3-259) | 20 (8-259) |
| B-NHL Subtype, n (%) | | |
| DLBCL, NOS | 40 (73) | 35 (80) |
| Transformed DLBCL | 14 (26) | 8 (18) |
| Follicular, Grade 3B | 1 (2) | 1 (2) |
| Molecular Subtype, n (%) | | |
| Double/triple hit | 15 (27) | 12 (27) |
| Double expressor | 6 (1) | 4 (9) |
| Patient Characteristics, n (%) | | |
| Chemorefractory† | 42 (76) | 34 (77) |
| ECOG 0-1 | 48 (87) | 44 (100) |
| ECOG 2 | 7 (13) | 0 |
| Prior lines of therapy, median (range) | 3 (1-11) | 3 (1-8) |
| <5 lines of therapy | 44 (80) | 37 (84) |
| Any HSCT | 27 (49) | 22 (50) |
| Allogeneic | 4 (7) | 3 (7) |
| Autologous | 24 (44) | 20 (45) |

*SD or PD to last chemo-containing regimen or relapse <12 months after autologous SCT The therapeutic T cell compositions administered had been generated by a process including immunoaffinity-based enrichment of CD4+ and CD8+ cells from leukapheresis samples from the individual subjects to be treated. Isolated CD4+ and CD8+ T cells were activated and transduced with a viral vector encoding an anti-CD19 CAR, followed by expansion and cryopreservation of the engineered cell populations. The CAR contained an anti-CD19 scFv derived from a murine antibody, an immunoglobulin-derived spacer, a transmembrane domain derived from CD28, a costimulatory region derived from 4-1BB, and a CD3-zeta intracellular signaling domain.

The cryopreserved cell compositions were thawed prior to intravenous administration. The therapeutic T cell dose was administered as a defined cell composition by administering a formulated CD4+ CAR+ cell population and a formulated CD8+ CAR+ population administered at a target ratio of approximately 1:1. Subjects were administered a single or double dose of CAR-expressing T cells (each single dose via separate infusions of CD4+ CAR-expressing T cells and CD8+ CAR-expressing T cells, respectively) as follows: a single dose of dose level 1 (DL1) containing $5\times10^7$ total CAR-expressing T cells (n=30), a double dose of DL1 in which each dose was administered approximately fourteen (14) days part (n=6, including one subject that inadvertently received two DL2 doses via the two-dose schedule, due to a dosing error), or a single dose of dose level 2 (DL2) containing $1\times10^8$ (DL2) total CAR-expressing T cells (n=18). Beginning at three (3) days prior to CAR+ T cell infusion, subjects received a lymphodepleting chemotherapy with flurabine (flu, 30 mg/m$^2$) and cyclophosphamide (Cy, 300 mg/m$^2$).

B. Safety

The presence or absence of treatment-emergent adverse events (TEAE) of the CAR-T cell therapy was assessed.

Figure 2:
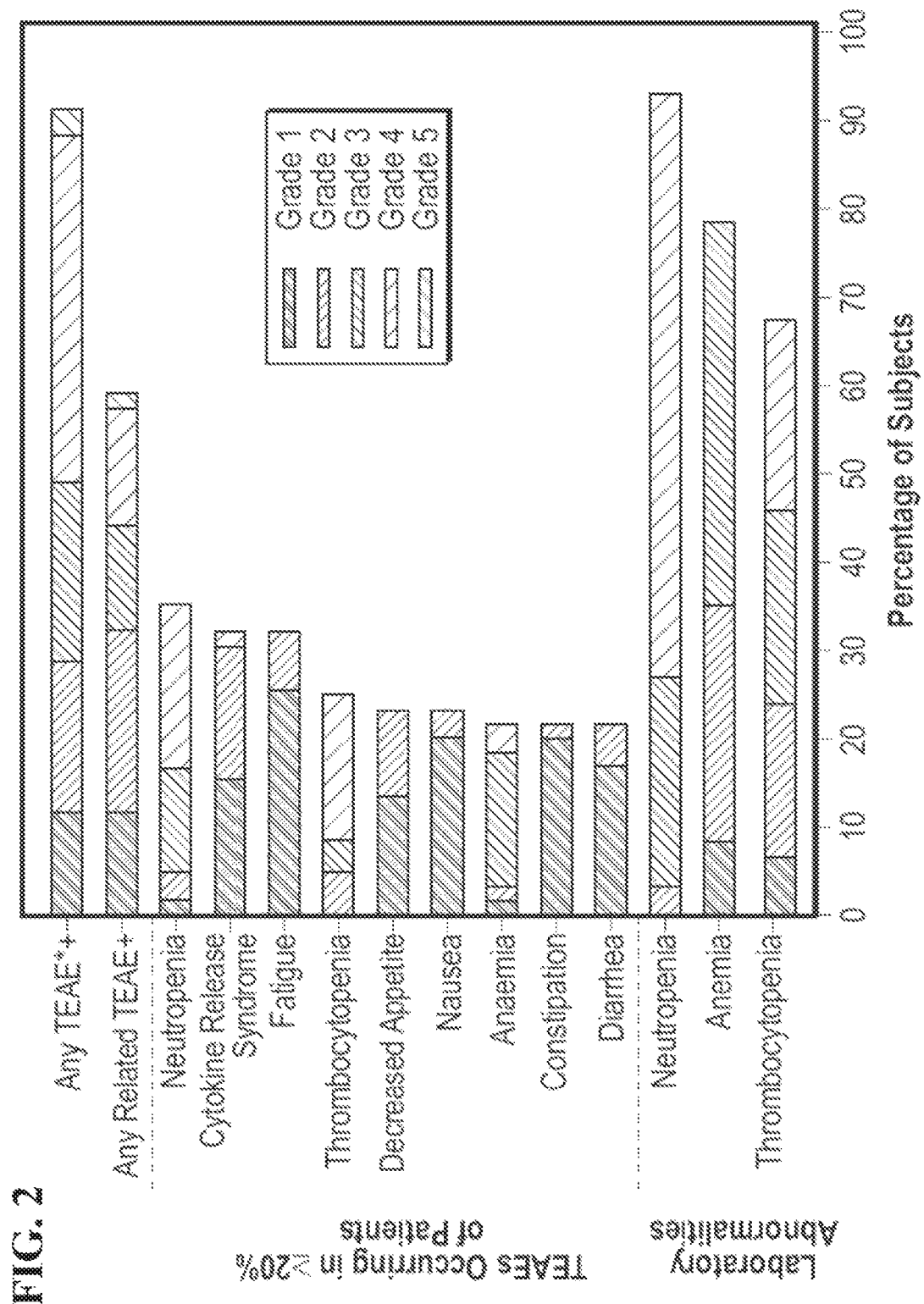
FIG. 2 shows the percentage of subjects who experienced laboratory abnormalities and TEAEs that occurred in ≥20% of subjects. *: One Grade 5 AE of multi-organ failure unrelated to study treatment and due to progression of lymphoma; †: One Grade 5 AE of diffuse alveolar damage, investigator assessed as related to fludarabine, cyclophosphamide, and CAR T cell therapy, occurred on day 23 in a subject who refused mechanical ventilation for progressive respiratory failure while neutropenic on growth factors and broad spectrum antibiotics and antifungals

FIG. 2 depicts the percentage of subjects who were observed to have experienced laboratory abnormalities and TEAEs, which occurred in ≥20% of subjects. In addition to the TEAEs shown in FIG. 2, the following event terms were observed at Grade 3-4 in ≥5% of patients: white blood cell count decreased (13.6%), encephalopathy (12%), hypertension (7%). Degree of toxicities observed were consistent between dose levels 1 and 2.

Subjects also were assessed and monitored for neurotoxicity (neurological complications including symptoms of confusion, aphasia, encephalophathy, myoclonus seizures, convulsions, lethargy, and/or altered mental status), graded on a 1-5 scale, according to the National Cancer Institute—Common Toxicity Criteria (CTCAE) scale, version 4.03 (NCI-CTCAE v4.03). Common Toxicity Criteria (CTCAE) scale, version 4.03 (NCI-CTCAE v4.03). See Common Terminology for Adverse Events (CTCAE) Version 4, U.S. Department of Health and Human Services, Published: May 28, 2009 (v4.03: Jun. 14, 2010); and Guido Cavaletti & Paola Marmiroli *Nature Reviews Neurology* 6, 657-666 (December 2010). Cytokine release syndrome (CRS) also was determined and monitored, graded based on severity.

In 84% of the full cohort subjects, severe (grade 3 or higher) cytokine release syndrome (CRS) and severe neurotoxicity were not observed. Additionally, it was observed that 60% of the full cohort subjects did not develop any grade of CRS or neurotoxicity. No differences in incidence of CRS, neurotoxicity (NT), sCRS, or severe neurotoxicity (sNT) were observed between dose levels. Table 7 summarizes the incidence of cytokine release syndrome (CRS) and neurotoxicity adverse events in patients 28 days after receiving at least one dose of CAR-T cells. As shown in Table 7, no sCRS (Grade 3-4) was observed in any subjects that received a single dose of DL2 or double dose of DL1. Severe neurotoxicity or severe CRS (grade 3-4) was observed in 16% (9/55) of the full cohort of subjects and in 18% (8/44) of the subjects in the core subset. 11% (n=6) of subjects received tocilizumab, 24% (n=13) of subjects received dexamethasone. Among the ECOG2 subjects within the full cohort, observed rates of CRS and neurotoxicity were 71% and 29%, respectively.

TABLE 7

Assessment of Presence or Absence of CRS and Neurotoxicity Adverse Events

| | FULL | | | | |
|---|---|---|---|---|---|
| | All Dose Levels | DL1S | DL2S | DL1D† | CORE |
| Safety, N | 55 | 30 | 19 | 6 | 44 |
| sCRS or sNT, n (%) | 9 (16) | 6 (20) | 2 (11) | 1 (17) | 8 (18) |
| CRS or NT, n (%) | 22 (40) | 12 (40) | 7 (37) | 3 (50) | 15 (34) |
| CRS | | | | | |
| Grade 1-2, n (%) | 18 (33) | 10 (33) | 5 (26) | 3 (50) | 12 (27) |
| Grade 3-4, n (%) | 1 (2) | 1 (3) | 0 | 0 | 1 (2) |
| Neurotoxicity | | | | | |
| Grade 1-2, n (%) | 3 (6) | 1 (3) | 2 (11) | 0 | 2 (5) |
| Grade 3-4, n (%) | 9 (16) | 6 (20) | 2 (11) | 1 (17) | 8 (18) |

†Includes one patient treated at DL2 2-dose schedule due to dosing error

Figure 3:
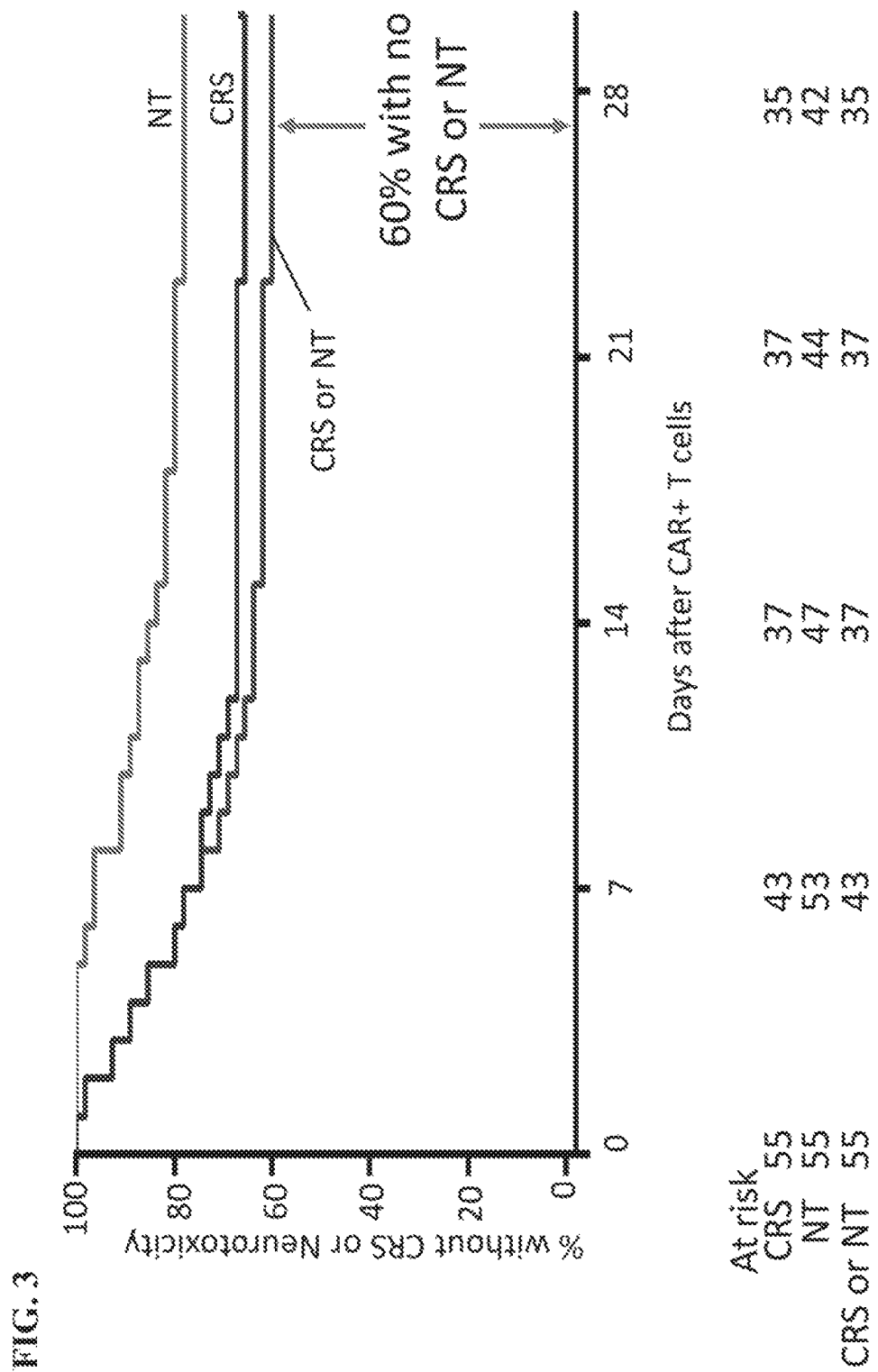
FIG. 3 is a Kaplan meier curve depicting observed time to onset of CRS and neurotoxicity.

FIG. 3 shows a Kaplan meier curve depicting observed time to onset of CRS and/or neurotoxicity. As shown, the observed median times to onset of CRS and to onset of neurotoxicity were 5 and 11 days, respectively, with only 11% of patients experiencing onset of CRS less than 72 hours after initiation of the administration of the cell therapy. The median time to resolution of CRS and neurotoxicity to Grade 1 or better was 5 and 7 days, respectively. The median time to complete resolution of CRS and neurotoxicity was 5 and 11 days, respectively. The results were consistent with a conclusion that there was a low rate of early onset of any CRS or neurotoxicity in the subjects.

C. Response to Treatment

Subjects were monitored for response, including by assessing tumor burden at 1, 3, 6, 7, 12, 18, and 24 months after administration of the CAR+ T cells. Response rates are listed in Table 8. High durable response rates were observed in the cohort of subjects, which included subjects heavily pretreated or, with poor prognosis and/or with relapsed or refractory disease. For subjects across all doses in the Core (n=44) cohort, the observed overall response rate (ORR) was 86% and the observed complete response (CR) rate was 59%. At three months for the core cohort, the overall response rate (ORR) was 66%; the three-month CR rate was 50% among the core cohort. In the core cohort, the 3 month ORR was 58% (11/19) at dose level 1 and 78% at dose level 2; the 3 month CR rate was 42% (8/19) for dose level 1 and 56% (5/9) for dose level 2, consistent with a suggested dose response effect on treatment outcome. Additionally, the results were consistent with a relationship between dose and durability of response.

Figure 5A:
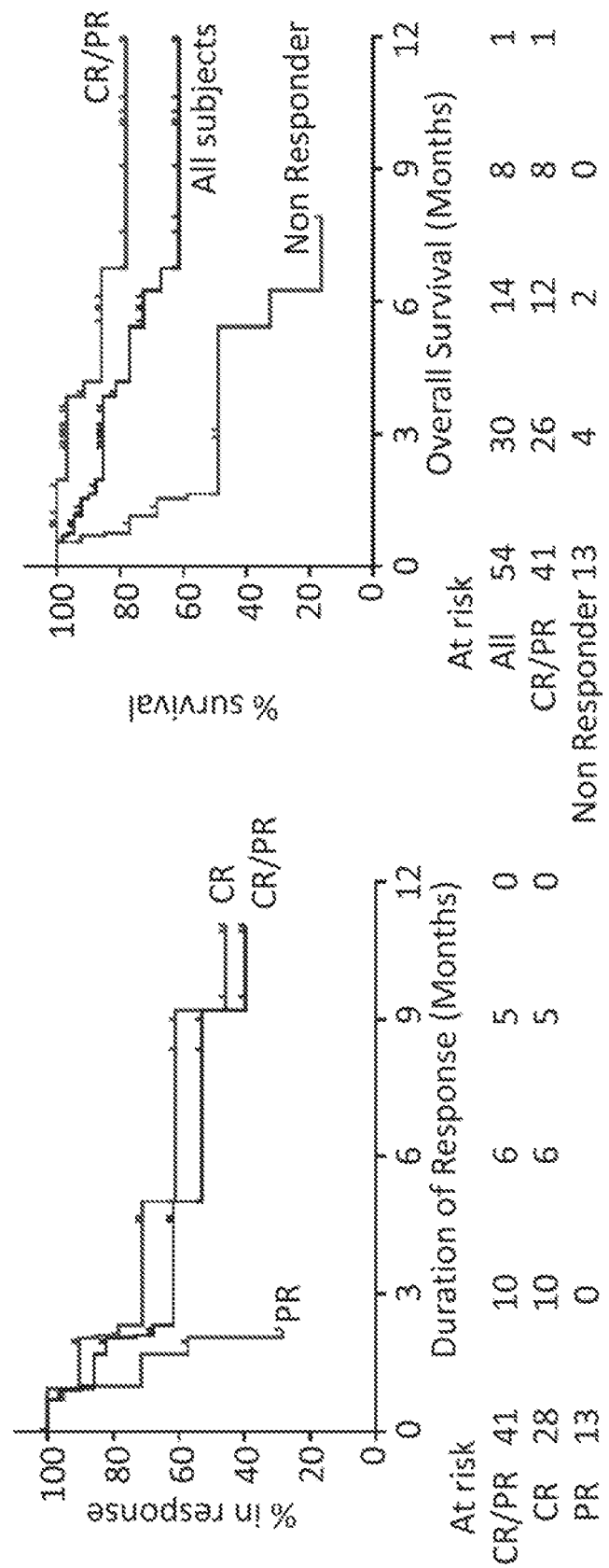
FIGS. 5A and 5B shows the duration of response (CR/PR, CR or PR) and overall survival in the full and core cohort of subjects.
Figure 5B:
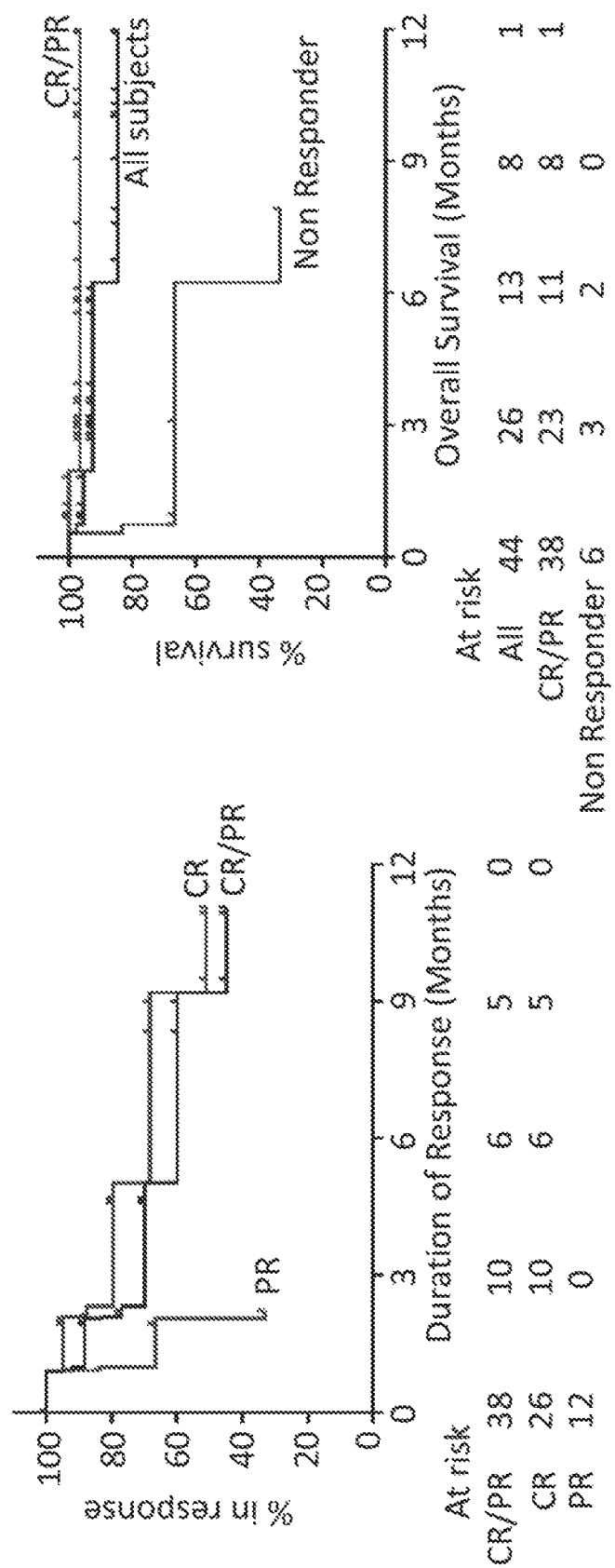

Results of the duration of response and overall survival (grouped by best overall response (non-responder, CR/PR, CR and/or PR)) are shown for full and core cohorts of subjects, in FIGS. 5A and 5B, respectively. As shown, prolonged survival was observed in responders, with increased durability of response in subjects with CRs. All patients in response at three months remained alive at the time of evaluation, although 5/6 subjects with poor performance status (ECOG 2) had expired.

C. Assessment of CAR+ T Cells in Blood

Figure 6A:
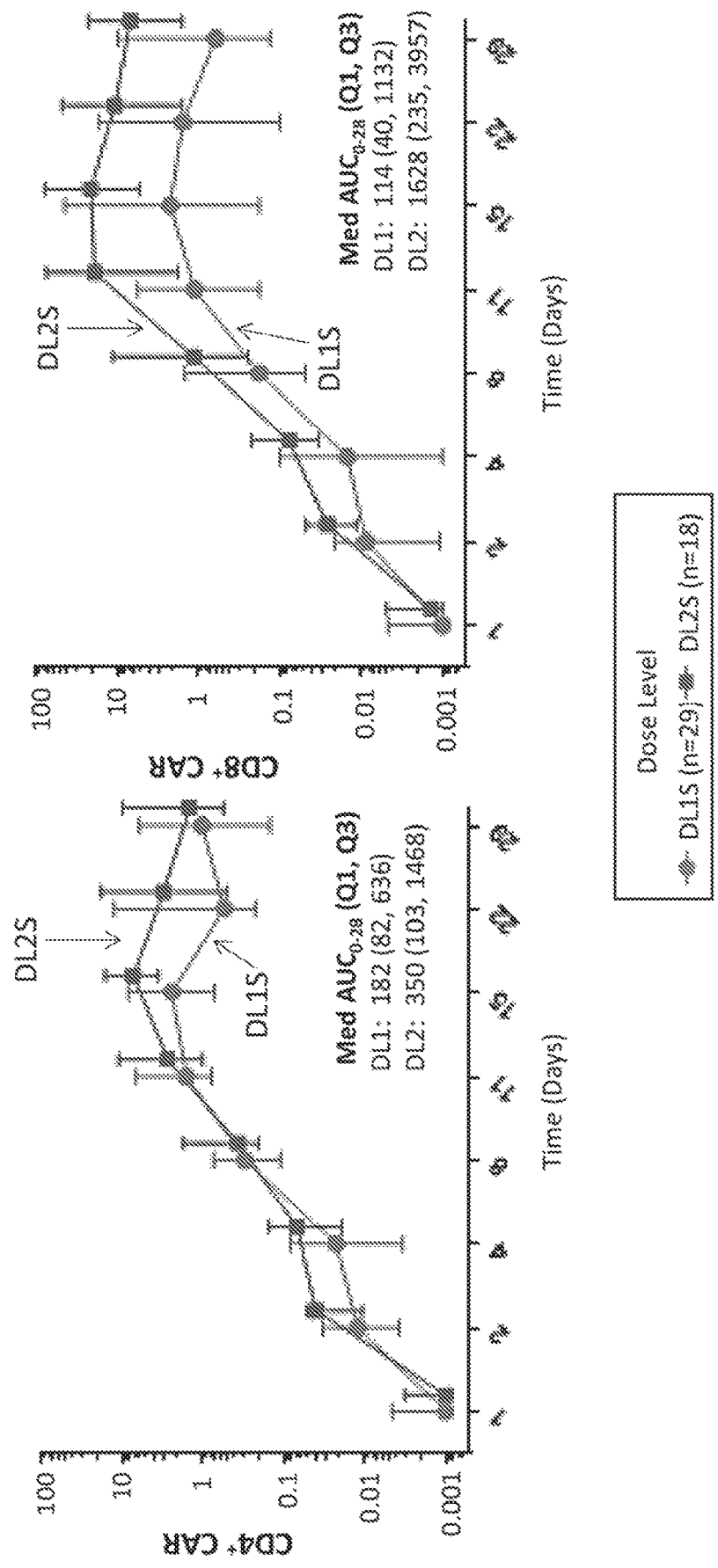
FIG. 6A shows the pharmacokinetics of the CAR+ T cells in peripheral blood at various time points post-treatment at different dose levels.

Pharmacokinetic analysis was carried out to assess numbers of CAR+ T cells in peripheral blood at various time points post-treatment. As shown in FIG. 6A, CD4+ and CD8+ CAR-expressing cells, as measured by the number of cells/4, blood (median±quartiles) plotted on a log scale, were detected throughout the course of assessment at both administered dose levels.

Figure 6B:
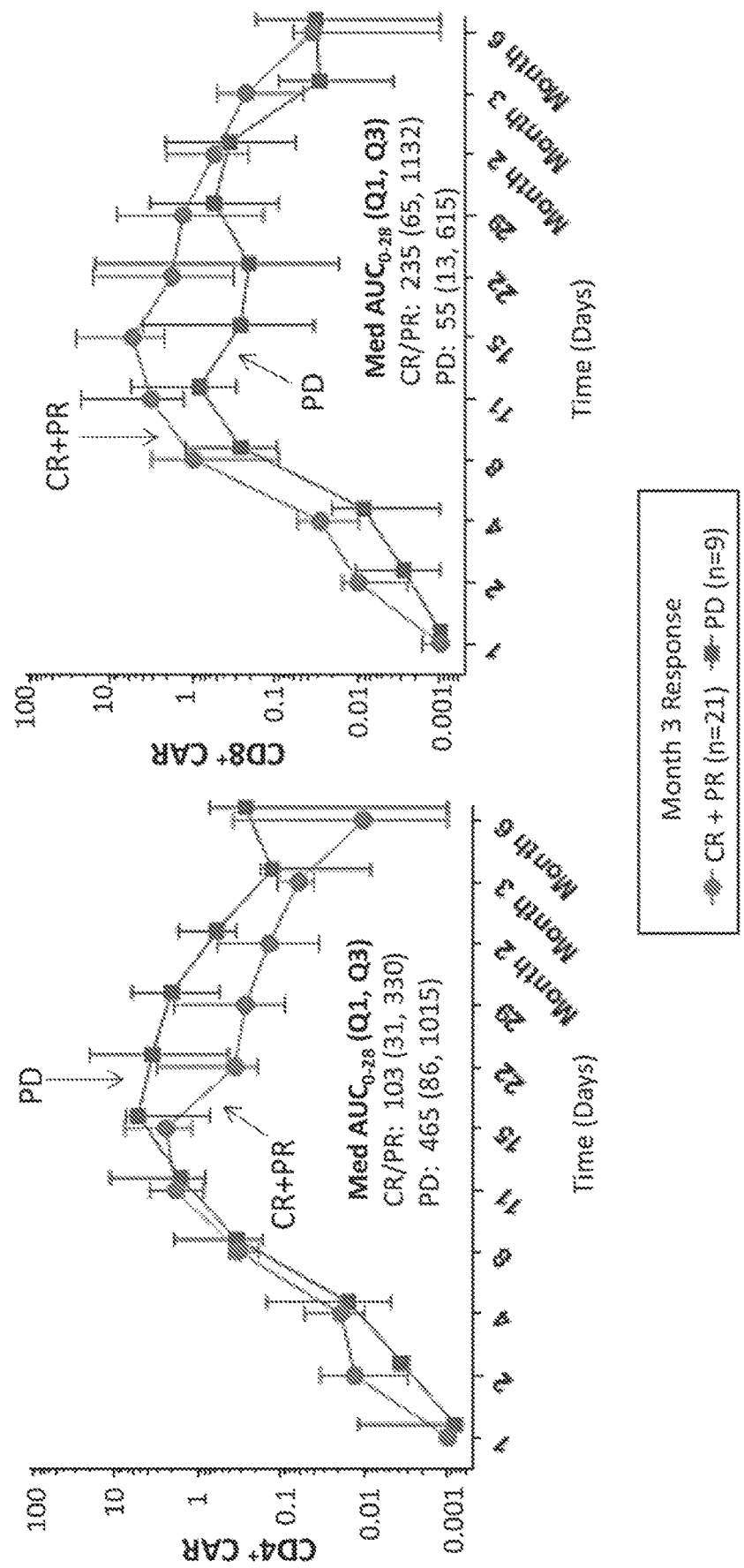
FIG. 6B shows the pharmacokinetics of the CAR+ T cells in peripheral blood at various time points post-treatment between responders and nonresponders.

An increased median area under the curve (AUC) (CD8+ CAR+ cell numbers over time in the blood) was observed among subjects administered the higher dose level, as compared to the lower dose level, without an observed increase in toxicity. Higher peak $CD8^+/CAR^+$ T cell exposure was observed in responders (CR/PR) than non-responders (PD); persistence of cells over the time of assessment, including out to 3 and 6 months, was observed even in subjects whose disease had progressed (FIG. 6B). The results were consistent with a conclusion that treatment resulted in prolonged exposure and persistence of the engineered cells, even in subjects with poor responses. In some embodiments, combination approaches are used, such as administration of an immune checkpoint modulator or other immune modulatory

TABLE 8

| | Response | | | | |
|---|---|---|---|---|---|
| | FULL | | | | |
| | All Dose Levels | DL1S | DL2S | DL1D[c] | CORE All Dose |
| Best Overall Response, N[a] | 54 | 30 | 18 | 6 | 44 |
| ORR, % (95% CI) | 76 (62, 87) | 80 (61, 92) | 72 (47, 90) | 67 (23, 96) | 86 (73, 95) |
| CR, % (95% CI) | 52 (38, 66) | 53 (34, 72) | 50 (26, 74) | 50 (12, 88) | 59 (43, 74) |
| ≥3 mos f/u, n[b] | 41 | 24 | 11 | 6 | 32 |
| 3 mo ORR, % (95% CI) | 51 (35, 67) | 46 (26, 67) | 64 (31, 89) | 50 (12, 88) | 66 (47, 81) |
| 3 mo CR, % (95% CI) | 39 (24, 56) | 33 (16, 55) | 46 (17, 77) | 50 (12, 88) | 50 (32, 68) |

Figure 4A:
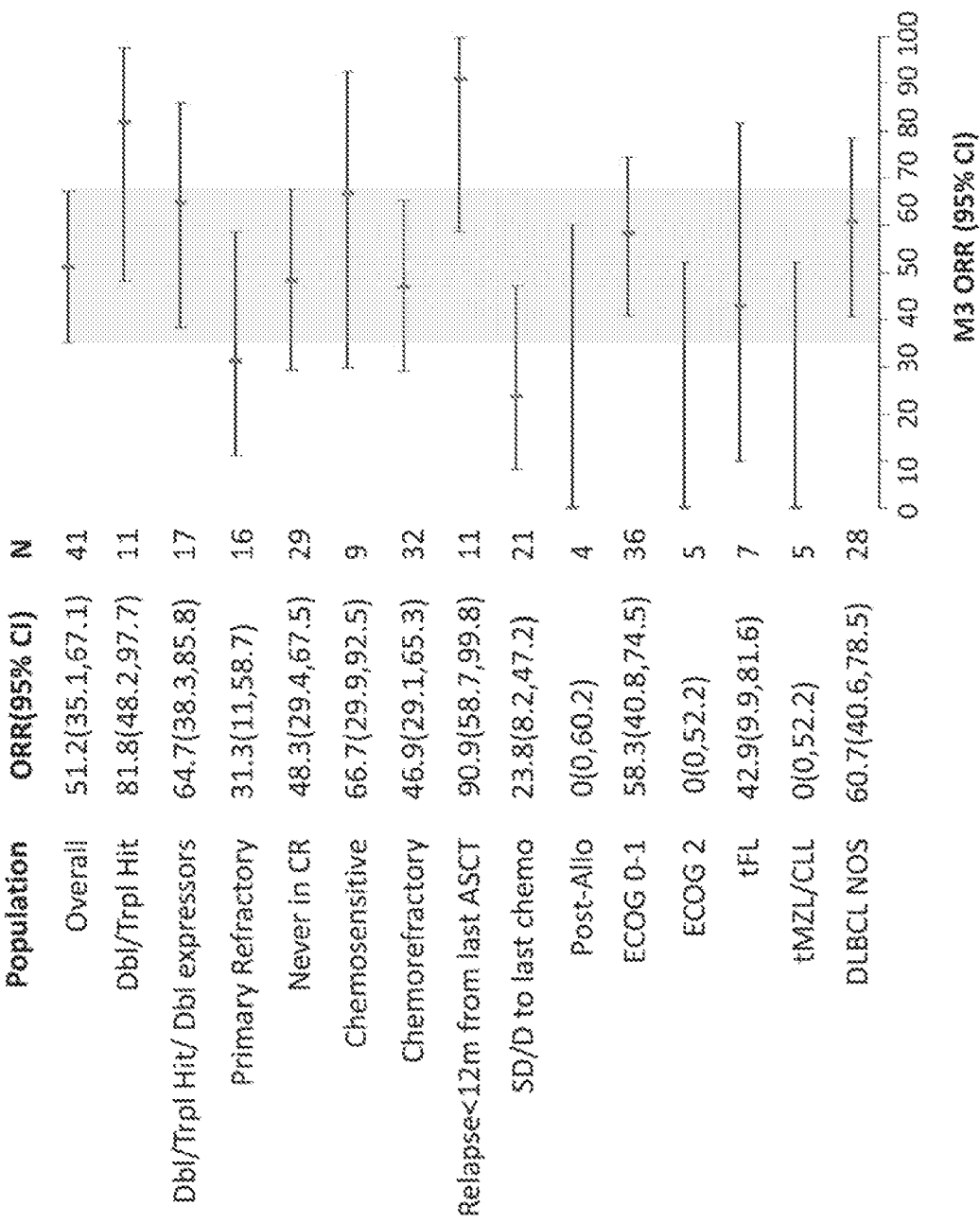
FIG. 4A and FIG. 4B depicts response rates among subgroups of treated subjects.
Figure 4B:
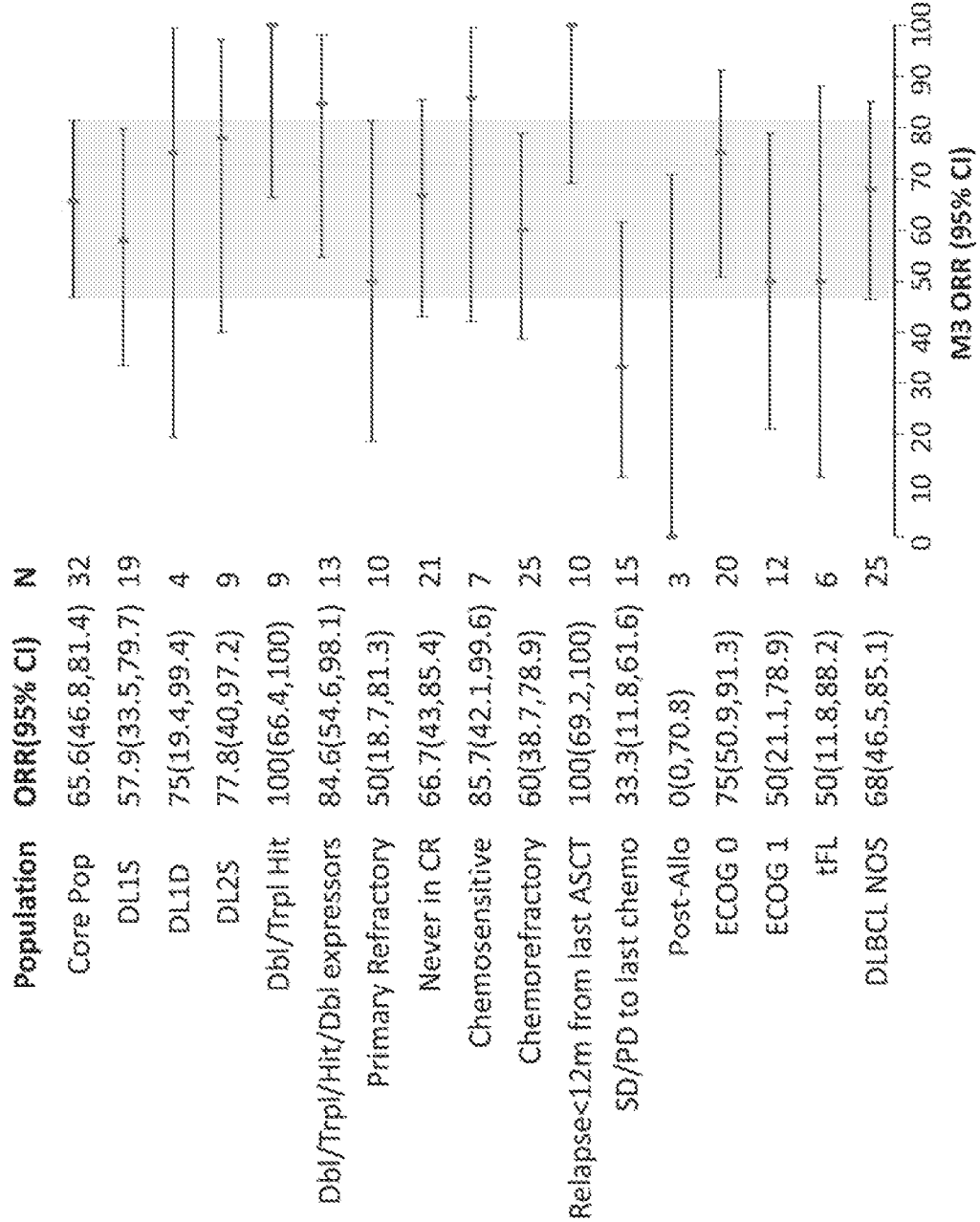

DL1S: DL1 1-dose schedule; DL2S: DL2 1-dose schedule; DL1D: DL1 2-dose schedule;
[a]Included patients with event of PD, death, or 28 day restaging scans. Treated patients <28 days prior to data snapshot were not included.
[b]The denominator is number of patients who received the CAR T-cell therapy ≥3 months ago, prior date with an efficacy assessment at Month 3 or prior assessment of PD or death.
[c]Includes one patient treated at DL2 2-dose schedule due to dosing error Overall response rates among various subgroups of subjects in the full and core cohorts are shown in FIGS. 4A and 4B, respectively. In poor-risk DLBCL subgroups, response rates were generally high. An ORR of greater than 50% was observed at 3 months in patients with double/triple hit molecular subtype, that had primary refractory or chemorefractory DLBCL or that never before had achieved a CR. Complete resolution of CNS involvement by lymphoma was observed in 2 patients.

Figure 6C:
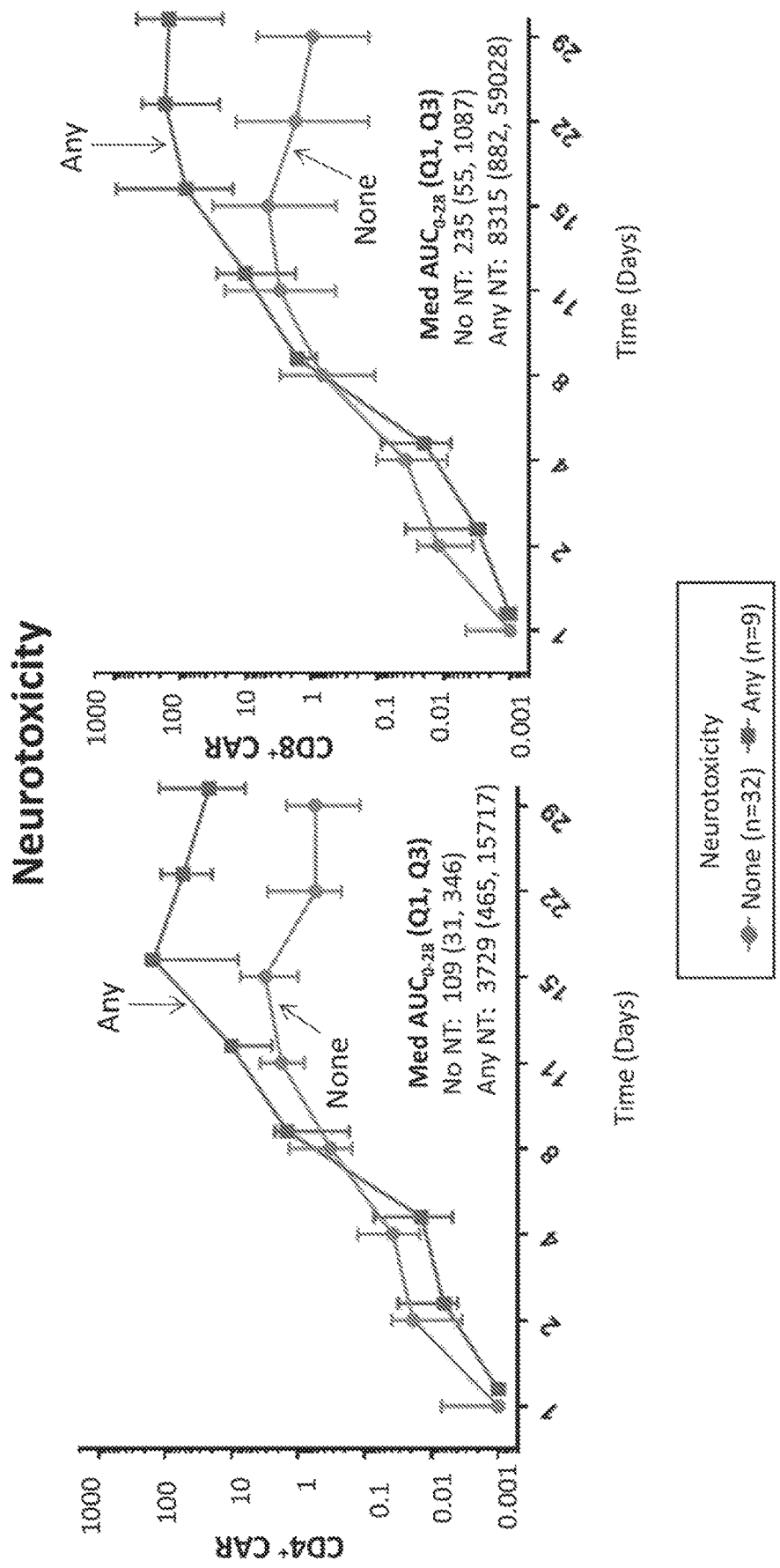
FIG. 6C shows the pharmacokinetics of the CAR+ T cells in peripheral blood at various time points post-treatment in subjects that did or did not develop any neurotoxicity.

Among the subjects treated six months or greater prior to the particular time-point of the evaluation, of the ten (10) patients that had been in response at three months, 9 (90%) remained in response at six months. At the evaluation time-point, 97% of subjects in the core subset who had responded were alive and in follow-up, median follow-up time 3.2 months.

agent, e.g., following relapse or disease progression, at a time at which engineered cells persist in the subject, e.g., as measured by levels of cells in peripheral blood. In some aspects, the cells, having persisted for a prolonged period, re-expand or become activated and/or exhibit anti-tumor function, following administration of the other agent or treatment. Higher median CD4+ and CD8+ CAR+ T cell numbers were generally observed over time in blood of subjects who developed neurotoxicity (FIG. 6C).

D. Blood Analytes and Neurotoxicity

Figure 7:
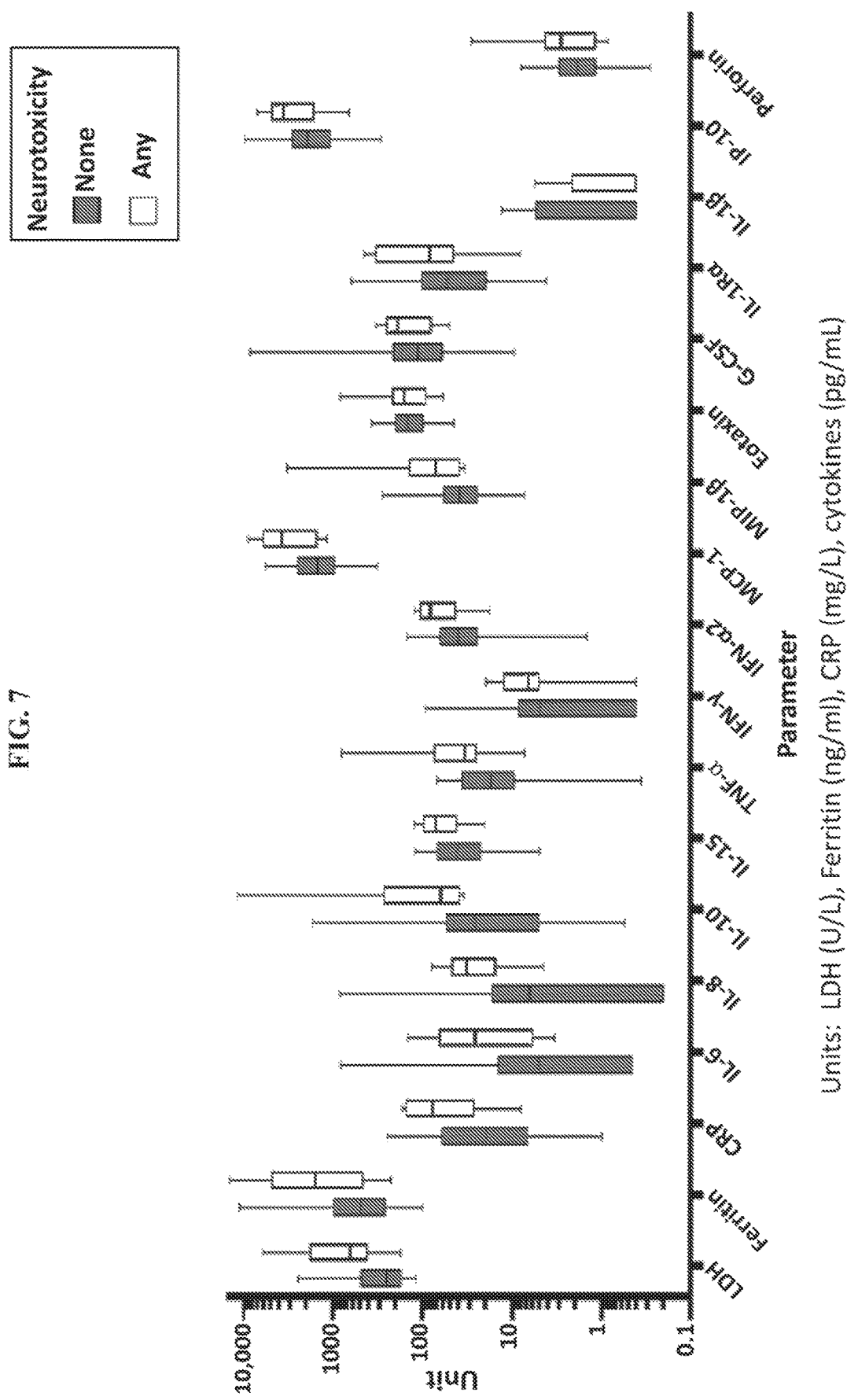
FIG. 7 shows levels of analytes measured in the serum of subjects prior to administration of the CAR+ T cells and correlation to the development of neurotoxicity.

Various pre-treatment blood analytes, including cytokines, were measured in the serum of the subjects prior to administration of the CAR+ T cells. Potential correlations to risk of developing neurotoxicity were assessed using statistical analysis. FIG. 7 shows median levels of the assessed analytes in units (LDH, U/L; ferritin, ng/mL; CRP, mg/L; cytokines, pg/mL) in subjects that did not develop a neurotoxicity versus subjects that did develop a neurotoxcity following CAR+ T cell therapy. Levels of certain blood analytes, including LDH, Ferritin, CRP, IL-6, IL-8, IL-10, TNF-α, IFN-α2, MCP-1 and MIP-1β, were observed to be associated with level of risk of developing neurotoxicity (Wilcoxon p values <0.05, without multiplicity adjustment). In particular, the results were consistent with a conclusion that pre-treatment levels of LDH, which in some embodiments is a surrogate for disease burden, may be useful for potential neurotoxicity risk assessment and/or risk-adapted dosing or adjustment of treatment of certain subjects. In addition, tumor burden measured before administration of the CAR-T cell composition correlated (Spearman p values <0.05) with the risk of developing neurotoxicity. In some aspects, LDH levels may be assessed alone and/or in combination with another pre-treatment parameter, such as another measure or indicator of disease burden, such as a volumetric tumor measurement such as sum of product dimensions (SPD) or other CT-based or MM-based volumetric measurement of disease burden. In some aspects, one or more parameters indicative of disease burden are assessed, and in some contexts may indicate the presence, absence or degree of risk of developing neurotoxicity following the T cell therapy. In some aspects, the one or more parameters include LDH and/or a volumetric tumor measurement.

Figure 8:
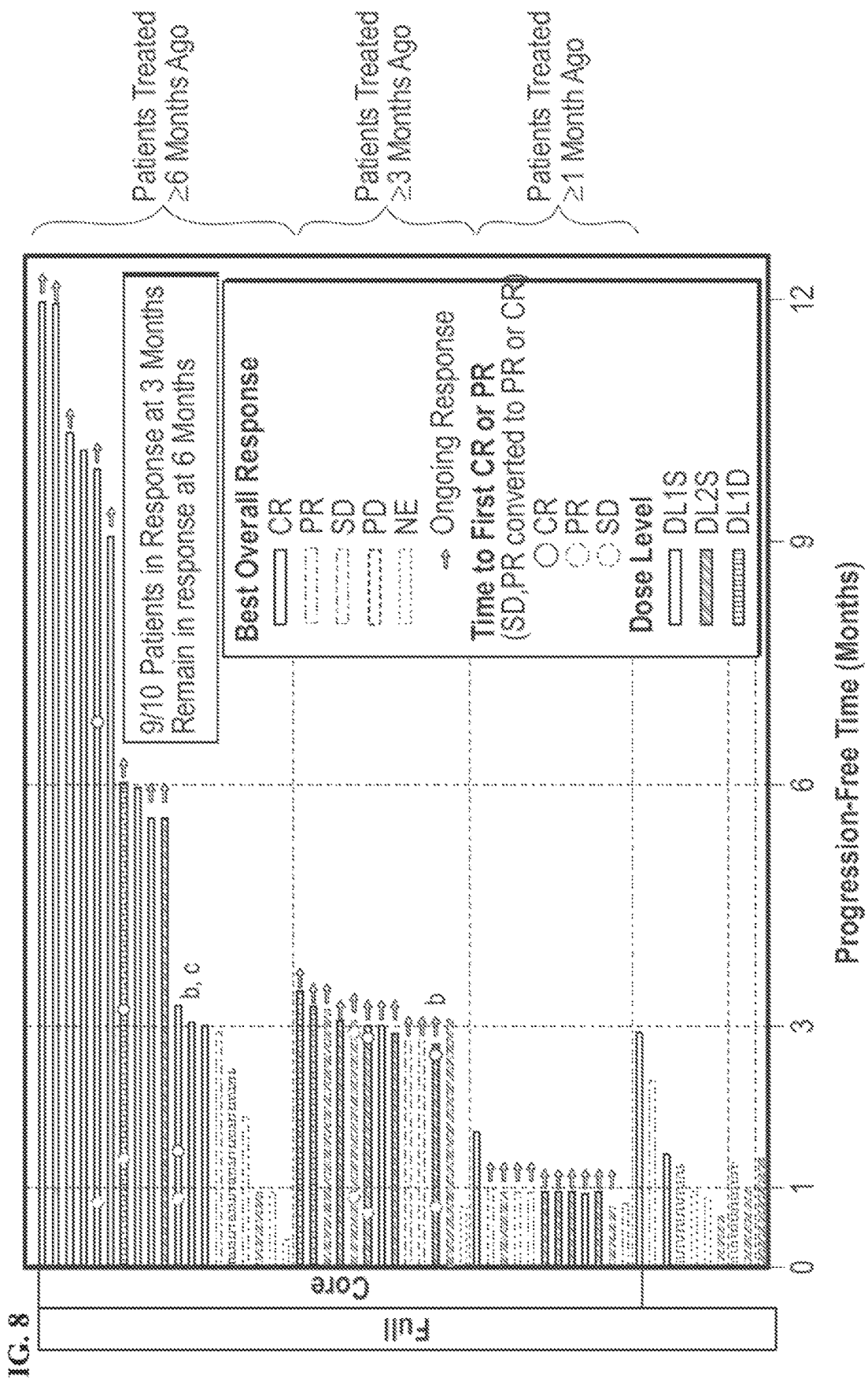
FIG. 8 shows a graph plotting progression-free time (months) and indicating best overall response and response durability, and individual clinical outcomes observed over time in individual subjects within a Full cohort and a Core cohort of NHL subjects treated with an anti-CD19 cell therapy containing CAR-T-expressing CD4+ and CD8+ T cells. $^a$: Patients achieved BOR at month 1 except where otherwise noted; $^b$: Complete resolution of CNS involvement by lymphoma observed in 2 patients; $^c$: One patient re-expanded after biopsy upon disease progression

FIG. 8 shows a graph plotting progression-free time (months) for individual subjects within the full and core cohorts. Each bar represents a single patient. Shading indicates best overall response (in each case, unless otherwise indicated, achieved at 1 month); texture indicates dose (solid=dose level 1 (DL1), single dose; cross-hatched, dose-level 2 (DL2), single dose; vertical hatched=dose level 1 (DL1), two-dose). Horizontal arrows indicate an ongoing response. Certain individual subjects were initially assessed (e.g., at 1-month) as exhibiting stable disease (SD) or Partial Response (PR), and were later observed to have achieved a PR (e.g., conversion of SD to PR) or CR. In such cases, shading of the individual patient bar, as noted, indicates best overall response, and dots (same correspondence of shading to response achieved) along each individual subject bar, indicate when each SD, PR, and/or CR was observed to have occurred in the subject. Complete resolution of CNS involvement by lymphoma was observed in two patients. CAR+ cells in one subject were observed to have expanded following biopsy after relapse.

Example 3: Administration of Anti-CD19 CAR-Expressing Cells to Subjects with Mantle Cell Lymphoma (MCL)

Therapeutic CAR+ T cell compositions containing autologous T cells expressing a chimeric antigen-receptor (CAR) specific for CD19, generated as described in Example 1, were administered to four (4) human subjects with mantle cell lymphoma (MCL) that had failed 1 line of therapy. The cryopreserved cell compositions were thawed prior to intravenous administration. The therapeutic T cell composition was administered as a defined composition cell product with formulated CD4+ and CD8+ populations of CAR+ engineered T cells derived from the same subject administered at a target ratio of approximately 1:1. Subjects were administered a dose of CAR-expressing T cells (as a split dose of the CD4+ and CD8+ CAR-expressing T cells) at a single dose of dose level 1 (DL1) containing $5 \times 10^7$ CAR-expressing T cells. Beginning at three (3) days prior to CAR+ T cell infusion, subjects received a lymphodepleting chemotherapy with flurabine (flu, 30 mg/m$^2$) and cyclophosphamide (Cy, 300 mg/m$^2$).

Subjects were monitored for response and toxicities as described in Example 1. No CRS or neurotoxicity was observed in any of the subjects. Of the 4 subjects that were treated, two (2) subjects achieved PR (not durable) and two (2) patients had progressive disease.

Example 4: Further Assessment of CD14+ Monocytes in Apheresis Sample, Response and Safety Outcomes in Subjects with Relapsed and Refractory Non-Hodgkin's Lymphoma (NHL) after Administration of Anti-CD19 CAR-Expressing Cells Response, safety outcomes, and correlations of the percentage CD14+ monocytes in apheresis samples to neurotoxicity outcomes were assessed in patients that had been administered autologous anti-CD19 CAR+ T cell compositions, at a subsequent point in time in the clinical study described in Examples 1 and 2 above.

The analysis at this time point presented in this example is based on assessment of subjects who had DLBCL (DLBCL, NOS de novo and transformed from follicular lymphoma; high grade B-cell lymphoma (double/triple hit); DLBCL transformed from CLL or MZL; PMBCL; and FL3B, ECOG 0-2, after 2 lines of therapy; the CORE cohort for analysis included subjects having DLBCL, NOS and transformed from follicular lymphoma (tFL) or high grade B-cell lymphoma (double/triple hit) and with Eastern Cooperative Oncology Group performance status (ECOG PS) of 0 or 1. Many of the treated patients in the FULL and the CORE cohort had at least one poor-risk disease feature predictive of short median overall survival (OS) of 3-6 months (see Crump et al., Blood (2017) 130:1800-1808 and Van de Neste et al., Bone Marrow Transplant. (2016) 51(1): 51-7), such as double/triple hit expressors, primary refractory disease, refractory to 2 or more lines of therapy, never achieved CR, never received autologous stem cell transplant (ASCT) or an ECOG PS of 2.

Apheresis samples were obtained from the subjects and assessed for the percentage of CD14+ monocytes of live CD45+ cells in the sample, generally as described in Example 1. The percentage of CD14+ monocytes was correlated, post facto, to the development of neurotoxicity in individual subjects following administration of the autologous therapeutic CAR+ T cell composition.

After treatment with the therapeutic CAR+ T cell composition, the subjects were assessed for response outcomes (overall response rate (ORR), complete response (CR), partial response (PR)), durable response (3-month and 6-month ORR and CR). Duration of response (DOR) and overall survival was also assessed in various response groups. High durable ORR in the poor-risk DLBCL subgroup was observed for anti-CD19 CAR+ T cell administration. In addition, in the core cohort, subjects with CR at 3 months continued to show CR at 6 months, and subjects who exhibited CR at 6 months continued to show a response longer term. The results were consistent with an observation that administration of anti-CD19 CAR+ cell compositions that contains a precise and consistent dose of CD4$^+$ and CD8$^+$ CAR+ T cells results in durable response in subjects with R/R aggressive NHL with poor prognosis and/or heavy pretreatment. The results showed a favorable durable response rate in the CORE cohort.

The subjects were also assessed and monitored for safety outcomes, including development of neurotoxicity and cytokine release syndrome (CRS), substantially as described in Examples 1 and 2. The results also were consistent with manageable toxicity and a favorable safety profile, including low rates of severe CRS and severe neurotoxicity. Of the assessed subjects, 79% (80/101) did not exhibit any neurotoxicity, while 21% (21/101) of subjects developed a grade 1-4 neurotoxicity (any NTX Gr), with Grade 3 or higher (NTX Gr3+) neurotoxicity observed in 10% (10/101) of subjects.

Figure 9A:
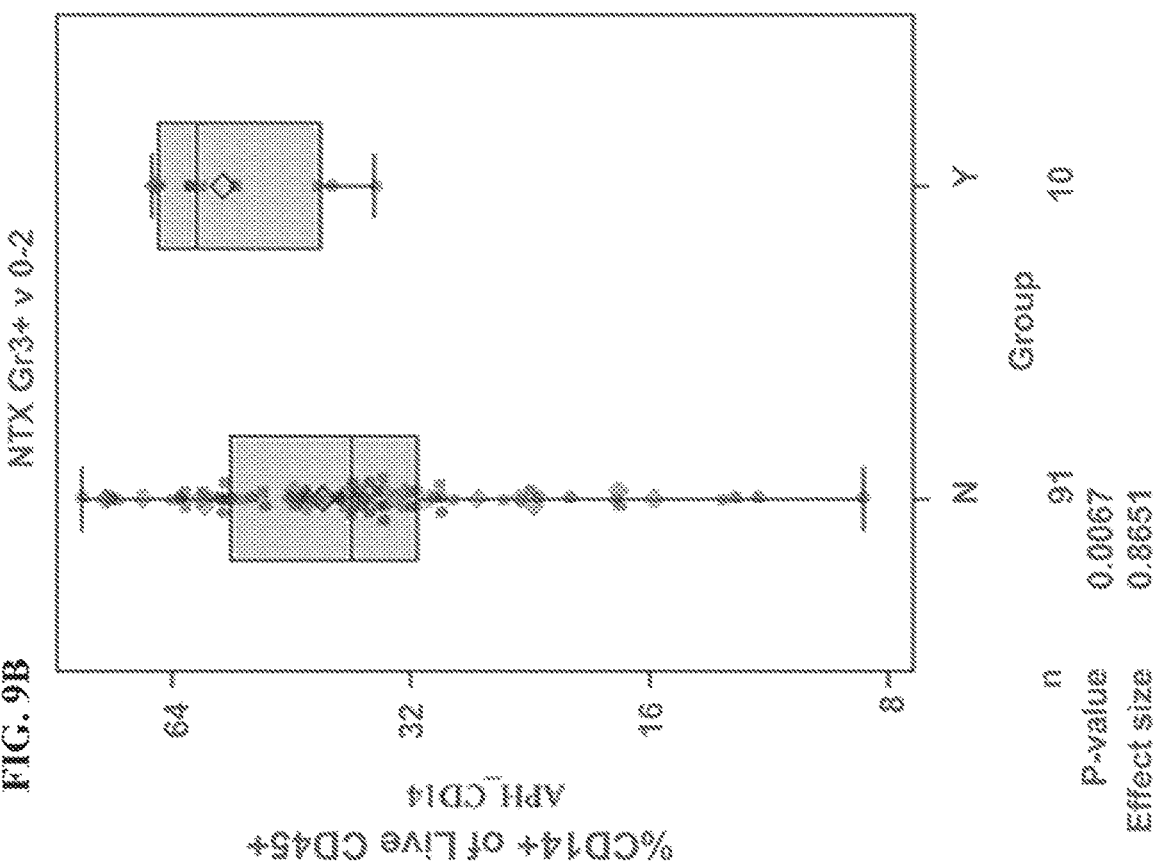
FIG. 9A shows a graph displaying the percentages of CD14+ monocytes of CD45+ cells in apheresis samples in subjects. Data is shown for subjects who did not develop neurotoxicity (left) versus subjects who developed neurotoxicity (right).
Figure 9B:
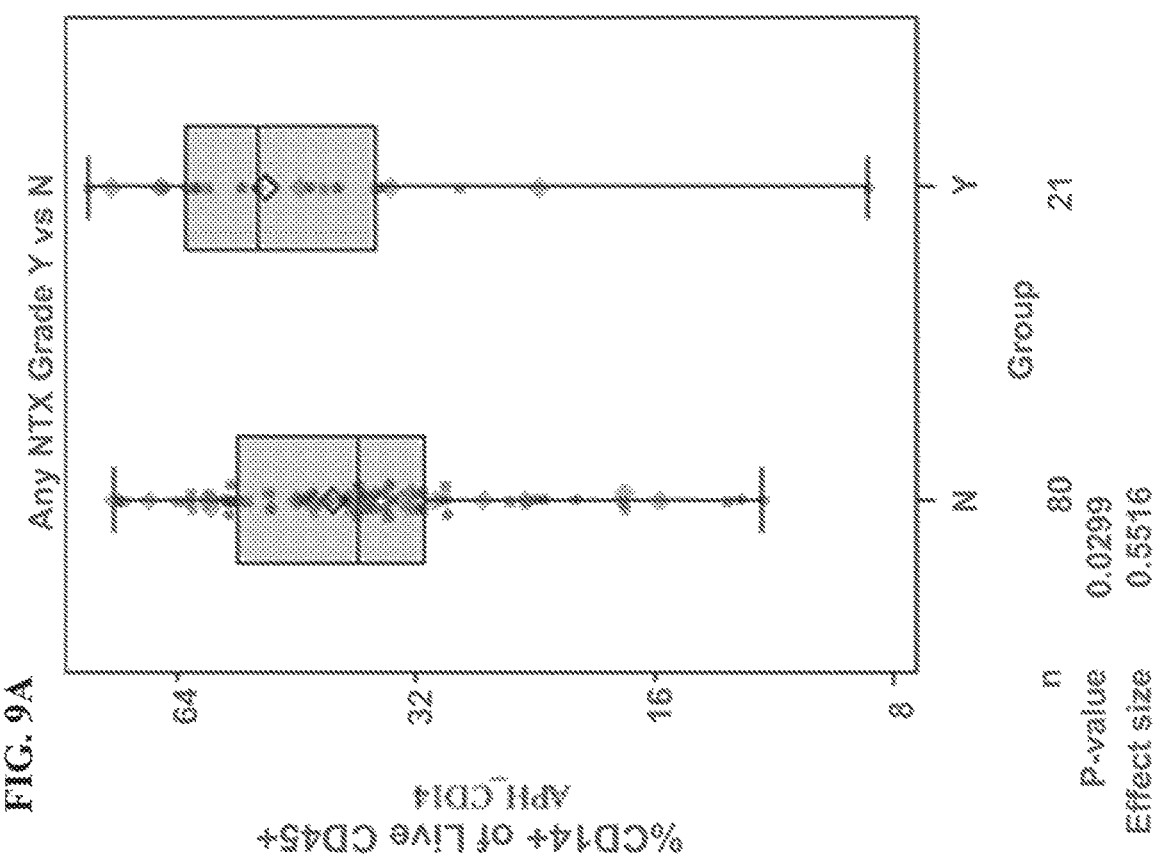
FIG. 9B shows a graph displaying the percentages of CD14+ monocytes of CD45+ cells in apheresis samples in subjects. Data is shown for subjects who did not develop neurotoxicity (left) versus subjects who developed Grade 3 or higher neurotoxicity (right).

The degree of correlation of percent CD14+ monocytes in apheresis samples to neurotoxicity in individual subjects following infusion of autologous CAR+ T cells was assessed by univariate analysis. As shown in FIGS. 9A and 9B, subjects that did not develop any neurotoxicity had a significantly lower percentage of CD14+ monocytes among live leukocytes in leukapheresis samples, compared to the percentage in leukaphresis samples from subjects that developed neurotoxicity (p=0.0299) or grade 3+ higher neurotoxicity (p=0.0067). An effect size of 0.5516 was calculated for the results between the groups with any or no neurotoxicity and an effect size of 0.8651 was calculated for the results between the groups with grades 0-2 neurotoxicity and severe (grade 3+) neurotoxicity.

The results are consistent with the finding that the presence of myeloid cells (e.g. monocytes), such as determined by the myeloid-specific marker CD14, is an intrinsic factor of leukapheresis samples in individual subjects for predicting risk of developing neurotoxicity in connection with subsequent administration of autologous CAR-expressing T cells.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
| --- | --- | --- |
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) Homo sapiens |
| 3 | ESKYGPPCPPCPGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK | Hinge-CH3 spacer Homo sapiens |
| 4 | ESKYGPPCPPCPAPEFLGGPSVFLFPPKPKDTLMISRTPEVTCVVVDVSQEDPEVQFNWYVDGVE VHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVD KSRWQEGNVFSCSVMHEALHNHYTQKSLLSLGKS | Hinge-CH2–CH3 spacer Homo sapiens |
| 5 | RWPESPKAQASSVPTAQPQAEGSLAKATTAPATTRNTGRGGEEKKKEKEKEEQEERETKTPECPS HTQPLGVYLLTPAVQDLWLRDKATFTCFVVGSDLKDAHLTWEVAGKVPTGGVEEGLLERHSNGSQ SQHSRLTLPRSLWNAGTSVTCTLNHPSLPPQRLMALREPAAQAPVKLSLNLLASSDPPEAASWLL CEVSGFSPPNILLMWLEDQREVNTSGFAPARPPPQPGSTTFWAWSVLRVPAPPSPQPATYTCVVS HEDSRTLLNASRSLEVSYVTDH | IgD-hinge-Fc Homo sapiens |
| 6 | LEGGGEGRGSLLTCGDVEENPGPR | T2A artificial |
| 7 | RKVCNGIGIGEFKDSLSINATNIKHFKNCTSISGDLHILPVAFRGDSFTHTPPLDPQELDILKTV KEITGFLLIQAWPENRTDLHAFENLEIIRGRTKQHGQFSLAVVSLNITSLGLRSLKEISDGDVII SGNKNLCYANTINWKKLFGTSGQKTKIISNRGENSCKATGQVCHALCSPEGCWGPEPRDCVSCRN VSRGRECVDKCNLLEGEPREFVENSECIQCHPECLPQAMNITCTGRGPDNCIQCAHYIDGPHCVK TCPAGVMGENNTLVWKYADAGHVCHLCHPNCTYGCTGPGLEGCPTNGPKIPSIATGMVGALLLL LVVALGIGLFM | tEGFR artificial |
| 8 | FWVLVVVGGVLACYSLLVTVAFIIFWV | CD28 (amino acids 153-179 of Accession No. P10747) Homo sapiens |
| 9 | IEVMYPPPYLDNEKSNGTIIHVKGKHLCPSPLFPGPSKPFWVLVVVGGVLACYSLLVTVAFIIFW V | CD28 (amino acids 114-179 of Accession No. P10747) Homo sapiens |
| 10 | RSKRSRLLHSDYMNMTPRRPGPTRKHYQPYAPPRDFAAYRS | CD28 (amino acids 180-220 of P10747) Homo sapiens |

-continued

| SEQ ID NO. | SEQUENCE | DESCRIPTION |
|---|---|---|
| 11 | RSKRSRGGHSDYMNMTPRRPGPTRKHYQPYAPPRDFAAYRS | CD28 (LL to GG) *Homo sapiens* |
| 12 | KRGRKKLLYIFKQPFMRPVQTTQEEDGCSCRFPEEEEGGCEL | 4-1BB (amino acids 214-255 of Q07011.1) *Homo sapiens* |
| 13 | RVKFSRSADAPAYQQGQNQLYNELNLGRREEYDVLDKRRGRDPEMGGKPRRKNPQEGLYNELQKD KMAEAYSEIGMKGERRRGKGHDGLYQGLSTATKDTYDALHMQALPPR | CD3 zeta *Homo sapiens* |
| 14 | RVKFSRSAEPPAYQQGQNQLYNELNLGRREEYDVLDKRRGRDPEMGGKPRRKNPQEGLYNELQKD KMAEAYSEIGMKGERRRGKGHDGLYQGLSTATKDTYDALHMQALPPR | CD3 zeta *Homo sapiens* |
| 15 | RVKFSRSADAPAYKQGQNQLYNELNLGRREEYDVLDKRRGRDPEMGGKPRRKNPQEGLYNELQKD KMAEAYSEIGMKGERRRGKGHDGLYQGLSTATKDTYDALHMQALPPR | CD3 zeta *Homo sapiens* |
| 16 | PGGG-(SGGGG)5-P- wherein P is proline. G is glycine and S is serine | linker |
| 17 | GSADDAKKDAAKKDGKS | Linker |
| 18 | EGRGSLLTCGDVEENPGP | T2A artificial |
| 19 | PLGLWA | MMP cleavable linker |
| 20 | GSGATNFSLLKQAGDVEENPGP | P2A |
| 21 | ATNFSLLKQAGDVEENPGP | P2A |
| 22 | QCTNYALLKLAGDVESNPGP | E2A |
| 23 | VKQTLNFDLLKLAGDVESNPGP | F2A |
| 24 | atgcttctcctggtgacaagccttctgctctgtgagttaccacacccagcattcctcctgatccca | GMCSFR alpha chain signal sequence |
| 25 | MLLLVTSLLLCELPHPAFLLIP | GMCSFR alpha chain signal sequence |
| 26 | MALPVTALLLPLALLLHA | CD8 alpha signal peptide |
| 27 | MERASCLLLLLLPLVHVSATTPEPCELDDEDFRCVCNFSEPQPDWSEAFQCVSAVEVEIHAGGLN LEPFLKRVDADADPRQYADTVKALRVRRLTVGAAQVPAQLLVGALRVLAYSRLKELTLEDLKITG TMPPLPLEATGLALSSLRLRNVSWATGRSWLAELQQWLKPGLKVLSIAQAHSPAFSCEQVRAFPA LTSLDLSDNPGLGERGLMAALCPHKFPAIQNLALRNTGMETPTGVCAALAAAGVQPHSLDLSHNS LRATVNPSAPRCMWSSALNSLNLSFAGLEQVPKGLPAKLRVLDLSCNRLNRAPQPDELPEVDNLT LDGNPFLVPGTALPHEGSMNSGVVPACARSTLSVGVSGTLVLLQGARGFA | Human CD14 |
| 28 | TTPEPCELDDEDFRCVCNFSEPQPDWSEAFQCVSAVEVEIHAGGLNLEPFLKRVDADADPRQYAD TVKALRVRRLTVGAAQVPAQLLVGALRVLAYSRLKELTLEDLKITGTMPPLPLEATGLALSSLRL RNVSWATGRSWLAELQQWLKPGLKVLSIAQAHSPAFSCEQVRAFPALTSLDLSDNPGLGERGLMA ALCPHKFPAIQNLALRNTGMETPTGVCAALAAAGVQPHSLDLSHNSLRATVNPSAPRCMWSSALN SLNLSFAGLEQVPKGLPAKLRVLDLSCNRLNRAPQPDELPEVDNLTLDGNPFLVPGTALPHEGSM N | Mature human CD14 |
| 29 | GSTSGSGKPGSGEGSTKG | Linker |
| 30 | gacatccaga tgacccagac cacctccagc ctgagcgcca gcctgggcga ccgggtgacc atcagctgcc gggccagcca ggacatcagc aagtacctga actggtatca gcagaagccc gacggcaccg tcaagctgct gatctaccac accagccggc tgcacagcgg cgtgcccagc cggtttagcg gcagcggctc cggcaccgac tacagcctga ccatctccaa cctggaacag gaagatatcg ccacctactt ttgccagcag ggcaacacac tgccctacac ctttggcggc ggaacaaagc tggaaatcac cggcagcacg gcaagccagg cagcggcagg ggcagcacca agggcgaggt gaagctgcag gaaagcggcc ctggcctggt ggcccccagc cagagcctga gcgtgacctg caccgtgagc ggcgtgagcc tgcccgacta cggcgtgagc tggatccggc agccccccag gaagggcctg aatggctggg gcgtgatctg ggcagcgag accacctact acaacagcgc cctgaagagc cggctgacca tcatcaagga caacagcaag agccaggtgt tcctgaagat gaacagcctg cagaccgacg acaccgccat | Sequence encoding scFv |

| SEQ ID NO. | SEQUENCE | DESCRIPTION |
|---|---|---|
|  | ctactactgcgccaagcact actactacgg cggcagctac gccatggact actggggcca gggcaccagc gtgaccgtga gcagc |  |
| 31 | $X_1PPX_2P$<br>$X_1$ is glycine, cysteine or arginine<br>$X_2$ is cysteine or threonine | Hinge |
| 32 | Glu Pro Lys Ser Cys Asp Lys Thr His Thr Cys Pro Pro Cys Pro | Hinge |
| 33 | Glu Arg Lys Cys Cys Val Glu Cys Pro Pro Cys Pro | Hinge |
| 34 | ELKTPLGDTHTCPRCPEPKSCDTPPPCPRCPEPKSCDTPPPCPRCPEPKSCDTPPPCPRCP | Hinge |
| 35 | Glu Ser Lys Tyr Gly Pro Pro Cys Pro Ser Cys Pro | Hinge |
| 36 | Glu Ser Lys Tyr Gly Pro Pro Cys Pro Pro Cys Pro | Hinge |
| 37 | Tyr Gly Pro Pro Cys Pro Pro Cys Pro | Hinge |
| 38 | Lys Tyr Gly Pro Pro Cys Pro Pro Cys Pro | Hinge |
| 39 | Glu Val Val Val Lys Tyr Gly Pro Pro Cys Pro Pro Cys Pro | Hinge |
| 40 | RASQDISKYLN | FMC63 CDR L1 |
| 41 | SRLHSGV | FMC63 CDR L2 |
| 42 | GNTLPYTFG | FMC63 CDR L3 |
| 43 | DYGVS | FMC63 CDR H1 |
| 44 | VIWGSETTYYNSALKS | FMC63 CDR H2 |
| 45 | YAMDYWG | FMC63 CDR H3 |
| 46 | EVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS | FMC63 VH |
| 47 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEIT | FMC63 VL |
| 48 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS | FMC63 scFv |
| 49 | KASQNVGTNVA | SJ25C1 CDR L1 |
| 50 | SATYRNS | SJ25C1 CDR L2 |
| 51 | QQYNRYPYT | SJ25C1 CDR L3 |
| 52 | SYWMN | SJ25C1 CDR H1 |
| 53 | QIYPGDGDTNYNGKFKG | SJ25C1 CDR H2 |
| 54 | KTISSVVDFYFDY | SJ25C1 CDR H3 |
| 55 | EVKLQQSGAELVRPGSSVKISCKASGYAFSSYWMNWVKQRPGQGLEWIGQIYPGDGDTNYNGKFKGQATLTADKSSSTAYMQLSGLTSEDSAVYFCARKTISSVVDFYFDYWGQGTTVTVSS | SJ25C1 VH |
| 56 | DIELTQSPKFMSTSVGDRVSVTCKASQNVGTNVAWYQQKPGQSPKPLIYSATYRNSGVPDRFTGSGSGTDFTLTITNVQSKDLADYFCQQYNRYPYTSGGGTKLEIKR | SJ25C1 VL |
| 57 | GGGGSGGGGSGGGGS | Linker |
| 58 | EVKLQQSGAELVRPGSSVKISCKASGYAFSSYWMNWVKQRPGQGLEWIGQIYPGDGDTNYNGKFKGQATLTADKSSSTAYMQLSGLTSEDSAVYFCARKTISSVVDFYFDYWGQGTTVTVSSGGGGSGGGGSGGGGSDIELTQSPKFMSTSVGDRVSVTCKASQNVGTNVAWYQQKPGQSPKPLIYSATYRNSGVPDRFTGSGSGTDFTLTITNVQSKDLADYFCQQYNRYPYTSGGGTKLEIKR | SJ25C1 scFv |

| SEQ ID NO. | SEQUENCE | DESCRIPTION |
|---|---|---|
| 59 | HYYYGGSYAMDY | FMC63 CDR H3 |
| 60 | HTSRLHS | FMC63 CDR L2 |
| 61 | QQGNTLPYT | FMC63 CDR L3 |

What is claimed:

1. A method of selecting a subject for treatment, the method comprising:
   (a) contacting an apheresis sample with a reagent capable of detecting CD14+ myeloid cells, wherein:
      the apheresis sample is from a subject that is a candidate for treatment with a cell therapy comprising a dose of genetically engineered cells expressing a recombinant receptor; and
      the apheresis sample is obtained from the subject prior to administering the cell therapy; and
   (b) selecting for treatment a subject in which:
      i) the percentage of cells in the sample that are surface positive for CD14 is at or above a threshold level of at least 20%, thereby identifying a subject that is at risk for developing a neurotoxicity to the cell therapy; and
   (c) administering an agent capable of treating, preventing, delaying, reducing, or attenuating the development of a neurotoxicity and the cell therapy to the subject.

2. The method of claim 1, wherein:
   administration of the agent is (I) prior to, (II) within one, two, or three days of, (III) concurrently with and/or (IV) at first fever following, the initiation of administration of the cell therapy to the subject.

3. A method of treatment, comprising:
   (a) assaying an apheresis sample for a percentage of CD14+ myeloid cells, wherein the apheresis sample is from a subject that is a candidate for a cell therapy treatment comprising administration of a composition comprising a dose of genetically engineered cells expressing a recombinant receptor; and
   (b) selecting for treatment a subject having a percentage of cells in the apheresis sample that are surface positive for CD14 at or above a threshold of 20%; and
      (i) administering to the subject an agent capable of treating, preventing, delaying, reducing or attenuating the development or risk of development of a neurotoxicity;
      (ii) administering to the subject the cell therapy at a reduced dose or at a dose that is not associated with risk of developing neurotoxicity or severe neurotoxicity; or
      (iii) administering to the subject the cell therapy in an in-patient setting and/or with admission to the hospital for one or more days.

4. The method of claim 3, wherein said assaying comprises contacting the apheresis sample with a reagent capable of detecting CD14+ cells.

5. The method of claim 3, wherein the treatment comprises administering an agent capable of treating, preventing, delaying, reducing or attenuating the development or risk of development of a neurotoxicity and wherein the agent is administered
   (i) prior to, (ii) within one, two, or three days of, (iii) concurrently with and/or (iv) at first fever following, the initiation of administration of the cell therapy to the subject.

6. A method of prophylactic treatment, comprising administering to a subject, an agent capable of treating, preventing, delaying, reducing or attenuating the development or risk of development of a neurotoxicity, wherein:
   the subject is a candidate for treatment with a cell therapy comprising a composition comprising a dose of genetically engineered cells expressing a recombinant receptor; and
   the subject has been identified as at risk for developing a neurotoxicity or severe neurotoxicity based on the presence of at least 20% CD14+ myeloid cells in an apheresis sample obtained from the subject prior to administering the cell therapy.

7. The method of claim 1, wherein the threshold level is about 45%.

8. The method of claim 1, wherein the population of myeloid cells is or comprises monocytes.

9. The method of claim 1, wherein the neurotoxicity comprises, severe neurotoxicity and/or comprises:
(i) a grade 2 or higher neurotoxicity;
(ii) a grade 3 or higher neurotoxicity, or at least prolonged grade 3 neurotoxicity;
(iii) is at or above grade 4; or
(iv) grade 5 neurotoxicity.

10. The method of claim 1, wherein the neurotoxicity is severe neurotoxicity or is a grade 3 or higher neurotoxicity.

11. The method of claim 1, wherein the neurotoxicity is associated with cerebral edema.

12. The method of claim 2, wherein the agent comprises one or more of a steroid, an antagonist or inhibitor of a cytokine receptor or cytokine selected from the group consisting of IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function.

13. The method of claim 2, wherein the agent is an anti-IL-6 antibody or an anti-IL6 receptor antibody.

14. The method of claim 2, wherein the agent is selected from the group consisting of tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101.

15. The method of claim 1, wherein the recombinant receptor specifically binds to an antigen associated with a disease or condition or expressed in cells of the environment of a lesion associated with the disease or condition.

16. The method of claim 2, wherein the subject has a disease or condition that is a cancer.

17. The method of claim 2, wherein the subject has a disease or condition that is a myeloma, leukemia or lymphoma.

18. The method of claim 2, wherein the subject has a disease or condition that is a B cell malignancy, acute lymphoblastic leukemia (ALL), adult ALL, chronic lymphoblastic leukemia (CLL), non-Hodgkin lymphoma (NHL), or Diffuse Large B-Cell Lymphoma (DLBCL).

19. The method of claim 1, wherein the recombinant receptor is a T cell receptor or a functional non-T cell receptor.

20. The method of claim 1, wherein the recombinant receptor is a chimeric antigen receptor (CAR).

21. The method of claim 1, wherein the engineered cells comprise T cells.

22. The method of claim 3, wherein the population of myeloid cells is or comprises monocytes.

23. The method of claim 1, wherein the threshold is at least 30% of cells in the sample that are surface positive for CD14.

24. The method of claim 1, wherein the threshold is at least 35% of cells in the sample that are surface positive for CD14.

25. The method of claim 3, wherein the threshold is at least 30% of cells in the sample that are surface positive for CD14.

26. The method of claim 3, wherein the threshold is at least 35% of cells in the sample that are surface positive for CD14.

27. The method of claim 6, wherein the subject has been identified as at risk for developing a neurotoxicity or severe neurotoxicity based on the presence of at least 30% CD14+ myeloid cells in an apheresis sample obtained from the subject prior to administering the cell therapy.

28. The method of claim 6, wherein the subject has been identified as at risk for developing a neurotoxicity or severe neurotoxicity based on the presence of at least 35% CD14+ myeloid cells in an apheresis sample obtained from the subject prior to administering the cell therapy.

29. The method of claim 3, wherein the recombinant receptor is a chimeric antigen receptor (CAR).

30. The method of claim 6, wherein the recombinant receptor is a chimeric antigen receptor (CAR).

31. The method of claim 3, wherein the agent comprises one or more of a steroid, an antagonist or inhibitor of a cytokine receptor or cytokine selected from the group consisting of IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or
an agent capable of preventing, blocking or reducing microglial cell activity or function.

32. The method of claim 6, wherein the agent comprises one or more of a steroid, an antagonist or inhibitor of a cytokine receptor or cytokine selected from the group consisting of IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or
an agent capable of preventing, blocking or reducing microglial cell activity or function.

33. The method of claim 1, wherein the agent is capable of treating, preventing, delaying, reducing, or attenuating the or risk of development of a neurotoxicity to the subject.

* * * * *